US011485721B2

(12) United States Patent
Kloss et al.

(10) Patent No.: US 11,485,721 B2
(45) Date of Patent: Nov. 1, 2022

(54) METHOD FOR THE METAL-FREE PREPARATION OF A BIARYL BY A PHOTOSPLICING REACTION AND THEIR USES

(71) Applicant: Leibniz-Institut für Naturstoff-Forschung und Infektionsbiologie E. V. Hans-Knöll-Institut (HKI), Jena (DE)

(72) Inventors: Florian Kloss, Jena (DE); Toni Neuwirth, Jena (DE); Veit Haensch, Jena (DE); Christian Hertweck, Leipzig (DE)

(73) Assignee: Leibniz-Institut für Naturstoff-Forschung und Infektionsbiologie e. V. Hans-Knöll-Institut, Jena (DE)

( * ) Notice: Subject to any disclaimer, the term of this patent is extended or adjusted under 35 U.S.C. 154(b) by 0 days.

(21) Appl. No.: 16/765,376

(22) PCT Filed: Nov. 19, 2018

(86) PCT No.: PCT/EP2018/081727
§ 371 (c)(1),
(2) Date: May 19, 2020

(87) PCT Pub. No.: WO2019/101679
PCT Pub. Date: May 31, 2019

(65) Prior Publication Data
US 2020/0339529 A1    Oct. 29, 2020

(30) Foreign Application Priority Data
Nov. 21, 2017 (EP) .................... 17202739

(51) Int. Cl.
| | | |
|---|---|---|
| *C07D 311/80* | (2006.01) | |
| *C07C 41/18* | (2006.01) | |
| *C07C 45/67* | (2006.01) | |
| *C07C 67/333* | (2006.01) | |
| *C07C 253/30* | (2006.01) | |
| *C07C 319/14* | (2006.01) | |
| *C07D 213/803* | (2006.01) | |
| *C07D 317/50* | (2006.01) | |
| *C07D 333/60* | (2006.01) | |

(52) U.S. Cl.
CPC ............ *C07D 311/80* (2013.01); *C07C 41/18* (2013.01); *C07C 45/673* (2013.01); *C07C 67/333* (2013.01); *C07C 253/30* (2013.01); *C07C 319/14* (2013.01); *C07D 213/803* (2013.01); *C07D 317/50* (2013.01); *C07D 333/60* (2013.01)

(58) Field of Classification Search
None
See application file for complete search history.

(56) References Cited

PUBLICATIONS

International Search Report and Written Opinion dated Jan. 11, 2019 in connection with PCT/EP2018/081727.
Ackerman et al., Multimetallic catalysed cross-coupling of aryl bromides with aryl triflates. Nature. 2015;524(7566):454-457. doi:10.1038/nature14676.
Allart-Simon et al., Radical Smiles Rearrangement: An Update. Molecules. 2016;21(7):878. Published Jul. 6, 2016. doi:10.3390/molecules21070878.
Corbet et al., Selected patented cross-coupling reaction technologies. Chem Rev. 2006;106(7):2651-2710. doi:10.1021/cr0505268.
De Carolis et al., Metal-free cross-coupling reactions of aryl sulfonates and phosphates through photoheterolysis of aryl-oxygen bonds. Angew Chem Int Ed Engl. 2005;44(8):1232-1236. doi: 10.1002/anie.200461444.
Dichiarante et al., Metal-free synthesis of sterically crowded biphenyls by direct Ar—H substitution in alkyl benzenes. Angew Chem Int Ed Engl. 2007;46(34):6495-6498. doi: 10.1002/anie.200701462.
Dohi et al., Unusual ipso substitution of diaryliodonium bromides initiated by a single-electron-transfer oxidizing process. Angew Chem Int Ed Engl. 2010;49(19):3334-3337. doi:10.1002/anie.200907281.
Elsler et al., Metal- and reagent-free highly selective anodic cross-coupling reaction of phenols. Angew Chem Int Ed Engl. 2014;53(20):5210-5213. doi:10.1002/anie.201400627.
Goossen et al., Synthesis of biaryls via catalytic decarboxylative coupling. Science. 2006;313(5787):662-664. doi:10.1126/science.1128684.
Hari et al., Metal-free, visible-light-mediated direct C—H arylation of heteroarenes with aryl diazonium salts. J Am Chem Soc. 2012;134(6):2958-2961. doi:10.1021/ja212099r.
Holden et al., Metal Free Bi(hetero)aryl Synthesis: A Benzyne Truce-Smiles Rearrangement. Angew Chem Int Ed Engl. 2016;55(7):2450-2453. doi:10.1002/anie.201510236.

(Continued)

*Primary Examiner* — Joseph R Kosack
(74) *Attorney, Agent, or Firm* — Wolf, Greenfield & Sacks, P.C.

(57) ABSTRACT

The present invention relates to a method for the metal-free preparation of a biaryl compound by a photosplicing reaction and its use in the preparation of chemical compounds, preferably of active ingredients e.g. in the fields of pharmaceuticals and agrochemicals. In particular, it refers to a method for the regiocontrolled preparation of a biaryl compound of formula (I): Ar—Ar' by photochemically reacting a precursor compound of formula (II): Ar—L—Ar' to form a biaryl compound of general formula: Ar—L—Ar'(II)→Ar—Ar' (I) wherein Ar and Ar', independently of each other, represent an unsubstituted or substituted C6-C20 aryl group or a heteroaryl group with 5-20 ring atoms selected from carbon, nitrogen, oxygen and sulfur, and L represents a group —X—Y—Z— as defined herein. The biaryl compounds are generally suitable as intermediates or key building blocks in a very broad spectrum of organic chemical syntheses and their respective utilities. Their use within the field of synthesis of active ingredients is an aspect of the invention, and their use in the preparation of pharmaceutically active ingredients is particularly preferred.

18 Claims, 2 Drawing Sheets

(56) References Cited

PUBLICATIONS

Horton et al., The combinatorial synthesis of bicyclic privileged structures or privileged substructures. Chem Rev. 2003;103(3):893-930. doi:10.1021/cr020033s.

Ito et al., Organocatalytic C—H/C—H' cross-biaryl coupling: C-selective arylation of sulfonanilides with aromatic hydrocarbons. J Am Chem Soc. 2013;135(38):14078-14081. doi:10.1021/ja407944p.

Johansson Seechurn et al., Palladium-catalyzed cross-coupling: a historical contextual perspective to the 2010 Nobel Prize. Angew Chem Int Ed Engl. 2012;51(21):5062-5085. doi:10.1002/anie.201107017.

Nacsa et al., Cross-coupling of sulfonic acid derivatives via aryl-radical transfer (ART) using TTMSS or photoredox. Org Chem Front. 2018;5:64-69. doi: 10.1039/C7Q000731K.

Nüllen et al., Synthesis of Cannabinol by a Modified Ullmann-Ziegler Cross-Coupling. Synlett. 2013;24(09):1109-1112. doi:10.1055/s-0033-1338428.

Pop, Cannabinoids, endogenous ligands and synthetic analogs. Curr Opin Chem Biol. 1999;3(4):418-425. doi:10.1016/S1367-5931(99)80062-3.

Rodriguez et al., Decarboxylative coupling reactions: a modern strategy for C-C-bond formation. Chem Soc Rev. 2011;40(10):5030-5048. doi:10.1039/c1cs15093f.

Shirakawa et al., Cross-coupling of aryl Grignard reagents with aryl iodides and bromides through S(RN)1 pathway. Angew Chem Int Ed Engl. 2012;51(1):218-221. doi:10.1002/anie.201106086.

Sun et al., Transition-metal-free coupling reactions. Chem Rev. 2014;114(18):9219-9280. doi:10.1021/cr400274j.

Sun et al., An efficient organocatalytic method for constructing biaryls through aromatic C—H activation. Nat Chem. 2010;2(12):1044-1049. doi:10.1038/nchem.862.

Trost et al, Synthesis of (-)-Delta9-trans-tetrahydrocannabinol: stereocontrol via Mo-catalyzed asymmetric allylic alkylation reaction. Org Lett. 2007;9(5):861-863. doi:10.1021/ol063022k.

Turner et al., Molecular Pharmacology of Phytocannabinoids. Prog Chem Org Nat Prod. 2017;103:61-101. doi:10.1007/978-3-319-45541-9_3.

Weiss et al., Photochemistry of sulfonamides and sulfonylureas: a contribution to the problem of light-induced dermatoses. Angew Chem Int Ed Engl. 1980;19(8):648-650. doi:10.1002/anie.198006481.

Welsch et al. Privileged scaffolds for library design and drug discovery. Curr Opin Chem Biol. 2010;14(3):347-361. doi:10.1016/j.cbpa.2010.02.018.

METHOD FOR THE METAL-FREE PREPARATION OF A BIARYL BY A PHOTOSPLICING REACTION AND THEIR USES

CROSS REFERENCE TO RELATED APPLICATIONS(S)

This Application is a National stage filing under 35 U.S.C. 371 of International Application No. PCT/EP2018/081727, filed Nov. 19, 2018, which claims priority to European Application No. 17202739.3, filed Nov. 21, 2017, each of which is herein incorporated by reference in their entirety.

TECHNICAL FIELD

The present invention relates to a method for the metal-free preparation of a biaryl compound by a photosplicing reaction and its use in the preparation of chemical compounds, preferably of active ingredients e.g. in the fields of pharmaceuticals and agrochemicals.

In the following the term "biaryl" will be used generically to mean a unit consisting of two aryl or heteroaryl groups, as defined herein, that are linked together via a single C—C-bond. The two aryl or heteroaryl groups can be the same or different. Thus, the term "biaryl" includes both bihomoaryl and biheteroaryl groups, wherein the respective aryl and heteroaryl units are either the same or different, and mixed aryl-heteroaryl units.

The biaryl compounds are generally suitable as intermediates or key building blocks in a very broad spectrum of organic chemical syntheses and their respective utilities. Their use within the field of synthesis of active ingredients is an aspect of the invention, and their use in the preparation of pharmaceutically active ingredients is particularly preferred.

BACKGROUND ART

Biaryl compounds are a class of industrially important molecules which can be produced by methods known in the art. Aryl coupling reactions provide one of the hot topics of modern organic syntheses due to the immense economic value of functional biaryls in different areas of chemistry. A large number of active pharmaceutical ingredients feature a substructure composed of two or more aromatic rings (biaryl), which is pivotal for the binding of the drug to the target.[1] The immense economic value of these pharmaceuticals and other functional biaryls has propelled the development of a vast array of synthetic methods, and the development of aryl cross-coupling methods has been in the core of chemical research for the past decades.[2,3,4]

Unarguably, aryl couplings using late transition metal catalysts such as copper, nickel and palladium have revolutionized synthetic chemistry, which is reflected by the Nobel Prize in Chemistry 2010 for palladium-catalyzed cross-couplings.[2] The huge success of this approach is based on the fact that the intermediary metal complex directs the regio- and chemoselective fusion of two aryl groups with high accuracy. However, catalytic aryl couplings generally require the use of stoichiometric amounts of expensive organometallic compounds, which require laborious synthesis and often handling under inert conditions is required. Although it is in many cases possible to replace the organometallic part with redox-active carboxy groups,[3,5] the coupling reactions involve harmful aryl halides and transition metals, which are scarce, expensive and often toxic.

These limitations, which are pertinent in the field of drug synthesis, have stimulated the development of a variety of metal-free biaryl syntheses.[6] Many protocols have been reported, some of which involve photolysis to generate radicals or aryl cations,[7,8,9] Grignard reagents,[10] Lewis-acid mediated oxidative coupling of electron-rich arenes,[11,12,13] and base-mediated coupling of aryl iodides.[14]

These conventional methods, however, may require harsh conditions and large excess of the cross-coupling partner, and produce regioisomeric mixtures as well as homocoupling products in some cases. Regioselective biaryl syntheses via intramolecular C—C bond formations and rearrangements have been developed,[15,16] but the linker or parts thereof remains in the product. Therefore, the currently available metal-free coupling methods cannot compete with the powerful metal-catalyzed cross-couplings in terms of chemo- and regioselectivity.

SUMMARY OF THE INVENTION

The present invention refers to a method for the regiocontrolled preparation of a biaryl compound of general formula (I) by photochemically reacting a precursor compound of general formula (II) to form a biaryl compound of general formula (I)

wherein

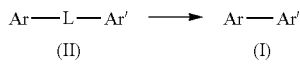

Ar and Ar', independently of each other, represent an unsubstituted or substituted $C_6$-$C_{20}$ aryl group or a heteroaryl group with 5-20 ring atoms selected from carbon, nitrogen, oxygen and sulfur, and L represents a group —X—Y—Z— wherein X, Y, Z are independently of each other selected from

X=$SO_2$, (P=O)$OR^1$, $SiR^2R^3$,

Y=$NR^4$, O, $CR^5R^6$,

Z=$CR^7R^8$, wherein $R^1$—$R^8$ are as defined herein below and wherein the photochemical reaction is performed under UV light in the range of 190-400 nm, preferably 254 nm.

DETAILED DESCRIPTION OF THE INVENTION

Figure 1:
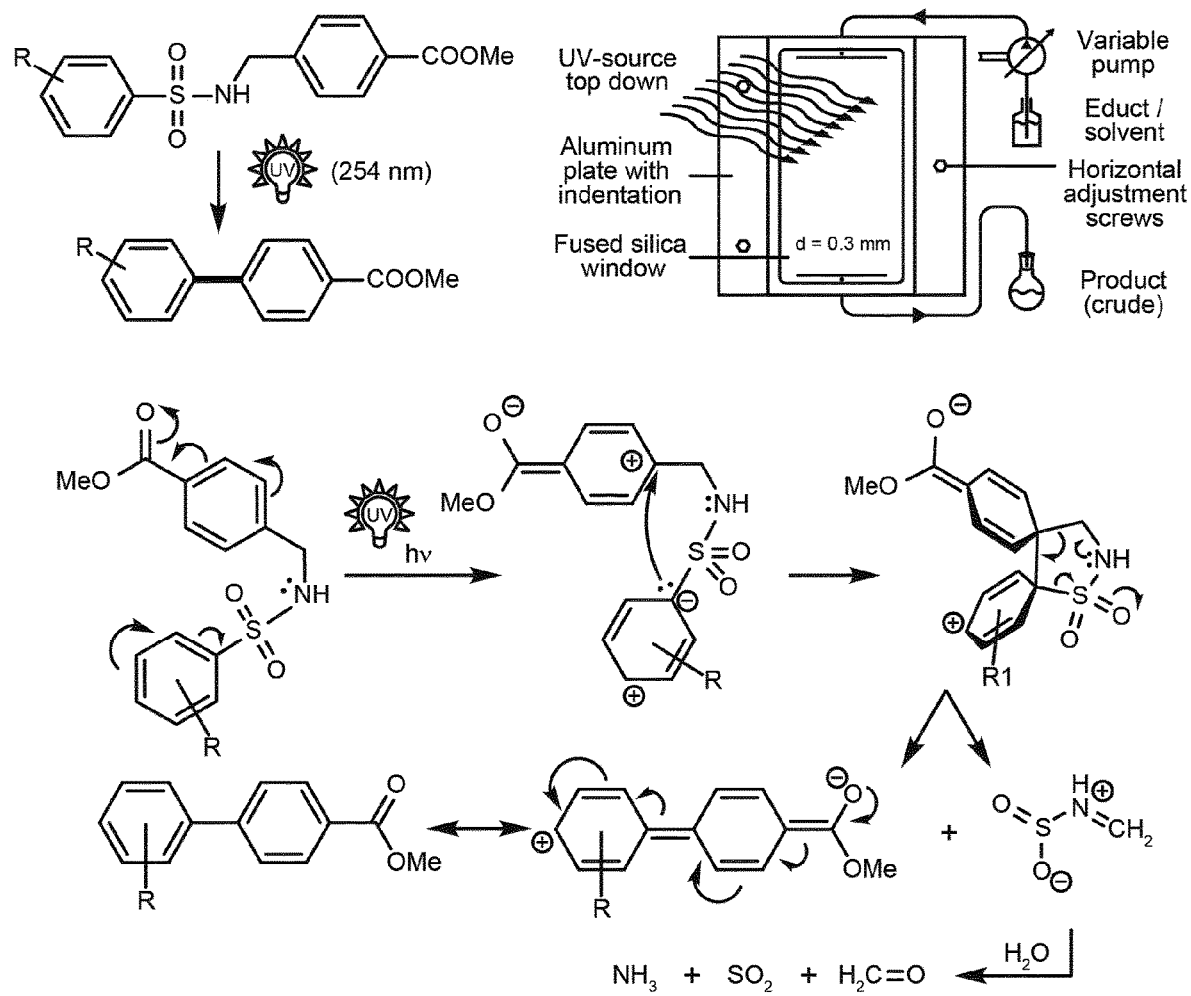
FIG. 1 provides an overview on a preferred general photosplicing reaction according to the present invention, an exemplary technical reactor design and the proposed reaction mechanism based on the experimental results described in more detail in the section "Elucidation of the Potential Reaction Mechanism" in the specification.

The present invention was attained in consideration of the aforementioned drawbacks of prior art methods, which are either expensive and/or laborious (in the case of metal-catalyzed cross-couplings) or limited in their scope and usefulness (metal-free synthesis methods).

The present invention provides a novel method overcoming both the drawbacks of conventional metal-catalyzed cross-couplings and the limitations of metal-free biaryl synthesis methods known so far.

This safe and convenient process, thus, provides an important improvement over the widely used known syntheses methods due to its high yields and its regioselectivity, the traceless cleavage of the linker used, and the avoidance of costly and toxic heavy metal catalysts.

This is achieved by the novel metal-free biaryl coupling reaction by a highly selective method termed photosplicing. This reaction involves the tethering of two aryl groups by a temporary, traceless (sulfonamide) linker, which directs the light-mediated aryl-fusion and regioselectively leads to a single and metal-free coupling product.

Specific embodiments for carrying out the present invention are described below.

[1] In a first embodiment the present invention refers to a method for the regiocontrolled preparation of a biaryl compound of general formula (I) by photochemically reacting a precursor compound of general formula (II) to form a biaryl compound of general formula (I)

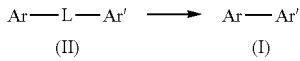

wherein

Ar and Ar', independently of each other, represent an unsubstituted or substituted $C_6$-$C_{20}$ aryl group or an unsubstituted or substituted heteroaryl group with 5-20 ring atoms selected from carbon, nitrogen, oxygen and sulfur, and wherein the carbon atom may be linked with oxygen or sulfur to form a C=O or a C=S group, and L represents a group —X—Y—Z— wherein X, Y, Z are independently of each other selected from

X=$SO_2$, (P=O)$OR^1$, $SiR^2R^3$,

Y=$NR^4$, O, $CR^5R^6$,

Z=$CR^7R^8$, wherein $R^1$ is hydrogen, an unsaturated or saturated, linear, branched or cyclic $C_1$-$C_{12}$ aliphatic radical, a phenyl or a benzyl group, each of which can be substituted by 1-5 same or different substituent(s), $R^2$, $R^3$ are independently of each other a $C_6$-$C_{20}$ aryl that can be substituted by 1-5 same or different substituents as defined herein below, a 5-20 membered heteroaryl comprising 1 to 5 same or different heteroatoms selected from N, O, S, (wherein a carbon atom may be bound to oxygen or sulfur to form a C=O or C=S group) that can be substituted by 1-5 same or different substituents as defined herein below, or an unsaturated or saturated, linear, branched or cyclic $C_1$-$C_{12}$ aliphatic radical that may be independently substituted by 1-5 same or different substituents as defined herein below, $R^4$ is a hydrogen, an unsaturated or saturated, linear, branched or cyclic $C_1$-$C_{12}$ aliphatic radical that can be substituted by 1-5 same or different substituents as defined herein below, a $C_6$-$C_{20}$ aryl group that can be substituted by 1-5 same or different substituents as defined herein below, a 5-20 membered heteroaryl comprising 1 to 5 same or different heteroatoms selected from N, O, S, (wherein a carbon atom may be bound to oxygen or sulfur to form a C=O or C=S group) that can be substituted by 1-5 same or different substituents as defined herein below, a linear or cyclic acyl group with up to 8 carbon atoms that may be substituted by 1-5 same or different substituents as defined herein below, an amino protective group as defined in Greene's Protective Groups in Organic Synthesis, 5$^{th}$ Edition or a $SO_2$—Ar group (with Ar being identical to Ar in formulae I/II) as defined herein below, $R^5$, $R^6$ are independently of each other hydrogen, a $C_6$-$C_{20}$ aryl group that can be substituted by 1-5 same or different substituents as defined herein below, a 5-20 membered heteroaryl comprising 1 to 5 same or different heteroatoms selected from N, O, S, (wherein a carbon atom may be bound to oxygen or sulfur to form a C=O or C=S group) that can be substituted by 1-5 same or different substituents as defined herein below, a linear or cyclic acyl group with up to 8 carbon atoms that can be substituted by 1-5 same or different substituents as defined herein below, or an unsaturated or saturated, linear, branched or cyclic $C_1$-$C_{12}$ aliphatic radical that may be substituted by 1-5 same or different substituents as defined herein below, $R^7$, $R^8$ are independently of each other hydrogen, a $C_6$-$C_{20}$ aryl group that can be substituted by 1-5 same or different substituents as defined herein below, a 5-20 membered heteroaryl comprising 1 to 5 same or different heteroatoms selected from N, O, S, (wherein a carbon atom may be bound to oxygen or sulfur to form a C=O or C=S group) that can be substituted by 1-5 same or different substituents as defined herein below, a linear or cyclic acyl group with up to 8 carbon atoms that can be substituted by 1-5 same or different substituents as defined herein below, or an unsaturated or saturated, linear, branched or cyclic $C_1$-$C_{12}$ aliphatic radical that may be independently substituted by 1-5 same or different substituents as defined herein below, and wherein the photochemical reaction is performed under UV light in the range of 190-400 nm, preferably 254 nm.

[2] In a second embodiment the present invention refers to a method for the regiocontrolled preparation of a biaryl compound of general formula (I) according to [1]

wherein

Ar and Ar', independently of each other, represent a $C_6$-$C_{20}$ aryl group or a 5-20 membered heteroaryl group, wherein the $C_6$-$C_{20}$ aryl group and the 5-20 membered heteroaryl group, independently of each other, can be substituted by one or more same or different substituent(s), and particularly 1 to 5 substituents, or 1 to 4 substituents, or 1 to 3 substituents, or 1-2 substituents, or a single substituent, independently selected from the group(s) consisting of a group —$OR^9$, a linear, branched or cyclic saturated or unsaturated aliphatic group, a branched, linear or cyclic saturated or unsaturated heteroaliphatic group, CN, F, Cl, a branched, linear or cyclic —(C=O)$R^{10}$ group, an aryl or heteroaryl group, a —$SR^{11}$, a group —($CR^{12}R^{13}$)$_{0-1}$$NR^{14}R^{15}$, a —B($OR^{16}$)$_2$, —$SnR^{17}R^{18}R^{19}$, —$N_3$, a —$COOR^{20}$ group, a —$CONR^{21}R^{22}$ group, a —$SO_2OR^{23}$ group, or a —$SO_2NR^{24}R^{25}$ group, wherein $R^9$ within the definition —$OR^9$ refers to a hydrogen, an unsaturated or saturated, linear, branched or cyclic $C_1$-$C_{12}$ aliphatic radical that may be independently substituted by one or more groups selected from an OH, $NH_2$, CN, F, Cl, carboxyalkyl group consisting of a straight or branched $C_1$-$C_6$ alkyl or a $C_3$-$C_6$ cycloalkyl, a $C_6$-$C_{20}$ aryl group or a 5-20 membered heteroaryl group, wherein each of the groups independently can be substituted as defined herein. $R^9$ can further be a branched, linear or cyclic —(C=O)$R^{10}$ group, a $C_6$-$C_{20}$ aryl group that can be substituted as defined herein, a 5-20-membered heteroaryl group that can be substituted as defined herein, or an alcohol protective group as defined in Greene's Protective Groups in Organic Synthesis, $5^{th}$ Edition, $R^{10}$ in the group (C=O)$R^{10}$ refers to a hydrogen, unsaturated or saturated, linear, branched or cyclic aliphatic radical having 1-8 carbon atoms that may be independently substituted by one or more groups selected from an OH, $NH_2$, CN, F, Cl, COOH, a $C_6$-$C_{20}$ aryl group, a 5-20 membered heteroaryl group or a carboxyalkyl group, wherein the alkyl radical consists of a straight or branched $C_1$-$C_6$ alkyl or a $C_3$-$C_6$ cycloalkyl, wherein each of the groups independently can be substituted as defined herein. $R^{10}$ can further be a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein each of the groups independently can be substituted as defined herein, $R^{11}$ in the group —$SR^{11}$ group denotes a hydrogen, unsaturated or saturated, linear, branched or cyclic aliphatic radical having 1-8 carbon atoms that may be independently substituted by one or more groups selected from an OH, $NH_2$, CN, F, Cl, carboxyalkyl group, wherein the alkyl radical consists of a straight or branched $C_1$-$C_6$ alkyl or a $C_3$-$C_6$ cycloalkyl, wherein each of the groups independently can be substituted as defined herein. $R^{11}$ can further be an $C_6$-$C_{20}$ aryl group, a 5-14 membered monocyclic or bicyclic heteroaryl group comprising 1 to 4 same or different heteroatoms or heteroatom groups selected from N, O, S, C=O or C=S, wherein each of the groups independently can be substituted as defined herein, or $R^{11}$ denotes a sulfur protective group as defined in Greene's Protective Groups in Organic Synthesis, $5^{th}$ Edition, $R^{14}$ and $R^{15}$ in the group —$(CR^{12}R^{13})_{0-1}$—$NR^{14}R^{15}$ independently of each other refer to hydrogen, an unsaturated or saturated, linear, branched or cyclic aliphatic radical having 1-8 carbon atoms that may be independently substituted by one or more groups selected from OH, $NH_2$, CN, F, Cl, or a carboxyalkyl group, wherein the alkyl radical consists of a straight or branched $C_1$-$C_6$ alkyl or a $C_3$-$C_6$ cycloalkyl, wherein each of the groups independently can be substituted as defined herein. $R^{14}$ and $R^{15}$ can further independently of each other be a branched, linear or cyclic $C_1$-$C_8$ acyl group, a $(SO_2)_{0-1}$-$C_6$-$C_{20}$ aryl group or a $(SO_2)_{0-1}$-5-14 membered monocyclic or bicyclic heteroaryl group comprising 1 to 4 same or different heteroatoms or heteroatom groups selected from N, O, S, C=O or C=S, wherein each of the groups independently can be substituted as defined herein, or an (amino) protective group as defined in Greene's Protective Groups in Organic Synthesis, $5^{th}$ Edition and $R^{12}$, $R^{13}$ are independently of each other hydrogen, a $C_6$-$C_{20}$ aryl group, a 5-14-membered monocyclic or bicyclic heteroaryl group comprising 1 to 4 same or different heteroatoms selected from N, O, S, C=O and C=S, a linear or cyclic $C_1$-$C_8$ acyl group, wherein each of the groups independently can be substituted as defined herein, or an unsaturated or saturated, linear, branched or cyclic aliphatic radical having 1 to 8 carbon atoms that may be independently substituted by an OH group, the substituents $R^{16}$ in the group $B(OR^{16})_2$ independently of each other refer to hydrogen or a saturated, linear, branched or cyclic aliphatic radical having 1-8 carbon atoms that may be independently substituted by one or more a OH group(s) or (alcohol) protecting group(s). Both residues may also be part of a single cyclic residue, such as in boronic acid protective groups group as defined in Greene's Protective Groups in Organic Synthesis, $5^{th}$ Edition, the substituents $R^{17}$, $R^{18}$, $R^{19}$ at the group $SnR^{17}R^{18}R^{19}$ independently of each other refer to an unsaturated or saturated, linear, branched or cyclic aliphatic radical having 1-8 carbon atoms, a $C_6$-$C_{20}$ aryl group, or a 5-14 membered monocyclic or bicyclic heteroaryl group comprising 1 to 4 same or different heteroatoms or heteroatom groups selected from N, O, S, C=O or C=S, wherein the $C_1$-$C_8$ aliphatic radical, the $C_6$-$C_{20}$ aryl group, the 5-14 membered heteroaryl group, in turn, can be substituted as defined herein, $R^{20}$ in the definition —$COOR^{20}$ represents hydrogen, an unsaturated or saturated, linear, branched or cyclic aliphatic radical having 1-8 carbon atoms that may be independently substituted by one or more groups selected from OH, $NH_2$, CN, Cl, F, a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, wherein the $C_6$-$C_{20}$ aryl group and the 5-14 membered heteroaryl group, in turn, can be substituted as defined herein or a carboxylic acid protective group as defined in Greene's Protective Groups in Organic Synthesis, $5^{th}$ Edition, $R^{21}$ and $R^{22}$ in the group —$CONR^{21}R^{22}$ independently of each other refer to hydrogen, an unsaturated or saturated, linear, branched or cyclic aliphatic radical having 1-8 carbon atoms that may be independently substituted by one or more groups selected from OH, $NH_2$, CN, F, Cl, a carboxyalkyl group, wherein the alkyl radical consists of a straight or branched $C_1$-$C_6$ alkyl or a $C_3$-$C_6$ cycloalkyl, a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_1$-$C_6$ alkyl group, the $C_3$-$C_6$ cycloalkyl group, the $C_6$-$C_{20}$ aryl group and the 5-14 membered heteroaryl group, in turn, can be substituted as defined herein or $R^{21}$, $R^{22}$ may further be selected from a $C_6$-$C_{20}$ aryl or a 5-14 membered monocyclic or bicyclic heteroaryl group comprising 1 to 4 same or different heteroatoms or heteroatom groups selected from N, O, S, C=O or C=S, wherein the $C_6$-$C_{20}$ aryl or the 5-14 membered heteroaryl group, in turn, can be substituted as defined herein below, $R^{23}$ within the definition of the group —$SO_2OR^{23}$ refers to a hydrogen atom, an unsaturated or saturated, linear, branched or cyclic aliphatic radical having 1-8 carbon atoms that may be independently substituted by one or more groups selected from OH, $NH_2$, CN, F, Cl, a carboxyalkyl group, wherein the alkyl radical consists of a straight or branched $C_1$-$C_6$ alkyl or a $C_3$-$C_6$ cycloalkyl, a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_1$-$C_6$ alkyl group, the $C_3$-$C_6$ cycloalkyl group, the $C_6$-$C_{20}$ aryl group and the 5-14-membered heteroaryl group, in turn, can be substituted as defined herein or $R^{23}$ can further be a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_6$-$C_{20}$ aryl or the 5-14 membered heteroaryl group, in turn, can be substituted as defined herein, $R^{24}$ and $R^{25}$ within the term —$SO_2NR^{24}R^{25}$ are independently of each other hydrogen, an unsaturated or saturated, linear, branched or cyclic aliphatic radical having 1-8 carbon atoms, a —$(CR^{12}R^{13})_{0-1}$-$C_6$-$C_{20}$-aryl or a —$(CR^{12}R^{13})_{0-1}$-5-14 membered monocyclic or bicyclic heteroaryl group comprising 1 to 4 same or different heteroatoms selected from N, O, S, C=O and C=S, a linear or cyclic $C_1$-$C_8$ acyl group, wherein the $C_1$-$C_8$ aliphatic radical, the $C_6$-$C_{20}$-aryl, the 5-14 membered heteroaryl group and the $C_1$-$C_8$ acyl group, in turn, can be substituted as defined herein, or $R^{24}$, $R^{25}$ refer to an amino protective group as defined in Greene's Protective Groups in Organic Synthesis, 5$^{th}$ Edition, and wherein $R^{12}$ and $R^{13}$ are independently of each other hydrogen, a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or an unsaturated or saturated, linear, branched or cyclic aliphatic radical having 1-8 carbon atoms that may be independently substituted by an OH group, L represents a group —X—Y—Z— wherein X, Y, Z are independently of each other selected from

X=$SO_2$, (P=O)$OR^1$, $SiR^2R^3$,
Y=$NR^4$, O, $CR^5R^6$,
Z=$CR^7R^8$ and $R^1$ is a hydrogen, an unsaturated or saturated, linear, branched or cyclic aliphatic radical having 1-8 carbon atoms that may be substituted as defined herein, a phenyl or a benzyl group, $R^2$, $R^3$ are independently of each other a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, a linear or cyclic acyl group or an unsaturated or saturated, linear, branched or cyclic aliphatic radical having 1-8 carbon atoms that may be independently substituted by an OH group, $R^4$ is a hydrogen, an unsaturated or saturated, linear, branched or cyclic aliphatic radical having 1-8 carbon atoms, an aryl group, a 5-14 membered monocyclic or bicyclic heteroaryl group comprising 1 to 4 same or different heteroatoms or heteroatom groups selected from N, O, S, C=O or C=S, a linear or cyclic acyl group or a $SO_2$—Ar group (with Ar being identical to Ar in formulae I/II).

$R^5$, $R^6$ are independently of each other hydrogen, a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or an unsaturated or saturated, linear, branched or cyclic aliphatic radical having 1-8 carbon atoms that may be independently substituted by an OH group, $R^7$, $R^8$ are independently of each other hydrogen, a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or an unsaturated or saturated, linear, branched or cyclic aliphatic radical having 1-8 carbon atoms that may be independently substituted by an OH group and wherein the photochemically driven reaction is performed in a solution of the respective precursor compound of formula (II) in a photo-reactor consisting of a light source (UV emissions in the range of 190-400 nm, preferably 254 nm) and a UV-transparent chamber or flow cell, or alternatively wherein the precursor compound of formula (II) is irradiated as a solvent-free thin-film on a solid support.

General Definitions

In the following, the meanings of the terms used in the present specification are described, and the present invention is explained in more detail.

As used herein and unless otherwise specified, the term aryl group refers to an aromatic hydrocarbon monocycle, or a fused bicyclic or polycyclic ring system having the well-known characteristics of aromaticity, wherein at least the ring directly attached to the linker L contains a sp$^2$-configuration of all ring atoms. In particular, the aryl group may contain 6 to 20 carbon atoms ($C_6$-$C_{20}$ aryl), or 6 to 12 carbon atoms ($C_6$-$C_{12}$ aryl), or 6 carbon atoms ($C_6$ aryl) as ring members. Fused bicyclic or polycyclic aryl groups may include an aryl ring (e.g. a phenyl ring) fused to another aryl ring, or fused to one or more saturated or partially unsaturated carbocyclic ring(s), e.g. a tetrahydronaphthyl group may be mentioned as an example.

Monocyclic or bicyclic 6-12-membered aromatic hydrocarbon groups ($C_6$-$C_{12}$ aryl) are preferred, and a phenyl group and a naphthyl group are mentioned as specific examples.

The heteroaryl group is an aromatic hydrocarbon monocycle, or a fused bicyclic or polycyclic ring system comprising up to 5, or 4, or 3, or 2, same or different, or at least one heteroatom or heterogroup independently selected from N, O, and S, C=O or C=S having the well-known characteristics of aromaticity, and wherein at least the ring directly attached to the linker L displays an sp$^2$-configuration of all ring atoms. In particular, heteroaryl groups contain 5 to 20 ring atoms (5-20-membered heteroaryl), or 5 to 14 ring atoms (5-14-membered heteroaryl) are preferred. Monocyclic and bicyclic 5- to 14-membered aromatic hydrocarbon groups comprise at least one heteroatom or one heterogroup independently selected from N, O, and S, C=O or C=S. The above definition includes bi- or polycyclic heteroaryl groups wherein at least one aromatic heteroaryl ring directly attached to the linker L is fused to one or more aryl or heterocycloalkyl ring(s).

Illustrative examples of monocyclic heteroaryl groups include the pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl group.

Illustrative examples of fused ring heteroaryl groups include: the benzofuranyl, coumaryl, isocoumaryl, benzothiophenyl, indolyl, benzimidazolyl, indazolyl, 1,2-benzodioxole, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyidinyl, pyrazolo[4,3-c]pyridinyl, pyrazolo[3,4-c]pyridinyl, pyrazolo[3,4-b]pyridinyl, isoindolyl, indazolyl, purinyl, indolininyl, imidazo[1,2-a]pyridinyl, imidazo[1,5-a]pyridinyl, pyrazolo[1,5-a]pyridinyl, pyrrolo[1-2,b]pyridazinyl, imidazo[1,2-c]pyrimidinyl, quinolinyl, isoquinolinyl, cinnolinyl, azaquinazolinyl, quinoxalinyl, phthalazinyl, 1,6-naphthyridinyl, 1J-naphthyridinyl, 1,8-naphthyridinyl, 1,5-naphthyridinyl, 2,6-naphthyridinyl, 2J-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl group.

Preferred are 5-14-membered monocylic or bicyclic heteroaryl groups comprising 1 to 4 same or different heteroatoms or heterogroups selected from N, O, and S, C=O or C=S. More preferred are heteroaryl groups, such as furanyl, imidazolyl, pyridyl, thiazolyl, thiophenyl, furanyl, pyrimidyl, pyrazinyl, benzothiazolyl, benzothiophenyl and indolyl. Particularly preferred are heteroaryls such as pyridyl, thiophenyl, benzothiophenyl, benzothiazolyl and indolyl.

The aryl and the heteroaryl group, independently of each other, can be substituted by one or more same or different substituent(s) selected from the group(s) consisting of one or more, and particularly 1 to 5 substituents, or 1 to 4 substituents, or 1 to 3 substituents, or 1-2 substituents, or a single substituent, independently selected from the group(s) consisting of a group —$OR^9$, a linear, branched or cyclic saturated or unsaturated aliphatic group, a branched, linear or cyclic saturated or unsaturated heteroaliphatic group, CN, F, Cl, a branched, linear or cyclic —(C=O)$R^{10}$ group, an aryl or heteroaryl group, a $SR^{11}$, an amino group —$(CR^{12}C^{13})_{0-1}$—$NR^{14}R^{15}$, a $B(OR^{16})_2$, $SnR^{17}R^{18}R^{19}$, $N_3$, a —$COOR^{20}$ group, a —$CONR^{21}R^{22}$ group, —$SO_2OR^{23}$, —$SO_2NR^{24}R^{25}$, wherein the substituents $R^9$—$R^{25}$ have the meanings as defined herein below. To the extent that the substitution(s) referred to above make(s) chemical sense, the substitution(s) can equally take place at a carbon or at a hetero ring atom of the heteroaryl group.

The term —$OR^9$ includes the hydroxyl group —OH and substituted —$OR^9$ groups, wherein $R^9$ refers to an unsaturated or saturated, linear, branched or cyclic aliphatic radical having 1-8 carbon atoms that may be substituted by one or more substituents, and particularly 1 to 5, or 1 to 4 substituents, or 1 to 3 substituents, or 1-2 substituents, or a single substituent, independently selected from the group(s) consisting of OH, $NH_2$, CN, F, Cl, a carboxyalkyl group consisting of a straight or branched $C_1$-$C_6$ alkyl or a $C_3$-$C_6$ cycloalkyl, an aryl or heteroaryl group, wherein the $C_1$-$C_6$ alkyl group, the $C_3$-$C_6$ cycloalkyl, the aryl group and the heteroaryl group can be substituted as defined herein. $R^1$ can further be a branched, linear or cyclic —(C=O)$R^{10}$ group, an aryl group, a 5-14 membered monocyclic or bicyclic heteroaryl group comprising 1 to 4 same or different heteroatoms or heteroatom groups selected from N, O, S, C=O or C=S, wherein the —(C=O)$R^{10}$ group, the aryl group and the 5-14 membered heteroaryl group can be substituted as defined herein, or an alcohol protecting group as defined in Greene's Protective Groups in Organic Synthesis, 5$^{th}$ Edition.

In a preferred embodiment $R^9$ refers to hydrogen, an unsaturated or saturated, linear, branched or cyclic aliphatic radical having 1-6 carbon atoms that may be substituted by 1 to 3 substituents, or 1-2 substituents, or a single substituent, independently selected from the group(s) consisting of OH, $NH_2$, CN, F, Cl, a carboxyalkyl group consisting of a straight or branched $C_1$-$C_6$ alkyl or a $C_3$-$C_6$ cycloalkyl, an $C_6$-$C_{12}$ aryl or a 5-14-membered heteroaryl group comprising 1 to 3 same or different heteroatoms selected from N, O, and S, wherein the $C_1$-$C_6$ alkyl or a $C_3$-$C_6$ cycloalkyl, an $C_6$-$C_{12}$ aryl or the 5-14 membered heteroaryl group can be substituted as defined herein. $R^9$ can further be a branched, linear or cyclic —(C=O)$R^{10}$ group, an $C_6$-$C_{12}$ aryl or a 5-14-membered heteroaryl group comprising 1 to 3 same or different heteroatoms selected from N, O, and S, wherein the —(C=O)$R^{10}$ group, an $C_6$-$C_{12}$ aryl group or the 5-14-membered heteroaryl group can be substituted as defined herein, or a trimethylsilyl group, a tert-butyldimethylsilyl group, a triethylsilyl group, a tert-butyl diphenylsilyl group, a benzoate group, a benzyl group, a methoxymethyl group, a tetrahydropyranyl group, a triphenylmethyl group, a chloro-triphenylmethyl group.

In a more preferred embodiment $R^9$ is hydrogen, unsubstituted methyl or ethyl, $CH_2OH$, $CH_2CH_2OH$, $CH_2NH_2$, $CH_2CH_2NH_2$, $CH_2CN$, $CH_2CH_2CN$, 1-fluoromethyl, difluoromethyl, trifluoro-methyl, 2-fluoroethyl, phenyl, pyridyl or a trimethylsilyl group, a tert-butyldimethylsilyl group, a triethylsilyl group, a tert-butyl diphenylsilyl group, a benzoate group, a benzyl group, a methoxymethyl group, a tetrahydropyranyl group, a triphenylmethyl group, a chloro-triphenylmethyl group.

The term —(C=O)$R^{10}$ group includes the aldehyde group —(C=O)H and acyl groups —(C=O)$R^{10}$ and $R^{10}$ refers to a hydrogen, an unsaturated or saturated, linear, branched or cyclic aliphatic radical having 1-8 carbon atoms that may be substituted by one or more substituents, and particularly 1 to 5, or 1 to 4 substituents, or 1 to 3 substituents, or 1-2 substituents, or a single substituent, independently selected from the group(s) of OH, $NH_2$, CN, F, Cl, COOH, a $C_6$-$C_{20}$ aryl, a 5-14-membered heteroaryl comprising 1 to 3 same or different heteroatoms selected from N, O, and S, or a carboxyalkyl, wherein the alkyl radical consists of a straight or branched $C_1$-$C_6$ alkyl or a $C_3$-$C_6$ cycloalkyl, wherein the $C_6$-$C_{20}$ aryl, the 5-14-membered heteroaryl, the $C_1$-$C_6$ alkyl and the $C_3$-$C_6$ cycloalkyl group can be substituted as defined herein. $R^{10}$ can further be an $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_6$-$C_{20}$ aryl group and the 5-14-membered heteroaryl group may be substituted as defined herein. The C=O group may further be modified as a carbonyl protective group as defined in Greene's Protective Groups in Organic Synthesis, 5$^{th}$ Edition.

In a preferred embodiment $R^{10}$ refers to hydrogen, an unsaturated or saturated, linear, branched or cyclic aliphatic radical having 1-6 carbon atoms that may be substituted by 1 to 3 substituents, or 1-2 substituents, or a single substituent, independently selected from the group(s) consisting of OH, $NH_2$, CN, F, Cl, COOH, a $C_6$-$C_{12}$ aryl, a 5-14-membered heteroaryl or carboxyalkyl consisting of a straight or branched $C_1$-$C_6$ alkyl or a $C_3$-$C_6$ cycloalkyl, wherein the $C_6$-$C_{12}$ aryl, the 5-14-membered heteroaryl, the $C_1$-$C_6$ alkyl and the $C_3$-$C_6$ cycloalkyl group may be substituted as described herein. $R^{10}$ can further be an $C_6$-$C_{12}$ aryl or a 5-14-membered heteroaryl group comprising 1 to 3 same or different heteroatoms or hetero groups selected from N, O, C=O, C=S, and S, wherein the $C_6$-$C_{12}$ aryl and the 5-14-membered heteroaryl group can be substituted as defined herein, or a thio-tert-butyl group. More preferred $R^{10}$ substituents are hydrogen, unsubstituted methyl or ethyl, $CH_2OH$, $CH_2CH_2OH$, $CH_2NH_2$, $CH_2CH_2NH_2$, $CH_2CN$, $CH_2CH_2CN$, 1-fluoromethyl, difluoromethyl, trifluoromethyl, 2-fluoroethyl, phenyl, pyridyl or a thio-tert-butyl group.

The term aliphatic group refers to a linear, branched or cyclic saturated or unsaturated non-aromatic group with 1 to 12 carbon atoms ($C_1$-$C_{12}$ aliphatic group), or 1 to 10 carbon atoms ($C_1$-$C_{10}$ aliphatic group), or 1 to 8 carbon atoms ($C_1$-$C_8$ aliphatic group), or 1 to 6 carbon atoms ($C_1$-$C_6$ aliphatic group). Aliphatic groups, in particular, include linear, branched or cyclic alkyl, alkenyl, alkynyl groups having the respective number of carbon atoms as defined herein.

The term alkyl group refers to a linear, branched or cyclic saturated hydrocarbon chain group having 1 to 12 carbon atoms ($C_1$-$C_{12}$ alkyl), or 1 to 10 carbon atoms ($C_1$-$C_{10}$ alkyl), or 1 to 8 carbon atoms ($C_1$-$C_8$ alkyl), or 1 to 6 carbon atoms ($C_1$-$C_6$ alkyl). Alkyl groups having 1 to 6 carbon atoms ($C_1$-$C_6$ alkyl) are preferred. Specific examples include methyl, ethyl, n-propyl, isopropyl, n-butyl, tert-butyl, 2-methyl-n-butyl, 3-methyl-n-butyl, n-pentyl, 2-methyl-n-pentyl, hexyl, 2-ethylbutyl. Methyl and ethyl are particularly preferred. Specific examples of the equally preferred $C_3$-$C_6$ cycloalkyl group include the cyclopropyl, cyclobutyl, cyclopentyl and cyclohexyl group.

The term alkenyl group refers to a linear, branched or cyclic hydrocarbon chain group having at least two carbon atoms and at least one carbon-carbon double bond. In particular, alkenyl groups have 2 to 12 carbon atoms ($C_2$-$C_{12}$ alkenyl), or 2 to 10 carbon atoms ($C_2$-$C_{10}$ alkenyl), or 2 to 8 carbon atoms ($C_2$-$C_8$ alkenyl). Alkenyl groups having 2 to 6 carbon atoms ($C_2$-$C_6$ alkenyl) are preferred. Specific examples include vinyl, 1-propenyl, 2-propenyl, 1-butenyl, 2-butenyl, 3-butenyl, n-pentenyl, 2-methyl-n-pentenyl, hexenyl and 4-methyl-3-pentenyl. Cycloalkenyl groups include the cyclopentenyl, cyclohexenyl or cyclohexenyl group.

The term alkynyl group refers to a linear, branched or cyclic hydrocarbon chain group having at least two carbon atoms and at least one carbon-carbon triple bond. In particular, alkynyl groups have 2 to 12 carbon atoms ($C_2$-$C_{12}$ alkynyl), or 2 to 10 carbon atoms ($C_2$-$C_{10}$ alkynyl), or 2 to 8 carbon atoms ($C_2$-$C_8$ alkynyl). Alkynyl groups having 2 to 6 carbon atoms ($C_2$-$C_6$ alkynyl) are preferred. Specific examples include ethynyl, 1-propynyl, 2-propynyl, 1-butynyl, 2-butynyl, 3-butynyl, pentynyl and hexynyl.

The aliphatic group, including specifically the alkyl, alkenyl and alkynyl group(s), in turn, can be substituted by one or more, in particular, by 1 to 5, or 1 to 4, or 1 to 3, or 1-2 same or different, or a single substituent(s) selected from the group(s) consisting of an F, Cl, Br, I, $N_3$, CN, $SR^{26}$, $C=O-R^{27}$, $COOR^{28}$, $OR^{29}$, $NR^{30}R^{31}$, $SiR^{32}R^{33}R^{34}$, wherein the substituents $R^{26}$—$R^{34}$ are defined as herein below.

The term heteroaliphatic group refers to a linear, branched or cyclic saturated or unsaturated non-aromatic group with 2 to 12 carbon atoms ($C_2$-$C_{12}$ heteroaliphatic group), or 2 to 10 carbon atoms ($C_2$-$C_{10}$ heteroaliphatic group), or 2 to 8 carbon atoms ($C_2$-$C_8$ heteroaliphatic group), or 2 to 6 carbon atoms ($C_2$-$C_6$ heteroaliphatic group), including at least one heteroatom selected from N, O, and S in the carbon chain. Heteroaliphatic groups, in particular, include linear, branched or cyclic heteroalkyl, heteroalkenyl, heteroalkynyl groups having the respective number of carbon atoms as defined herein.

In particular, the heteroaliphatic group contains 1 to 4 heteroatoms independently selected from N, O, and S in the carbon chain, or 1 to 3 heteroatoms independently selected from N, O, and S in the carbon chain, or 1-2 heteroatoms independently selected from N, O, and S in the carbon chain, or one heteroatom selected from N, O, and S.

A cyclic heteroaliphatic ring may be fused to one or more other heterocyclic or carbocyclic rings.

The term heteroalkyl group refers to a linear, branched or cyclic saturated hydrocarbon chain group having 2 to 12 carbon atom(s) ($C_2$-$C_{12}$ heteroalkyl), or having 2 to 10 carbon atoms ($C_2$-$C_{10}$ heteroalkyl), or 2 to 8 carbon atoms ($C_2$-$C_8$ heteroalkyl), one or more, particularly 1 to 3 of which have been replaced by a heteroatom independently selected from the group of a nitrogen, sulfur or oxygen atom. Preferred are heteroalkyl groups having 1 to 6 carbon atom(s) ($C_1$-$C_6$ heteroalkyl), with 1 or 2 carbons atoms independently substituted by a nitrogen, sulfur or oxygen atom or a C=O group. Examplary heteroalkyls include heteroalkylethers, secondary and tertiary heteroalkylamines, amides and heteroalkylsulfides. Exemplary cyclic heteroalkyl groups include oxirane, aziridine, thiirane, oxetane, azetidine, tetrahydrofuran, tetrahydrothiophene, pyrrolidine, 1,3-dioxolan, 1,3-dithiolane, tetrahydropyran, piperidin, 1,4-dioxane, piperaine, oxepane, azepane or thiepane.

The term heteroalkenyl group refers to a linear, branched or cyclic analogue of an alkenyl group having 2 to 12 carbon atom(s) ($C_2$-$C_{12}$ heteroalkenyl), or having 2 to 10 carbon atoms ($C_2$-$C_{10}$ heteroalkenyl), or 2 to 8 carbon atoms ($C_2$-$C_8$ heteroalkenyl), in which 1 or more carbon atoms are independently replaced by a heteroatom selected from the group consisting of a nitrogen, sulfur or oxygen atom or a C=O group. Preferred are heteroalkenyl groups having 2 to 6 carbon atoms ($C_2$-$C_6$ heteroalkenyl) in which 1 or more atoms are independently replaced by a heteroatom selected from the group consisting of a nitrogen, sulfur or oxygen atom.

The term heteroalkynyl group refers to a linear, branched or cyclic analogue of an alkynyl group having 2 to 12 carbon atoms ($C_2$-$C_{12}$ heteroalkynyl), or having 2 to 10 carbon atoms ($C_2$-$C_{10}$ heteroalkynyl), or 2 to 8 carbon atoms ($C_2$-$C_8$ heteroalkynyl), in which one or more carbon atoms are independently replaced by a heteroatom consisting of a nitrogen, sulfur or oxygen atom. Preferred are heteroalkynyl groups having 1 to 6 carbon atoms ($C_2$-$C_6$ heteroalkynyl) in which 1 or more atoms are independently replaced by a heteroatom selected from the group consisting of a nitrogen, sulfur or oxygen atom.

The heteroaliphatic group, including specifically the heteroalkyl, heteroalkenyl, heteroalkynyl group(s), in turn, can be substituted by one or more, in particular, by 1 to 5, or 1 to 4, or 1 to 3, or 1-2 same or different, or a single substituent(s) selected from the group(s) consisting of an F, Cl, $N_3$, CN, $SR^{26}$, $C=O-R^{27}$, $COOR^{28}$, $OR^{29}$, $NR^{30}R^{31}$, $SiR^{32}R^{33}R^{34}$, wherein the substituents $R^{26}$—$R^{34}$ are defined as herein below.

The term —$SR^{11}$ group, wherein $R^{11}$ is hydrogen, unsaturated or saturated, linear, branched or cyclic aliphatic radical having 1-8 carbon atoms that may be independently substituted by one or more substituents, and particularly 1 to 5, or 1 to 4 substituents, or 1 to 3 substituents, or 1-2 substituents, or a single substituent, independently selected from the group(s) of OH, $NH_2$, CN, F, Cl, or a carboxyalkyl group, wherein the alkyl radical consists of a straight or branched $C_1$-$C_6$ alkyl or a $C_3$-$C_6$ cycloalkyl, wherein the $C_1$-$C_6$ alkyl and the $C_3$-$C_6$ cycloalkyl can be substituted as defined herein. $R^{11}$ can further be an aryl group, a 5-14-membered monocyclic or bicyclic heteroaryl group comprising 1 to 4 same or different heteroatoms selected from N, O, and S, C=O or C=S, wherein the $C_6$-$C_{20}$ aryl group and the 5-14-membered heteroaryl group can be substituted as defined herein, or a sulfur protective group as defined in Greene's Protective Groups in Organic Synthesis, $5^{th}$ Edition.

In a preferred embodiment $R^{11}$ refers to hydrogen, an unsaturated or saturated, linear, branched or cyclic aliphatic radical having 1-6 carbon atoms that may be substituted by 1 to 3 substituents, or 1-2 substituents, or a single substituent, independently selected from the group(s) consisting of OH, $NH_2$, CN, F, Cl, a carboxyalkyl group consisting of a straight or branched $C_1$-$C_6$ alkyl or a $C_3$-$C_6$ cycloalkyl, wherein the $C_1$-$C_6$ alkyl and the $C_3$-$C_6$ cycloalkyl can be substituted as defined herein. $R^{11}$ can further be an $C_6$-$C_{12}$ aryl or a $C_5$-$C_{14}$ heteroaryl group comprising 1 to 4 same or different heteroatoms selected from N, O, C=O, C=S and S, wherein the $C_6$-$C_{20}$ aryl group and the 5-14-membered heteroaryl group can be substituted as defined herein, or a 2-methoxyisobutyryl group, an acetate group, a thioacetate group, a tert-butyl group or a benzyl group.

More preferred $R^{11}$ substituents are hydrogen, unsubstituted methyl or ethyl, $CH_2OH$, $CH_2CH_2OH$, $CH_2NH_2$, $CH_2CH_2NH_2$, $CH_2CN$, $CH_2CH_2CN$, 1-fluoromethyl, difluoromethyl, trifluoro-methyl, 2-fluoroethyl, phenyl, pyridyl or a 2-methoxyisobutyryl group, an acetate group, a thioacetate group, or a benzyl group.

The amino group —$(CR^{12}CR^{13})_{0-1}$—$NR^{14}R^{15}$ includes the unsubstituted amino group —$NH_2$, —$NHR^{15}$ and —$NR^{14}R^{15}$ group(s), in which $R^{14}$, $R^{15}$ independently of each other refer to hydrogen, an unsaturated or saturated, linear, branched or cyclic aliphatic radical having 1-8 carbon atoms that may be substituted by one or more substituents, and particularly 1 to 5 substituents, or 1 to 4 substituents, or 1 to 3 substituents, or 1-2 substituents, or a single substituent, independently selected from the group(s) of OH, $NH_2$, CN, F, Cl, or a carboxyalkyl group, wherein the alkyl radical consists of a straight or branched $C_1$-$C_6$ alkyl or a $C_3$-$C_6$ cycloalkyl, wherein the $C_1$-$C_6$ alkyl group and the $C_3$-$C_6$ cycloalkyl group can be substituted as defined herein. $R^{14}$, $R^{15}$ can further independently of each other be a branched, linear or cyclic $C_1$-$C_8$ acyl group, a $(SO_2)_{0-1}$-$C_6$-$C_{20}$ aryl group, a $(SO_2)_{0-1}$-5-14-membered heteroaryl group comprising 1 to 4 same or different heteroatoms selected from N, O, C=O, C=S and S, wherein the $C_1$-$C_8$ acyl group, the $C_6$-$C_{20}$ aryl group and the 5-14-membered heteroaryl group can be substituted as defined herein, or an amino protective group as defined in Greene's Protective Groups in Organic Synthesis, $5^{th}$ Edition, and $R^{12}R^{13}$ are independently of each other hydrogen, a $C_6$-$C_{20}$ aryl group or a 5-14-membered heteroaryl group comprising 1 to 4 same or different heteroatoms selected from N, O, C=O, C=S and S, a linear or cyclic $C_1$-$C_8$ acyl group or an unsaturated or saturated linear, branched or cyclic aliphatic radical having 1-8 carbon atoms that may be independently substituted with an OH-group.

In a preferred embodiment $R^{14}$ and $R^{15}$ independently of each other refer to hydrogen, an unsaturated or saturated, linear, branched or cyclic aliphatic radical having 1-6 carbon atoms that may be substituted by 1 to 3 substituents, or 1-2 substituents, or a single substituent, independently selected from the group(s) consisting of OH, $NH_2$, CN, F, Cl, a carboxyalkyl group consisting of a straight or branched $C_1$-$C_6$ alkyl or a $C_3$-$C_6$ cycloalkyl, wherein the $C_1$-$C_6$ alkyl and the $C_3$-$C_6$ cycloalkyl group can be substituted as defined herein. $R^{14}$ and $R^{15}$ can further be a branched, linear or cyclic $C_1$-$C_8$ acyl group, a $(SO_2)_{0-1}$-$C_6$-$C_{12}$ aryl group or a $(SO_2)_{0-1}$-$C_5$-$C_{14}$ heteroaryl group comprising 1 to 4 same or different heteroatoms or heterogroups selected from N, O, C=O, C=S and S, wherein the $C_1$-$C_8$ acyl group, the $C_6$-$C_{12}$ aryl group and the $C_5$-$C_{14}$ heteroaryl group can be substituted as defined herein, or a toluensulfonyl group, a tert-butoxycarbonyl group, a benzyloxycarbonyl group, a benzyl group, a fluorenylmethyloxycarbonyl group, a phthalate group (as phthalimide), a trifluoroacetate group, a triphenylmethyl group.

More preferred $R^{14}$, $R^{15}$ substituents are hydrogen, unsubstituted methyl or ethyl, $CH_2OH$, $CH_2CH_2OH$, $CH_2NH_2$, $CH_2CH_2NH_2$, $CH_2CN$, $CH_2CH_2CN$, 1-fluoromethyl, difluoromethyl, trifluoro-methyl, 2-fluoroethyl, phenyl, pyridyl or a toluensulfonyl group, a tert-butoxycarbonyl group, a benzyloxycarbonyl group, a benzyl group, a fluorenylmethyloxycarbonyl group, a phthalate group (as phthalimide), a trifluoroacetate group, a triphenylmethyl group.

The group —$B(OR^{16})_2$ represents a boronic acid derivative, wherein the two substituents $R^{16}$ are independently of each other hydrogen, an unsaturated or saturated, linear, branched or cyclic aliphatic radical having 1-8 carbon atoms that may be substituted by one or more substituents, and particularly 1 to 5, or 1 to 4, or 1 to 3, or 1-2, or a single OH group. Both residues may also be part of a single cyclic residue, such as in boronic acid protective groups as defined in Greene's Protective Groups in Organic Synthesis, $5^{th}$ Edition.

In a preferred embodiment the two substituents $R^{16}$ are independently of each other hydrogen, an unsaturated or saturated, linear, branched or cyclic aliphatic radical having 1-6 carbon atoms that may be substituted by 1 to 3, or 1-2, or a single OH group or a pinacolyl ester protective group.

More preferred $R^{16}$ substituents are hydrogen, unsubstituted methyl or ethyl, $CH_2OH$, $CH_2CH_2OH$ or a pinacolyl ester protective group.

The group $SnR^{17}R^{18}R^{19}$ refers to a group containing a tin radical wherein, $R^{17}$—$R^{19}$ are independently of each other an unsaturated or saturated, linear, branched or cyclic aliphatic radical having 1-8 carbon atoms, an $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_1$-$C_8$ aliphatic radical, the $C_6$-$C_{20}$ aryl group and the 5-14-membered heteroaryl group can be substituted as defined herein.

In a preferred embodiment $R^{17}$—$R^{19}$ are independently of each other hydrogen, an unsaturated or saturated, linear, branched or cyclic aliphatic radical having 1-6 carbon atoms, a $C_6$-$C_{12}$ aryl group or a 5-14-membered heteroaryl group comprising 1 to 4 same or different heteroatoms or heterogroups selected from N, O, C=O, C=S, and S, wherein the $C_1$-$C_6$ aliphatic radical, the $C_6$-$C_{12}$ aryl group and the 5-14-membered heteroaryl group can be substituted as defined herein. More preferred are the methyl, ethyl, n-butyl group.

The group —$COOR^{20}$ refers to the carboxylic acid group —COOH, or to a carboxyester group —$COOR^{20}$, wherein $R^{20}$ represents an unsaturated or saturated, linear, branched or cyclic aliphatic radical having 1-8 carbon atoms that may be substituted by one or more substituents, and particularly 1 to 5 substituents, or 1 to 4 substituents, or 1 to 3 substituents, or 1-2 substituents, or a single substituent, independently selected from the group(s) of OH, $NH_2$, CN, Cl, F, $C_6$-$C_{20}$ aryl or a 5-14 membered heteroaryl comprising 1 to 4 same or different heteroatoms selected from N, O, C=O, C=S, and S, wherein the $C_6$-$C_{20}$ aryl and the 5-14 membered heteroaryl group can be substituted as defined herein, or a carboxylic acid protective group as defined in Greene's Protective Groups in Organic Synthesis, $5^{th}$ Edition.

In a preferred embodiment $R^{20}$ refers to hydrogen, an unsaturated or saturated, linear, branched or cyclic aliphatic radical having 1-6 carbon atoms that may be substituted by 1 to 3, or 1-2, or a single substituent, independently selected from the group(s) of OH, $NH_2$, CN, Cl, F, a $C_6$-$C_{12}$ aryl group or a 5-14-membered heteroaryl group comprising 1 to 4 same or different heteroatoms or heterogroups selected from N, O, C=O, C=S and S, wherein the $C_6$-$C_{12}$ aryl group and the 5-14-membered heteroaryl group can be substituted as defined herein. More preferred $R^{20}$ substituents are hydrogen, unsubstituted methyl or ethyl, $CH_2OH$, $CH_2CH_2OH$, $CH_2NH_2$, $CH_2CH_2NH_2$, $CH_2CN$, $CH_2CH_2CN$, fluoromethyl, difluoromethyl, trifluoromethyl, 2-fluoroethyl, phenyl, pyridyl, benzyl, tert-butyl.

The group —$CONR^{21}R^{22}$ includes the unsubstituted carbamide group —$C(=O)NH_2$ and, furthermore, includes both mono- (—$C(=O)NHR^{17}$) and di-substitued carbamide groups —CONR$^{21}$R$^{22}$, wherein R$^{21}$, R$^{22}$ independently of each other refer to hydrogen, an unsaturated or saturated, linear, branched or cyclic aliphatic radical having 1-8 carbon atoms that may be substituted by one or more substituents, and particularly 1 to 5 substituents, or 1 to 4 substituents, or 1 to 3 substituents, or 1-2 substituents, or a single substituent, independently selected from the group(s) of OH, NH$_2$, CN, F, Cl, COOH, an C$_6$-C$_{20}$ aryl or a 5-14-membered heteroaryl comprising 1 to 4 same or different heteroatoms selected from N, O, C═O, C═S and S, or a carboxyalkyl group, wherein the alkyl radical consists of a straight or branched C$_1$-C$_6$ alkyl or a C$_3$-C$_6$ cycloalkyl, wherein the C$_6$-C$_{20}$ aryl, the 5-14-membered heteroaryl, the C$_1$-C$_6$ alkyl and the C$_3$-C$_6$ cycloalkyl group can be substituted as defined herein. R$^{21}$, R$^{22}$ may further be selected from an C$_6$-C$_{20}$ aryl group, a 5-14-membered heteroaryl group comprising 1 to 4 same or different heteroatoms or heterogroups selected from N, O, C═O, C═S and S, wherein the C$_6$-C$_{20}$ aryl group and the 5-14-membered heteroaryl group can be substituted as defined herein, or an amide protective group as defined in Greene's Protective Groups in Organic Synthesis, 5$^{th}$ Edition.

In a preferred embodiment R$^{21}$, R$^{22}$ independently of each other refer to hydrogen, an unsaturated or saturated, linear, branched or cyclic aliphatic radical having 1-6 carbon atoms that may be substituted by 1 to 3, or 1-2, or a single substituent, independently selected from the group(s) of OH, NH$_2$, CN, Cl, F, COOH, a C$_6$-C$_{12}$ aryl or a 5-14-membered heteroaryl comprising 1 to 3 same or different heteroatoms selected from N, O, S, C═O and C═S or a carboxyalkyl group, wherein the alkyl radical consists of a straight or branched C$_1$-C$_6$ alkyl or a C$_3$-C$_6$ cycloalkyl, wherein the C$_6$-C$_{12}$ aryl, the 5-14-membered heteroaryl group, the C$_1$-C$_6$ alkyl and the C$_3$-C$_6$ cycloalkyl group can be substituted as defined herein. R$^{21}$, R$^{22}$ may further be selected from a C$_6$-C$_{12}$ aryl group or a 5-14-membered heteroaryl group comprising 1 to 3 same or different heteroatoms selected from N, O, S, C═O and C═S, a linear or cyclic C$_1$-C$_8$ acyl group, wherein the C$_6$-C$_{20}$ aryl, the 5-14-membered heteroaryl group and the C$_1$-C$_8$ acyl group can be substituted as defined herein, or a toluenesulfonyl group or a triphenylmethyl group.

More preferred substituents R$^{21}$, R$^{22}$ independently of each other are hydrogen, unsubstituted methyl or ethyl, CH$_2$OH, CH$_2$CH$_2$OH, CH$_2$NH$_2$, CH$_2$CH$_2$NH$_2$, CH$_2$CN, CH$_2$CH$_2$CN, fluoromethyl, difluoromethyl, 2-fluoroethyl, trifluoromethyl. R$^{21}$, R$^{22}$ may further be independently selected from phenyl, pyridyl, a toluenesulfonyl group or a triphenylmethyl group.

Within group —SO$_2$OR$^{23}$ the substituent

R$^{23}$ refers to a hydrogen atom, an unsaturated or saturated, linear, branched or cyclic aliphatic radical having 1-8 carbon atoms that may be substituted by one or more substituents, and particularly 1 to 5 substituents, or 1 to 4 substituents, or 1 to 3 substituents, or 1-2 substituents, or a single substituent, independently selected from the group(s) of OH, NH$_2$, CN, F, Cl, COOH, a C$_6$-C$_{20}$ aryl, a 5-14-membered heteroaryl comprising 1 to 3 same or different heteroatoms selected from N, O, S, C═O and C═S, or a carboxyalkyl group, wherein the alkyl radical consists of a straight or branched C$_1$-C$_6$ alkyl or a C$_3$-C$_6$ cycloalkyl, wherein the C$_6$-C$_{20}$ aryl, the 5-14-membered heteroaryl, the C$_1$-C$_6$ alkyl and the C$_3$-C$_6$ cycloalkyl group can be substituted as defined herein.

R$^{23}$ can further be a C$_6$-C$_{20}$ aryl or a 5-14-membered heteroaryl comprising 1 to 3 same or different heteroatoms selected from N, O, S, C═O and C═S, wherein the C$_6$-C$_{20}$ aryl and the 5-14-membered heteroaryl group can be substituted as defined herein.

In a preferred embodiment R$^{23}$ refers to a hydrogen atom, an unsaturated or saturated, linear, branched or cyclic aliphatic radical having 1-6 carbon atoms that may be substituted by 1 to 3, or 1-2, or a single substituent, independently selected from the group(s) of OH, NH$_2$, CN, F, Cl, COOH, a C$_6$-C$_{12}$ aryl group or a 5-14-membered heteroaryl group comprising 1 to 4 same or different heteroatoms selected from N, O, S, C═O and C═S, or a carboxyalkyl group, wherein the alkyl radical consists of a straight or branched C$_1$-C$_6$ alkyl or a C$_3$-C$_6$ cycloalkyl, wherein the C$_6$-C$_{12}$ aryl group, the 5-14-membered heteroaryl group, the C$_1$-C$_6$ alkyl and the C$_3$-C$_6$ cycloalkyl group can be substituted as defined herein. R$^{23}$ can further be a C$_6$-C$_{12}$ aryl group or a 5-14-membered heteroaryl group comprising 1 to 4 same or different heteroatoms selected from N, O, S, C═O and C═S, wherein the C$_6$-C$_{12}$ aryl group and the 5-14-membered heteroaryl group can be substituted as defined herein.

More preferred R$^{23}$ substituents are hydrogen, unsubstituted methyl or ethyl, CH$_2$OH, CH$_2$CH$_2$OH, CH$_2$NH$_2$, CH$_2$CH$_2$NH$_2$, CH$_2$CN, CH$_2$CH$_2$CN, 1-fluoromethyl, difluoromethyl, trifluoro-methyl, 2-fluoroethyl, phenyl or the pyridyl group.

The term —SO$_2$NR$^{24}$R$^{25}$ represents a sulfonamide group and includes the unsubstituted sulfonamide group —SO$_2$—NH$_2$, —SO$_2$—NHR$^{25}$ and —SO$_2$—NR$^{24}$R$^{25}$ group(s), in which R$^{24}$, R$^{25}$ are independently of each other hydrogen, an unsaturated or saturated, linear, branched or cyclic aliphatic radical having 1-8 carbon atoms, a —(CR$^{12}$R$^{13}$)$_{0-1}$-C$_6$-C$_{20}$ aryl group, a —(CR$^{12}$CR$^{13}$)$_{0-1}$-5-14 membered monocyclic or bicyclic heteroaryl group comprising 1 to 4 same or different heteroatoms selected from N, O, S, C═O and C═S, a linear or cyclic C$_1$-C$_8$ acyl group, wherein the C$_6$-C$_{20}$ aryl group, the 5-14 membered heteroaryl group and the C$_1$-C$_8$ acyl group can be substituted as defined herein, or an amino protective group as defined in Greene's Protective Groups in Organic Synthesis, 5$^{th}$ Edition, wherein R$^{12}$ and R$^{13}$ are independently of each other hydrogen, methyl, ethyl, a C$_6$-C$_{20}$ aryl group, a 5-14 membered monocyclic or bicyclic heteroaryl group comprising 1 to 4 same or different heteroatoms selected from N, O, S, C═O and C═S, a linear or cyclic C$_1$-C$_8$ acyl group or an unsaturated or saturated, linear, branched or cyclic aliphatic radical having 1-8 carbon atoms that may be independently substituted by an OH group.

In a preferred embodiment R$^{24}$, R$^{25}$ are independently of each other hydrogen, an unsaturated or saturated, linear, branched or cyclic aliphatic radical having 1-6 carbon atoms, a —(CR$^{12}$R$^{13}$)$_{0-1}$-C$_6$-C$_{12}$ aryl group or a —(CR$^{12}$CR$^{13}$)$_{0-1}$-5-14-membered heteroaryl group comprising 1 to 3 same or different heteroatoms selected from N, O, S, C═O and C═S, wherein the C$_1$-C$_6$ aliphatic radical, the C$_6$-C$_{12}$ aryl group, the 5-14-membered heteroaryl group can be substituted as defined herein, wherein R$^{12}$, R$^{13}$ are independently of each other hydrogen, methyl, ethyl, an C$_6$-C$_{12}$ aryl or a 5-14 membered monocyclic or bicyclic heteroaryl comprising 1 to 3 same or different heteroatoms selected from N, O, S, C═O and C═S, a linear or cyclic acyl group or an unsaturated or saturated, linear, branched or cyclic aliphatic radical having 1-6 carbon atoms that may be independently substituted by an OH group. More preferred R$^{24}$, R$^{25}$ are independently of each other hydrogen, methyl, ethyl, phenyl, pyridyl, a toluenesulfonyl group or a —(CR$^{12}$R$^{13}$)$_{0-1}$-C$_6$-C$_{12}$ aryl or —(CR$^{12}$R$^{13}$)$_{0-1}$-5-14-membered heteroaryl group, wherein R$^{12}$, R$^{13}$ are hydrogen, methyl or ethyl.

The term protective group used herein has the ordinary meaning generally accepted in the art and as published in the widely accepted standard text book Greene's Protective Groups in Organic Chemistry 5$^{th}$ Edition, John Wiley and Sons (2014).

The definition of a protective group as used herein, in particular, includes alcohol, amino, carbonyl carboxylic acid, phosphate, boron and sulfur protective groups.

The term alcohol (—OR) protective group, in particular, includes the methoxymethyl group, β-methoxyethoxymethyl group, tetrahydropyranyl group, tert-butyl group, allyl group, benzyl group, triphenylmethyl group, trimethylsilyl group, tert-butyldimethylsilyl group, triethylsilyl group, tert-butyldiphenylsilyl group, chloro-triphenylmethyl group, an acetic acid ester group, pivalic acid ester group or a benzoate group.

The term amino protective group, in particular, includes the 9-fluorenylmethyloxycarbonyl group, tert-butoxycarbonyl group, benzyloxycarbonyl group, a benzyl group, acetate group, trifluroacetate group, triphenylmethyl (trityl) group, a phthalyl group (as phthalimide), p-toluenesulfonyl group.

The term sulfur protective group, in particular includes the 2-methoxyisobutyryl group, the acetate group, the thioacetate group, the benzyl group or the tert-butyl group.

The term carbonyl protective group, in particular, includes the dimethylacetals, 1,3-dioxane, 1,3-dioxolane, 1,3 dithianes or 1,3 dithiolanes.

The term boron protective group, in particular includes pinacolyl ester groups.

The term carboxylic acid protective group in particular includes the methyl group, tert-butyl group, benzyl group or the thio-tert-butyl group.

As described above the aliphatic and heteroaliphatic group(s), in turn, can be substituted by one or more, in particular, by 1 to 5, or 1 to 4, or 1 to 3, or 1-2 same or different, or a single substituent(s) selected from the group(s) consisting of an F, Cl, N$_3$, CN, SR$^{26}$, (C=O)—R$^{27}$, COOR$^{28}$, OR$^{29}$, NR$^{30}$R$^{31}$, SiR$^{32}$R$^{33}$R$^{34}$, wherein R$^{26}$ refers to hydrogen, unsaturated or saturated, linear, branched or cyclic aliphatic radical having 1-8 carbon atoms that may be independently substituted by 1 to 3 substituents selected from the group consisting of OH, NH$_2$, CN, F, Cl, a carboxyalkyl group, wherein the alkyl radical consists of a straight or branched C$_1$-C$_6$ alkyl or a C$_3$-C$_6$ cycloalkyl, a phenyl group, a pyridyl group. R$^{26}$ can further be a phenyl group, a pyridyl group or a sulfur protective group as defined in Greene's Protective Groups in Organic Synthesis, 5$^{th}$ Edition.

In a preferred embodiment R$^{26}$ refers to hydrogen, an unsaturated or saturated, linear, branched or cyclic aliphatic radical having 1-6 carbon atoms, that may be independently substituted by 1 to 3 substituents selected from the group consisting of OH, NH$_2$, CN, F, Cl, COOH, a phenyl group, a pyridyl group or a carboxyalkyl group, wherein the alkyl radical consists of a straight or branched C$_1$-C$_6$ alkyl or a C$_3$-C$_6$ cycloalkyl. R$^{26}$ can preferably further be a phenyl group, a pyridyl group or a 2-methoxyisobutyryl group, an acetate group, a thioacetate group, a tert-butyl or a benzyl group.

More preferably, R$^{26}$ refers to hydrogen, methyl or ethyl, CH$_2$OH, CH$_2$CH$_2$OH, CH$_2$NH$_2$, CH$_2$CH$_2$NH$_2$, CH$_2$CN, CH$_2$CH$_2$CN, 1-fluoromethyl, difluoromethyl, trifluoromethyl, 2-fluoroethyl, phenyl, pyridyl or a 2-methoxyisobutyryl group, an acetate group, a tert-butyl, a thioacetate group or a benzyl group.

R$^{27}$ refers to hydrogen, unsaturated or saturated, linear, branched or cyclic aliphatic radical having 1-8 carbon atoms that may be independently substituted by 1 to 3 substituents selected from the group consisting of a OH, NH$_2$, CN, F, Cl, COOH, a phenyl, pyridyl group or a carboxyalkyl group, wherein the alkyl radical consists of a straight or branched C$_1$-C$_6$ alkyl or a C$_3$-C$_6$ cycloalkyl. R$^{27}$ can further be a phenyl, a pyridyl group, a thiol or a thio-tert-butyl group.

In a preferred embodiment R$^{27}$ refers to hydrogen, an unsaturated or saturated, linear, branched or cyclic aliphatic radical having 1-6 carbon atoms, that may be independently substituted by 1 to 3 substituents selected from the group consisting of OH, NH$_2$, CN, F, Cl, COOH, a phenyl or pyridyl group or a carboxyalkyl group, wherein the alkyl radical consists of a straight or branched C$_1$-C$_6$ alkyl or a C$_3$-C$_6$ cycloalkyl. R$^{27}$ can further be a phenyl, a pyridyl group, a thiol or a thio-tert-butyl group.

More preferably, R$^{27}$ refers to hydrogen, methyl or ethyl, CH$_2$OH, CH$_2$CH$_2$OH, CH$_2$NH$_2$, CH$_2$CH$_2$NH$_2$, CH$_2$CN, CH$_2$CH$_2$CN, 1-fluoromethyl, difluoromethyl, trifluoromethyl, 2-fluoroethyl, phenyl or pyridyl. R$^{27}$ can further be a phenyl, a pyridyl group or a thio-tert-butyl group.

R$^{28}$ is hydrogen, an unsaturated or saturated, linear, branched or cyclic aliphatic radical having 1-8 carbon atoms that may be independently substituted by 1 to 3 substituents selected from the group consisting of a OH, NH$_2$, CN, F, Cl, COOH, an aryl group, a 5-14-membered monocyclic or bicyclic heteroaryl group comprising 1 to 4 same or different heteroatoms selected from N, O, S, C=O and C=S, or a carboxyalkyl group, wherein the alkyl radical consists of a straight or branched C$_1$-C$_6$ alkyl or a C$_3$-C$_6$ cycloalkyl. R$^{28}$ can further be a phenyl, a pyridyl or a carboxylic acid protective group as defined in Greene's Protective Groups in Organic Synthesis, 5$^{th}$ Edition.

In a preferred embodiment R$^{28}$ refers to hydrogen, an unsaturated or saturated, linear, branched or cyclic aliphatic radical having 1-6 carbon atoms, that may be independently substituted by 1 to 3 substituents selected from the group consisting of OH, NH$_2$, CN, F, Cl, COOH, a C$_6$-C$_{12}$ aryl group or a C$_5$-C$_{14}$ heteroaryl group comprising 1 to 3 same or different heteroatoms selected from N, O, S, C=O and C=S or a carboxyalkyl group, wherein the alkyl radical consists of a straight or branched C$_1$-C$_6$ alkyl or a C$_3$-C$_6$ cycloalkyl. R$^{28}$ can further be a phenyl, a pyridyl or a benzyl group.

More preferably, R$^{28}$ refers to hydrogen, methyl or ethyl, CH$_2$OH, CH$_2$CH$_2$OH, CH$_2$NH$_2$, CH$_2$CH$_2$NH$_2$, CH$_2$CN, CH$_2$CH$_2$CN, 1-fluoromethyl, difluoromethyl, trifluoromethyl, 2-fluoroethyl, phenyl or pyridyl or a benzyl group.

R$^{29}$ is hydrogen, an unsaturated or saturated, linear, branched or cyclic aliphatic radical having 1-8 carbon atoms that may be independently substituted by 1 to 3 substituents selected from the group consisting of OH, NH$_2$, CN, F, Cl, COOH, a phenyl or pyridyl group or a carboxyalkyl group, wherein the alkyl radical consists of a straight or branched C$_1$-C$_6$ alkyl or a C$_3$-C$_6$ cycloalkyl. R$^{29}$ can further be a branched, linear or cyclic acyl group, a phenyl group, or an alcohol protective group as defined in Greene's Protective Groups in Organic Synthesis, 5$^{th}$ Edition.

In a preferred embodiment R$^{29}$ refers to hydrogen, an unsaturated or saturated, linear, branched or cyclic aliphatic radical having 1-6 carbon atoms, that may be independently substituted by 1 to 3 substituents selected from the group consisting of OH, NH$_2$, CN, F, Cl, COOH, a phenyl or pyridyl group or a carboxyalkyl group, wherein the alkyl radical consists of a straight or branched $C_1$-$C_6$ alkyl or a $C_3$-$C_6$ cycloalkyl. $R^{29}$ can further be a branched, linear or cyclic acyl group, a phenyl group, or a trimethylsilyl group, a tert-butyldimethylsilyl group, a triethylsilyl group, a tert-butyl diphenylsilyl group, a benzoate group, a benzyl group, a methoxymethyl group, a tetrahydropyranyl group.

More preferably, $R^{29}$ refers to hydrogen, methyl or ethyl, $CH_2OH$, $CH_2CH_2OH$, $CH_2NH_2$, $CH_2CH_2NH_2$, $CH_2CN$, $CH_2CH_2CN$, 1-fluoromethyl, difluoromethyl, trifluoromethyl, 2-fluoroethyl, a phenyl or pyridyl group. $R^{29}$ can further be a branched, linear or cyclic acyl group, a phenyl group, or a trimethylsilyl group, a tert-butyldimethylsilyl group, a triethylsilyl group, a tert-butyl diphenylsilyl group, a benzoate group, a benzyl group, a methoxymethyl group, a tetrahydropyranyl group.

$R^{30}$, $R^{31}$ are independently of each other hydrogen, an unsaturated or saturated, linear, branched or cyclic aliphatic radical having 1-8 carbon atoms that may be independently substituted by 1 to 3 substituents selected from the group consisting of OH, $NH_2$, CN, Cl, F, COOH or a carboxyalkyl group, wherein the alkyl radical consists of a straight or branched $C_1$-$C_6$ alkyl or a $C_3$-$C_6$ cycloalkyl. $R^{30}$, $R^{31}$ can further be independently of each other a branched, linear or cyclic acyl group or an amino protective group as defined in Greene's Protective Groups in Organic Synthesis, 5$^{th}$ Edition.

In a preferred embodiment $R^{30}$, $R^{31}$ independently of each other refer to hydrogen, an unsaturated or saturated, linear, branched or cyclic aliphatic radical having 1-6 carbon atoms, that may be independently substituted by 1 to 3 substituents selected from the group consisting of OH, $NH_2$, CN, F, Cl, COOH or a carboxyalkyl group, wherein the alkyl radical consists of a straight or branched $C_1$-$C_6$ alkyl or a $C_3$-$C_6$ cycloalkyl. $R^{30}$, $R^{31}$ can further be independently of each other a branched, linear or cyclic acyl group or a toluensulfonyl group, a tert-butoxycarbonyl group, a benzyloxycarbonyl group, a benzyl group, a fluorenylmethyloxycarbonyl group, a phthalyl group (as phthalimide), a trifluoroacetate group or a triphenylmethyl group.

More preferably, $R^{30}$, $R^{31}$ independently of each other refer to hydrogen, methyl or ethyl, $CH_2OH$, $CH_2CH_2OH$, $CH_2NH_2$, $CH_2CH_2NH_2$, $CH_2CN$, $CH_2CH_2CN$, fluoromethyl, difluoromethyl, trifluoro-methyl, 2-fluoroethyl. $R^{30}$, $R^{31}$ can further be independently of each other a toluensulfonyl group, a tert-butoxycarbonyl group, a benzyloxycarbonyl group, a benzyl group, a fluorenylmethyloxycarbonyl group, a phthalyl group (as phthalimide), a trifluoroacetate group or a triphenylmethyl group.

$R^{32}$—$R^{34}$ are independently of each other a phenyl group, or an unsaturated or saturated, linear, branched or cyclic aliphatic radical having 1-8 carbon atoms that may be independently substituted by 1 to 3 substituents selected from the group(s) consisting of OH, Cl, or F.

In a preferred embodiment $R^{32}$—$R^{34}$ independently of each other refer to a phenyl, an unsaturated or saturated, linear, branched or cyclic aliphatic radical having 1-6 carbon atoms that may be independently substituted by 1 to 3 substituents selected from the group(s) consisting of OH, Cl or F.

More preferably, $R^{32}$—$R^{34}$ independently of each other refer to hydrogen, a phenyl, methyl or ethyl, $CH_2OH$, $CH_2CH_2OH$, 1-fluoromethyl, difluoromethyl, trifluoromethyl, 2-fluoroethyl.

L represents a three-membered linker group —X—Y—Z—
wherein X, Y, Z are independently of each other selected from
$X=SO_2$, $(P=O)OR^1$, $SiR^2R^3$,
$Y=NR^4$, O, $CR^5R^6$,
$Z=CR^7R^8$ and $R^1$ is hydrogen, or an unsaturated or saturated group selected from a linear, branched or cyclic aliphatic radical having 1-8 carbon atoms, a phenyl or benzyl group, $R^2$, $R^3$ are independently of each other hydrogen, an aryl group, a 5-14 membered monocyclic or bicyclic heteroaryl group comprising 1 to 4 same or different heteroatoms or heteroatom groups selected from N, O, S, C=O or C=S, a linear or cyclic acyl group or an unsaturated or saturated, linear, branched or cyclic aliphatic radical having 1-8 carbon atoms that may be independently substituted by an OH group, $R^4$ is a hydrogen, an unsaturated or saturated, linear, branched or cyclic aliphatic radical having 1-8 carbon atoms, an aryl group, a 5-14 membered monocyclic or bicyclic heteroaryl group comprising 1 to 4 same or different heteroatoms selected from N, O, S, C=O and C=S, a linear or cyclic acyl group or a $SO_2$—Ar group (with Ar being identical to Ar in formulae I/II).

$R^5$, $R^6$ are independently of each other hydrogen, an aryl group, a 5-14 membered monocyclic or bicyclic heteroaryl group comprising 1 to 4 same or different heteroatoms or heteroatom groups selected from N, O, S, C=O or C=S, a linear or cyclic acyl group or an unsaturated or saturated, linear, branched or cyclic aliphatic radical having 1-8 carbon atoms that may be independently substituted by an OH group, $R^7$, $R^8$ are independently of each other hydrogen, an aryl group, a 5-14 membered monocyclic or bicyclic heteroaryl group comprising 1 to 4 same or different heteroatoms selected from N, O, S, C=O and C=S, a linear or cyclic acyl group or an unsaturated or saturated, linear, branched or cyclic aliphatic radical having 1-8 carbon atoms that may be independently substituted by an OH group.

The term "active substance" or "active agent" refers to a compound that accomplishes at least one specific or unspecific biological effect in mammalian, plant or microbial cells, tissues, organs or individuals. Such an active substance is commonly used in the fields of agriculture, biology, pharmacy, which includes the fields of veterinary and human medicine. Agrochemically and pharmaceutically active substances are herein preferred.

The terms "photochemical reaction" and "photosplicing reaction" are used herein as synonymous terms. A photosplicing reaction according to the definition provided in the present invention is a photochemically driven preparation of biaryl compounds of formula (I) from the respective precursor compounds of formula (II), whereby a three-membered linker "L" is fully eliminated in the respective products and both aryl residues are fused in a highly regiocontrolled manner.

The photosplicing reaction of the present invention enables an intramolecular elimination of the linker group L, while simultaneously achieving C—C-coupling of Ar and Ar'. Importantly, this reaction proceeds under an outstanding regiocontrol, i.e. the respective substituent patterns of Ar and Ar' are conserved and the C—C-coupling is attained between the very same carbon atoms to which the linker group L was initially connected. Among the high-yield examples, no side products of the respective coupling reactions were detectable.

Further Aspects of the Present Invention

Generally, the reaction to afford a compound according to formula (I) may be performed using a solution of the respective precursor according to formula (II) and a photo-reactor consisting of a lamp (UV emissions in the range of 190-400 nm, preferably 312 nm, 302 nm or broad spectrum UV, more preferably 254 nm) and a UV-transparent chamber or flow cell, preferably equipped with a silica window and offering low optical path length (<1 cm), more preferably made from silica and having less than 1 mm optical path length.

The concentrations of the reactant solutions are adjusted such that the layer thickness is not higher than 100 times, preferably less than 5 times the half-value thickness for the respective wavelength and precursor. Flow rates may be adjusted to afford mean reaction times, i.e. dwell times in the range of 0.5 min to 4 h, preferably in the range of 5 min to 60 min. According to the surface area and cooling capacity of the reactor and irradiation power of the irradiation source, flow rates may be adjusted in the range of 1 µl/min to 10 m$^3$/min, preferably in the range of 0.2 to 100 µL/min per cm$^2$ light exposed window area.

Irradiation power may be set in the range of 0.01 mW/cm$^2$ to 10 W/cm$^2$, preferably in the range of 0.1 mW/cm$^2$ to 1 W/cm$^2$. Proper cooling may be provided to keep the temperature preferably in a range between −40° C. and 60° C., more preferably between 0° C. and 25° C. The reaction may be performed using a continuous, variable or stopped flow, open or closed circuit setup or in batch operation, preferably using continuous flow.

Appropriate solvents are organic or inorganic liquids where compounds according to formula (II) are dissolvable at concentrations between 0.0001 to 1,000 g/L, preferably 1 to 100 g/L and are characterized by suitable extinction coefficients at the given wavelength of the radiation source. The solutions carrying the product mixtures are further processed in accord to standard purification methods known to the skilled person.

An exemplary design of a photoreactor is given by the following dimensions of a flow cell: 16.9×31.9×0.03 cm, covered on top with a silica plate, equipped with inlet and outlet and a UV lamp (Herolab UVT-40 S equipped with 6 Philips TUV 15 W/G15 T8, total power 90 W, 254 nm).

The nature of the solvent(s) is not limited as long as it does not affect the reaction. Examples of suitable solvents include alcohols, alkylnitrils, ethers, toluene, dimethylsulfoxide, acetone and/or mixtures of these solvents. Of these solvents, alcohols and nitriles are preferred.

Suitable alcohols include methanol, ethanol, n-propanol, isopropanol, 1-butanol, 2-butanol, iso-butanol, tert-butanol, n- and iso-pentanols, n- and iso-hexanols. Of these alcohols, methanol, ethanol, n-propanol, isopropanol, 1-butanol, 2-butanol, iso-butanol and tert-butanol are preferred. Particularly preferred is methanol.

Suitable nitriles include acetonitrile, propionitrile, n-butyronitrile, iso-butyronitrile, pivalonitrile. Of these nitriles, acetonitrile is preferred.

Suitable ethers include diethyl ether, 1,4-dioxane, tetrahydrofuran, diisopropylether, methyl tert-butylether, ethyl tert-butylether. Of these ethers, tetrahydrofuran is preferred.

Mixtures of these solvents in any composition and applicable ratios may be applied where necessary for technical reasons. This also includes aqueous mixtures.

[3] Thus, in a third embodiment the present invention provides a method for the preparation of a biaryl compound of general formula (I) according to [1] or [2], characterized in that the photochemically driven reaction is performed in a solution of the respective precursor of formula (II) in a photo-reactor consisting of a light source (UV emissions in the range of 190-400 nm, irradiation power of 0.01 mW/cm$^2$ to 10 W/cm$^2$) and a UV-transparent chamber or flow cell, at flow rates of 10$^{-7}$ L/min to 10$^{-3}$ L/min per cm$^2$ light exposed window area.

[4] The method for the preparation of a biaryl compound of formula (I) according to [3], wherein the solvent is selected from the groups consisting of alcohols, alkylnitrils, ethers, toluene, dimethylsulfoxide, acetone and/or mixtures thereof.

Alternatively, a compound of formula II according to [1] or [2] may be irradiated with a suitable light source (190-400 nm) such as metal vapor or gas discharge lamps, LEDs, or sunlight as a solvent-free thin film on a solid support to afford a compound of formula (I).

Specific surface loads may be in the range of 10$^{-5}$ to 1 mol·m$^{-2}$, whereby compounds of general formula II may be used as mixtures with further excipients required in the particular products, such as varnishes, paints, glues and coatings. Solid supports may consist of any kind of woods, steels, alloys, glass, silica, polymer or other organic or inorganic solid material. Solids may further be specified as plates, sheets, particles or beads or powders of any size. Irradiation power may be set in the range of 0.001 mW/cm$^2$ to 10 W/cm$^2$. Proper cooling may be supplied when critical.

Macromolecules like artificial polymers, or peptides, lipids, polysaccharides may be modified by the reaction of covalently linked compounds according to formula (II) to compounds according to formula (I). The respective reactions may be performed in solution or on surfaces in accordance to reaction parameters as described above.

[5] Thus, alternatively, the present invention provides a method for the preparation of a biaryl compound of formula (I) according to [1] or [2], wherein the respective precursor compound of formula (II) is irradiated with a suitable light source (190-400 nm, irradiation power of 0.001 mW/cm$^2$ to 10 W/cm$^2$) as a solvent-free thin film on a solid support, wherein the specific surface loads are in the range of 10$^{-5}$ to 1 mol·m$^{-2}$.

This allows the reaction to proceed in thin layers on surfaces, in UV light transparent solid matrices (e.g. polymers) or on polymer surfaces. Furthermore, biaryl syntheses may be performed when the precursor according to formula (II) is covalently or non-covalently (e.g. by an affinity label) linked to a solid support (inorganic or organic material) or a biomolecule such as a protein, peptide, antibody, DNA, polysaccharide or lipid.

[6] Thus, a further aspect of the invention is a method for the preparation of a biaryl compound of formula (I) according to [5], wherein the reaction proceeds in thin layers on surfaces, in UV light transparent solid matrices (e.g. polymers) or on polymer surfaces.

[7] The method for the preparation of a biaryl compound of formula (I) according to [1]-[6] characterized in that Ar and Ar', independently of each other, represent a phenyl, naphthyl, furanyl, imidazolyl, pyridyl, thiazolyl, thiophenyl, furanyl, pyrimidyl, pyrazinyl, benzothiazolyl and indolyl group, wherein the above-mentioned groups can be substituted by one or more same or different substituent(s) selected from —OH, —OCH$_3$, a linear, branched or cyclic saturated or unsaturated aliphatic group with 1 to 6 carbon atoms, CN, F, Cl, a —(C=O)H or —(C=O)CH$_3$ group, a phenyl or pyridyl group, a —NH$_2$ group, —N(CH$_3$)$_2$ group, N$_3$, a —COOH, a —COOCH$_3$ group, a —CONH$_2$, a —CONHCH$_3$ or a —CONCH$_3$CH$_3$ group, the groups —X—Y—Z— are independently of each other selected from
X=SO$_2$,
Y=NR$^4$, O, preferably NH and
Z=CR$^7$R$^8$, preferably CH$_2$,
with —X—Y—Z— preferably being an —SO$_2$—NH—CH$_2$— group, and wherein R$^4$ is a hydrogen, an unsaturated or saturated, linear, branched or cyclic aliphatic radical having 1-8 carbon atoms that can be substituted as defined herein above, a C$_6$-C$_{20}$ aryl that can be substituted as defined herein above or a 5-14 membered monocyclic or bicyclic heteroaryl group comprising 1 to 4 same or different heteroatoms selected from N, O, S, C=O and C=S that can be substituted as defined herein above, a linear or cyclic C$_1$-C$_8$ acyl group that may be substituted as defined herein above or a SO$_2$—Ar (with Ar being identical to Ar in formulae I/II).

R$^7$, R$^8$ are independently of each other hydrogen, C$_6$-C$_{20}$ aryl that can be substituted as defined herein above or a 5-14 membered monocyclic or bicyclic heteroaryl group comprising 1 to 4 same or different heteroatoms selected from N, O, S, C=O and C=S that can be substituted as defined herein above, a linear or cyclic C$_1$-C$_8$ acyl group that may be substituted as defined herein above, or an unsaturated or saturated, linear, branched or cyclic aliphatic radical having 1-8 carbon atoms that may be independently substituted by an OH group, preferably R$^7$ and R$^8$ are hydrogen, or independently of each other hydrogen, methyl or ethyl, wherein the methyl or ethyl group(s) independently can be substituted by an OH group.

According to the embodiments of the present invention as described above, the biaryl compound of general formula (I) is unexpectedly obtained in high yields and regioselectivity, free of contaminating metals and, thus, devoid of potential toxicity issues otherwise caused by these impurities, and at lower costs compared to conventional methods.

The method of the present invention is equally suited for laboratory or small scale and for industrial scale preparation of biaryl compounds according to the invention. Thus, the method of the present invention provides an important addition to the synthetic toolbox at laboratory scale.

Alternatively, the reaction parameters of the present invention can be optimized to obtain economically high yields of product, particularly where the reaction is conducted on an industrial scale.

Furthermore, the method of the present invention is particularly suited for commercial, large scale production of biaryl compounds. Relative to conventional methodologies used to produce biaryl compounds, the method of the present invention allows for a simplified, cost-efficient one-step reaction to afford biaryl compounds of general formula (I).

The method may be typically applied in the presence of atmospheric oxygen and moisture, in special cases, however, an inert atmosphere and dry and degassed solvents may be preferred.

Parallel synthesis to obtain combinatorial libraries may be performed using a suitable reaction setup, e.g. microtiter plates, spotted arrays, parallel photo synthesizers. The advantages described above provide unexpectedly large benefits in preparing biaryl compounds according to the present invention for use in novel and/or known active agents in a broad variety of different technical areas. Biaryl compounds as defined in the present invention often form essential components of established active agents and drug candidates, particularly or agrochemically and pharmaceutically active substances, such as e.g., antibacterial, antitumor, neureoprotective and cholesterol-lowering agents, antiarthritic non-steroidal antiinflammatory drugs (NSAIDs) and antihypertensive drugs generally known as sartans.

[8] Thus, a further aspect of the present invention is a method for the preparation of a pharmaceutically or agrochemically active substance containing a biaryl group, comprising the method according to any of [1] to [7] and further processing steps.

[9] A further embodiment is the use of a method according to any of the preceding embodiments [1] to [8] in the synthesis of a pharmaceutically or agrochemically active substance containing a biaryl group.

[10] The use of a method according to [9] in the synthesis of a pharmaceutically active substance containing a biaryl group, wherein the active substance containing a biaryl group is selected from the group(s) of antibacterial, antitumor, neureoprotective and cholesterol-lowering agents, antiarthritic non-steroidal antiinflammatory drugs (NSAIDs), antihypertensive agents, analgesic agents and antiemetic agents that comprise a biaryl group.

One important family of pharmaceutically active agents comprising a biaryl compound as defined in the present invention as a key pharmacophore e.g., is represented by the angiotensin II receptor antagonists, also known as angiotensin receptor blockers (ARBs), AT$_1$-receptor antagonists or generically as sartans, that modulate the renin-angiotensin system in mammals. The sartans are mainly used in the treatment of hypertension, diabetes nephropathy and congestive heart failure. As specific examples within the sartan family the compounds abitesartan, azilsartan, candesartan, fimasartan, irbesartan, losartan, telmisartan, milfasartan, olmesartan, pomisartan and valsartan can be mentioned.

[11] Thus, a further embodiment of the present invention is the use of a method according to any of the preceding embodiments [1] to [10] in the synthesis of a pharmaceutically active substance containing a biaryl group, wherein the active substance containing a biaryl group is a sartan.

To demonstrate the advantages of the synthesis process according to the present invention the essential biaryl building blocks of exemplary compounds of the sartan group of compounds were synthesized.

According to the patent literature, the sartan synthesis is based on Pd-catalyzed cross couplings to connect both aromatic rings, and subsequent bromination at benzylic position, followed by electrophilic substitution with primary amines or imidazole/benzimidazole heterocycles.[17]

Using an appropriately substituted biaryl-precursor of general formula (II) as defined below avoids the usage of heavy metals during the synthesis of the key biaryl pharmacophore. The respective biaryl precursor of formula (II) is readily converted into the biaryl in a high yield using the flow reactor. The respective reactions are shown in detail in the experimental section below. The resulting nitrile-substituted biphenyl building block represents a valuable starting point to the synthesis of most sartans, since the tetrazole substituents are easily accessible by treatment with sodium azide, whereas hydrolysis leads to the carboxy-substituted sartans.

[12] The use of the method according to [11], wherein the biaryl group of formula (I) is a 4'-X-methyl-[1,1'-biphenyl]-2-carbonitrile with X being a leaving group selected from Br or Cl which is substituted with a nitrogen-containing nucleophile selected from primary amines or optionally substituted imidazole, imidazolone, benzimidazole heterocycles and a conversion of the 2-carbonitrile to a tetrazolyl group, a carboxyl group, a 2'-(2,5-dihydro-5-oxo-1,2,4-oxadiazol-3-yl) group or optionally followed by further conventional processing steps to obtain a pharmaceutically active compound selected from, candesartan, eprosartan, irbesartan, losartan, EXP3174, olmesartan, telmisartan, valsartan.

By way of analogy the method of the invention can be used for the preparation of other pharmaceutically active agents comprising a biaryl group according to the invention. A number of illustrative examples are shown below in the experimental section.

The use of the method according to any of the preceding embodiments [1] to [10] in the synthesis of a pharmaceutically active substance containing a biaryl group, wherein the active substance containing a biaryl group is a histamine H3 receptor antagonist selected from A-349821 or ABT-239, A-698418, A-687136, A-688057, JNJ-280566 or their analogues.

The use of the method according to any of the preceding embodiments in the synthesis of a pharmaceutically active substance containing a biaryl group, wherein the active substance containing a biaryl group is a BCL-$X_L$ inhibitor selected from WEHI-539, A-1331852, ABT-737, BM-1197 or their analogues.

[13] The use of the method according to any of the preceding embodiments in the synthesis of a pharmaceutically active substance containing a biaryl group, wherein the active substance containing a biaryl group is a nonsteroid anti-inflammatory drug (NSAID) selected from diflunisal, flurbiprofen, oxaprozin, celecoxib, valdecoxib, parecoxib, etoricoxib, licofelone, felbinac, xenbucin or their analogues.

[14] The use of the method in the synthesis of a nonsteroid anti-inflammatory drug (NSAID) according to [13], wherein the pharmaceutically active substance containing a biaryl group is selected from the group consisting of diflunisal, felbinac and xenbucin.

The use of the method according to any of the preceding embodiments in the synthesis of a pharmaceutically active substance containing a biaryl group, wherein the active substance containing a biaryl group is an inhibitor of the lipoprotein-associated phospholipase A2 selected from darapladib, SB-435495 or their analogues.

The use of the method according to any of the preceding embodiments in the synthesis of a pharmaceutical active substance containing a biaryl group, wherein the active substance containing a biaryl group is a cannabinoid receptor antagonist selected from LY 320135, SR144528, rimonabant or their analogues.

[15] The use of the method according to any of the preceding embodiments in the synthesis of a pharmaceutically active substance containing a biaryl group, wherein the active substance containing a biaryl group is an active ingredient against infectious diseases selected from radezolid, tedizolid, epimerox, BMS isoxazolinone, ledipasvir, daclatasvir and arylomycin or their analogues.

The use of the method according to any of the preceding embodiments in the synthesis of a pharmaceutical active substance containing a biaryl group, wherein the active substance containing a biaryl group is a 2-sodium-glucose transport inhibitor selected from canagliflozin and its derivatives.

The use of the method according to any of the preceding embodiments in the synthesis of a pharmaceutical or agrochemical active substance containing a biaryl group, wherein the active substance containing a biaryl group is a 3-hydroxy-3-methyl-glutaryl-coenzyme A reductase inhibitor selected from the statin group as represented by atorvastatin.

[16] The use of the method according to any of the preceding embodiments in the synthesis of a pharmaceutical active substance containing a biaryl group, wherein the active substance containing a biaryl group is a GABA receptor modulator, agonist or antagonist selected from zolpidem, CL-218872, L-838417, alpidem, necopidem, saripidem, NS2664, NS2710, pipequaline, TP-003 or their derivatives.

Finally, the new method has been successfully employed in the synthesis of the important analgesic and antiemetic active agent cannabinol (6,6,9-trimethyl-3-pentyl-6H-benzo[c]chromen-1-ol) as shown in formula

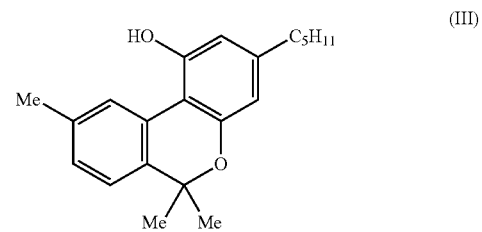

(III)

The synthesis of the active agent cannabinol is shown in more detail in the experimental section below.

[17] The use of the method according to any of the preceding embodiments in the synthesis of a pharmaceutical active substance containing a biaryl group, wherein the active substance containing a biaryl group is cannabinol (6,6,9-trimethyl-3-pentyl-6H-benzo[c]chromen-1-ol).

[18] The use of the method according to embodiment [17], wherein the 2',6'-dimethoxy-5-methyl-4'-pentyl-[1,1'-biphenyl]-2- carbonitrile of formula (I) is further converted to 1-hydroxy-9-methyl-3-pentyl-6H-benzo[c]chromen-6-one followed by further conventional processing steps to obtain the pharmaceutically active compound cannabinol (6,6,9-trimethyl-3-pentyl-6H-benzo[c]chromen-1-ol).

Elucidation of the Potential Reaction Mechanism

Since sulfonamides (L=—SO$_2$—NH—CH$_2$—) as well as the structures of the general formula (I) and (II) show strong UV absorbance, the conversion rate may be hampered in concentrated solutions (>1 g·L$^{-1}$) and thick layers. We found that these limitations can be overcome when performing the reaction in flow and at minimum layer thickness (<0.4 mm). Using a microfluidic system we demonstrated that it is possible to [e.g.,] convert sulfonamides with continuous flow and a defined retention time in the reactor. To upscale the reaction, we constructed a simple flow chamber composed of a finely milled aluminium plate covered by a highly planar silica glass sheet and equipped with two channels for filling and unloading. This reactor was constantly exposed to UV light emitted from six commercial uncoated low-pressure metal vapor lamps (P$_{sum}$=90 W, λ$_{max}$=254 nm).

In light of the photochemical reaction conditions, the rigorous regio- and chemoselectivity of biaryl formation is striking. Previous studies on the photochemistry of sulfonamides showed that the S—N bond can be cleaved homolytically, followed by formation of carbon-centered radicals.[18]

It is also known that the photochemical activation of aromatic sulfonamides (and sulfonates) can lead to radical Smiles rearrangements.[15]

By analogy, it would appear plausible that UV-irradiation of sulfonamide(/sulfonate) affords reactive aryl radicals in a Norrish type I reaction.

However, if biaryl formation involved the pairing of aryl radicals, one would expect the presence of homocoupling products. Careful analyses of the reaction mixtures did not give any evidence for biaryls that would arise from the recombination of two identical radicals. To evaluate the potential involvement of radicals in the photoreaction various experiments were performed.

It was intensively tested whether the reaction can be mediated with radical starters such as dibenzoyl peroxide (DBPO) and azobisisobutyronitrile (AIBN). Neither the radical starters alone nor the mixture of tributyltinhydride and AIBN, which is used for the radical Smiles rearrangement, initiated the biaryl coupling.

Moreover, it was found that the course of the photoreaction is not affected in the presence of radical quenchers like 2,6-di-tert-butyl-4-methylphenol (BHT), even when added in large excess (10 eq.) to trap potential intermediary radicals.

Even when using toluene as a cosolvent in acetonitrile (v/v=50:50), no side products of the coupling reaction were detectable. Finally, different regioisomeric sulfonamides with methyl residues in para-, meta- and ortho-position were prepared. In case of free radical intermediates, one would expect a bias in the recombination due to favored and disfavored positions of the radical. However, in all cases, selective production of the para-, meta- and ortho-substituted biaryls was found.

The outstanding regiocontrol could be rationalized by an intramolecular reaction that may involve charged transition states. The sulfonamide/sulfonate linker would allow the aryl residues to be positioned in a way that allowed orbital overlaps.

Without being bound by this theory in any way, we propose that a labile five-membered intermediate decomposes sequentially or in a concerted fashion that would be reminiscent of a retro-[3+2] cycloaddition as shown in FIG. 1.

Irrespective of the exact timing of the bond fissions, the traceless linker could fragment by hydrolysis into sulfur dioxide, ammonia and formaldehyde.

To support this model, we analyzed the side products resulting from the cleavage of the linker. Sulfur dioxide formation was monitored by headspace GC-MS analysis of the same solutions. Only in the headspace of the irradiated sample the expected mass m/z=64 ($SO_2$) was detected.

For the qualitative detection of ammonia, we employed an alkaline solution of potassium tetraiodomercurate(II) (Nessler's reagent). Whereas the negative controls (solvent only or educt not irradiated) gave colorless solutions, irradiation of the sulfonamide solution followed by addition of Nessler's reagent resulted in a pale orange coloration, which is diagnostic for the presence of ammonia.

Next, we used 2,4-dinitrophenylhydrazine in 1 M HCl aq. (Brady's reagent) to trap the predicted formaldehyde. Whereas no hydrazones were detectable by HPLC-HRMS in negative control reactions, we obtained the formaldehyde-derived hydrazone from the photoreaction mixture in which the biaryl was formed. The identity of the product was verified by comparison of UV-Vis spectra, HR-MS data, and retention times with a synthetic reference generated from a formalin-spiked solution.

Taken together, the photoreaction of the sulfonamide leads to a traceless cleavage of the linker and yields a single biaryl product by a sterically defined ipso/ipso substitution.

Using the photoreactor, we were able to test the scope of the photochemical reaction at preparative scale. We synthesized a broad range of (sulfonamide) derivatives of general formula (II) by classical methods, such as nucleophilic substitution reactions of sulfonyl chlorides and benzyl amines with diverse substitution patterns and found that the photoreaction tolerates a large variety of substituents. Prominent examples out of this variety of substituents are specifically shown in Table 1 below.

Overall the substituents at the benzylamine residue (Ar' in formula II) have a more pronounced impact on biphenyl yields than the moieties that are attached to the arylsulfone (Ar) moiety. Biaryls are obtained in good to excellent yields when using educts equipped with electron-withdrawing groups like nitriles or carboxylate esters.

Thus, the novel clean, metal-free and highly selective reaction of the present invention is suitable for a broad range of organic chemical syntheses, e.g., in the field of building block synthesis, organic materials (e.g. polymers), liquid crystals, agrochemicals and is particularly suitable for the synthesis of pharmaceutically active ingredients having biaryl- or biheteroaryl moieties as structural elements.

EXPERIMENTAL SECTION

The following examples illustrate the general process according to the present invention.

General Synthesis Procedure

All reagents were obtained from commercial suppliers (Sigma Aldrich, TCI, Alfa Aesar, etc.) and used without further purification unless otherwise explained. Reactions were carried out under inert gas (argon) by using the Schlenk technique in dried solvents. Dichloromethane (DCM), acetonitrile (MeCN), methanol (MeOH) and chloroform were used from a solvent purification system (Innovative Technologies). Open column chromatographic separations were executed on silica gel (Kieselgel 60, 15-40 µm, Merck KGaA). Reaction progresses were monitored by thin layer chromatography (TLC) (silica gel on aluminium sheets 20×20 cm with fluorescent dye 254 nm, Merck KGaA), GC-MS or HPLC-(HR)MS. Photoreactions were performed on a photo reactor (16.9×31.9×0.03 cm) with variable flow rates and UV lamp Herolab UVT-40 S equipped with 6 tubes Philips TUV 15 W/G15 T8 (total power 90 W; 254 nm).

General Analytical Procedures

All 1D ($^1H$, $^{13}C$, DEPT) and 2D NMR ($^1H$-$^1H$ COSY, HSQC, NOESY, HMBC) have been recorded in deuterated solvents on a Bruker AVANCE II 300, AVANCE III 500 or 600 MHz instrument equipped with Bruker Cryo Platform. The chemical shifts are reported in ppm relative to the solvent residual signal ($^1H$: $\delta$ ($CHCl_3$)=7.26 ppm, $\delta$ ($CH_2Cl_2$)=5.32 ppm, $\delta$ (MeOH)=3.31 ppm, $\delta$ (DMSO)=2.50 ppm, $\delta$ (MeCN)=1.94 ppm. $^{13}C$: $\delta$ ($CHCl_3$)=77.16 ppm, $\delta$ ($CH_2Cl_2$)=53.84 ppm, $\delta$ (MeOH)=49.00 ppm, $\delta$ (DMSO)=39.52 ppm, $\delta$ (MeCN)=1.32 ppm or 118.26 ppm). Following abbreviations are used for multiplicities of resonance signals: s=singlet, d=doublet, t=triplet, q=quartet, qt=quintet, br=broad. Preparative HPLC purification was achieved by using Gilson Abimed device with Binary Pump 321 and dual wavelength detector 156 (column: Phenomenex Luna C18, 10 µm, 250×21.2 mm, eluent: water, MeCN). Gas-chromatographic measurements were executed on a Thermo Trace GC Ultra equipped with CombiPAL autosampler and coupled with FID and Thermo Polaris Q electron impact ion trap mass spectrometer. GC conditions: column SGE BPX5 30 m×0.25 mm ID; carrier gas helium; split injection with split ratio 1:10 and injection volume 250 µL; 1.5 mL/min carrier gas flow; temperature profile 0-1 min: 40° C., 1-3 min: heating up to 100° C. (30° C./min), 3-28 min: heating up to 350° C. (10° C./min). LC-MS measurements were performed using an Exactive Orbitrap High Performance Benchtop LC-MS with electrospray ion source and Surveyor HPLC system (Thermo Fisher Scientific, Bremen), a Q Exactive Orbitrap High Performance Benchtop LC-MS with electrospray ion source and Accela HPLC system (Thermo Fisher Scientific, Bremen) or LTQ Velos Ion Trap Benchtop LC-MS with electrospray ion source and Surveyor HPLC system (Thermo Fisher Scientific, Bremen). HPLC conditions using Exactive: C18 column (Thermo Fisher Betasil C18, 3 µm, 150×2.1 mm) and gradient elution (MeCN (0.1% (v/v) HCOOH)/H$_2$O (0.1% (v/v) HCOOH) starting with 5/95 for 1 min, going up to 99/1 in 16 min, then 99/1 for 15 min; flow rate 0.2 mL/min; injection volume: 3 µL). HPLC conditions using Q Exactive: C18 column (Thermo Fisher Accucore C18, 2.6 µm, 100× 2.1 mm) and gradient elution (MeCN (0.1% (v/v) HCOOH)/ H$_2$O (0.1% (v/v) HCOOH) starting with 5/95, going up to 98/2 in 10 min, then 98/2 for 12 min; flow rate 0.2 mL/min; injection volume: 3 µL). HPLC conditions using LTQ: C18 column (Phenomenex Kinetex XB-C18, 2.6 µm, 100×3 mm) and gradient elution (MeCN (0.1% (v/v) HCOOH)/H$_2$O (0.1% (v/v) HCOOH) 10/90 for 1 min, going up to 100/0 in 8 min, then 100/0 for 4 min; flow rate 0.6 mL/min; injection volume: 5 µL). HPLC conditions for regioisomer separation using Q Exactive: C18 column (Thermo Fisher Accucore C18, 2.6 µm, 100×2.1 mm) and isocratic elution (MeCN (0.1% (v/v) HCOOH)/H$_2$O (0.1% (v/v) HCOOH) with 50/50 for 20 min, then 100/0 for 10 min; flow rate 0.2 mL/min; injection volume: 3 µL).

Example 1: Preparation of the biaryl Compound methyl 4'-methyl-(1,1'-biphenyl)-4-carboxylate a. Synthesis of the Precursor methyl 4-(((4-methylphenyl) sulfonamido)methyl)benzoate According to General Formula II.

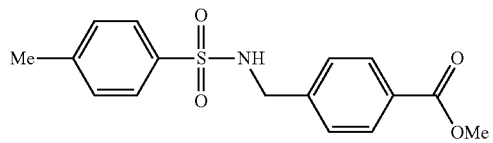

A solution of 4-methylbenzenesulfonyl chloride (190.6 mg, 1 mmol, 1 eq.), methyl 4-(aminomethyl)benzoate hydrochloride (201.7 mg, 1 mmol, 1 eq.) and N,N-diisopropylethylamine (284.4 mg, 383.2 µL, 2.2 mmol, 2.2 eq.) in DCM (4 mL) was stirred for 1 h at room temperature. After dilution with ethyl acetate (20 mL) the solution was washed with water (20 mL), aqueous hydrochloric acid (1 M, 20 mL) and brine (20 mL). The organic layer was dried with sodium sulfate, filtered and the solvent was evaporated. The crude product was recrystallized from ethanol/water (v/v=1/1) to afford the pure title compound (268.2 mg, 0.84 mmol, 84%) as white crystals.

$^1$H NMR (300 MHz; CDCl$_3$): δ=2.42 (s, 3H, CH$_3$—C), 3.89 (s, 3H, CH$_3$—O), 4.17 (d, 2H, $^3J_{HH}$=6.3 Hz, CH$_2$), 5.01 (t, 1H, $^3J_{HH}$=6.3 Hz, NH), 7.25-7.30 (m, 4H, CH$_2$—C—(CH)$_2$+CH$_3$—C—(CH)$_2$), 7.74 (d, 2H, $^3J_{HH}$=8.3 Hz, SO$_2$—C—(CH)$_2$), 7.92 (d, 2H, $^3J_{HH}$=8.3 Hz, CO—C—(CH)$_2$) ppm. $^{13}$C NMR (75.5 MHz; CDCl$_3$): δ=21.7 (1C, CH$_3$—C), 47.0 (1C, CH$_2$), 52.3 (1C, CH$_3$—O), 127.3 (2C, SO$_2$—C—(CH)$_2$), 127.8 (2C, CH$_2$—C—(CH)$_2$), 129.8 (1C, CO—C), 129.9 (2C, CH$_3$—C—(CH)$_2$), 130.0 (2C, CO—C—(CH)$_2$), 136.7 (1C, SO$_2$—C), 141.7 (1C, C—CH$_2$), 143.8 (1C, C—CH$_3$), 166.8 (1C, O—CO—C) ppm. HRMS (ESI$^+$) calcd. for C$_{16}$H$_{18}$NO$_4$S$^+$: 320.0951; found: 320.0952. HRMS (ESI$^-$) calcd. for C$_{16}$H$_{16}$NO$_4$S$^-$: 318.0806; found: 318.0809.

b. Preparation of methyl 4'-methyl-(1,1'-biphenyl)-4-carboxylate

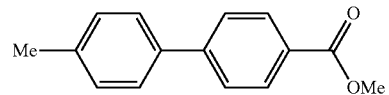 [SMILES: COC(=O)c1ccc(-c2ccc(C)cc2)cc1]

A solution of methyl 4-(((4-methylphenyl)sulfonamido) methyl)benzoate (20.0 mg, 62.6 µmol) in MeCN (5 mL) was loaded on the photo reactor with a flow rate of 1 mL/min (MeCN) and irradiated with UV light at room temperature. The solvent fraction containing the photoproducts was collected and the solvent was removed under reduced pressure. The residue was purified by open column chromatography to yield the title compound (13.0 mg, 92%).

$^1$H NMR (300 MHz; CDCl$_3$): δ=2.41 (s, 3H, CH$_3$—C), 3.94 (s, 3H, CH$_3$—O), 7.27 (d, 2H, $^3J_{HH}$=8.2 Hz, CH$_3$—C—(CH)$_2$), 7.53 (d, 2H, $^3J_{HH}$=8.2 Hz, CH$_3$—C—(CH)$_2$—(CH)$_2$), 7.65 (d, 2H, $^3J_{HH}$=8.5 Hz, CO—C—(CH)$_2$—(CH)$_2$), 8.09 (d, 2H, $^3J_{HH}$=8.5 Hz, CO—C—(CH)$_2$) ppm. $^{13}$C NMR (75.5 MHz; CDCl$_3$): δ=21.3 (1C, CH$_3$—C), 52.2 (1C, CH$_3$—O), 126.9 (2C, CO—C—(CH)$_2$—(CH)$_2$), 127.2 (2C, CH$_3$—C—(CH)$_2$—(CH)$_2$), 128.7 (1C, CO—C), 129.8 (2C, CH$_3$—C—(CH)$_2$), 130.2 (2C, CO—C—(CH)$_2$), 137.2 (1C, CH$_3$—C—(CH)$_2$—(CH)$_2$—C), 138.3 (1C, CH$_3$—C), 145.7 (1C, CO—C—(CH)$_2$—(CH)$_2$—C) 167.2 (1C, CO) ppm. HRMS (ESI$^+$) calcd. for C$_{15}$H$_{15}$O$_2^+$: 227.1067; found: 227.1065.

Examples 2-25 (Table 1)

The following examples were prepared in analogy to example 1 with minor variations of reaction parameters.

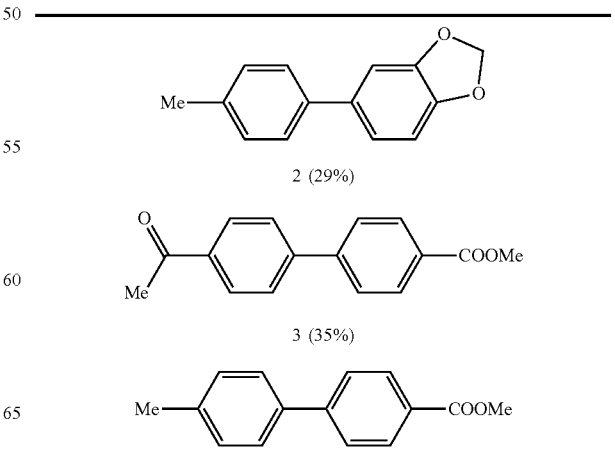

2 (29%)

3 (35%)

-continued
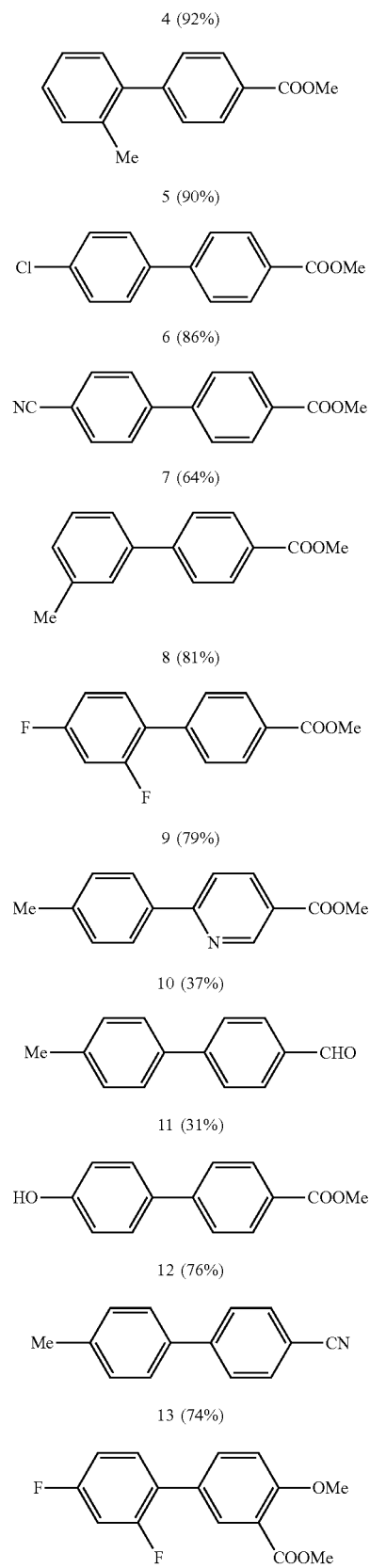
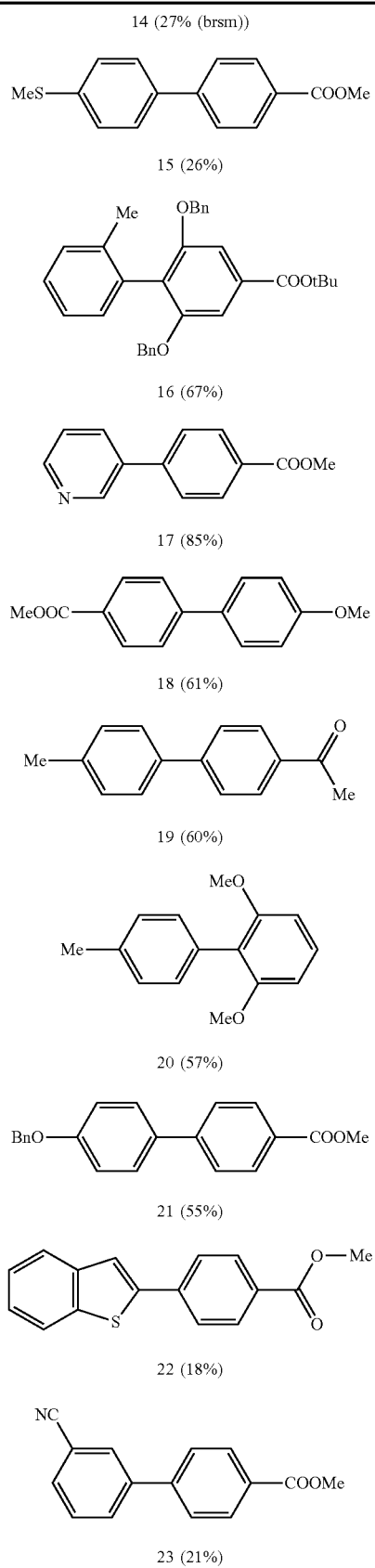

-continued

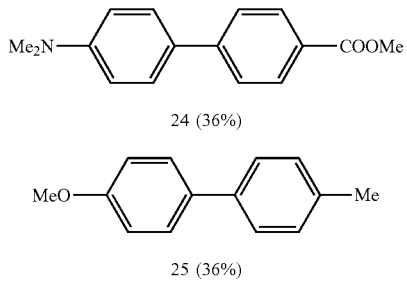

24 (36%)

25 (36%)

Biaryl Compounds as Essential Buiding Blocks In Active Ingredients

The following examples demonstrate that biaryl groups made according to the method of the present invention provide essential building blocks within a broad variety of active ingredients.

Furthermore, to evaluate the potential utility spectrum of the photoreaction of the present invention we aimed at synthesizing biaryl building blocks found in different classes of pharmaceutical compounds. A general overview is provided in FIG. 2.

Examples 26-27: Synthesis of Biaryl Building Blocks of Examplary Sartan Compounds Example 26: Preparation of the Biaryl Building Block for e.g., Losartan and/or Valsartan a. Preparation of N-(2-Cyanobenzyl)-4-methylbenzenesulfonamide

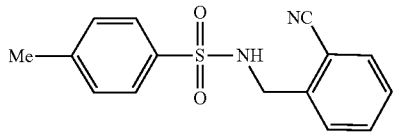 [SMILES: Cc1ccc(S(=O)(=O)NCc2ccccc2C#N)cc1]

A solution of 4-methylbenzenesulfonyl chloride (190.7 mg, 1 mmol, 1 eq.) and 2-(aminomethyl)benzonitrile hydrochloride (168.6 mg, 1 mmol, 1 eq.) in DCM (4 mL) was prepared and N,N-diisopropylethylamine (284.4 mg, 383.2 µL, 2.2 mmol, 2.2 eq.) was added. The solution was stirred for 4 h at room temperature. The mixture was diluted with aqueous hydrochloric acid (1 M, 30 mL) and ethyl acetate (50 mL). The separated organic phase was washed with brine (30 mL). The organic layer was dried with sodium sulfate, filtered and the solvent was removed under reduced pressure. The residue was purified by open column chromatography (ethyl acetate/cyclohexane (v/v=1/6), $R_f$=0.36) to yield the title compound as a white solid (212.8 mg, 0.74 mmol, 74%).

$^1$H NMR (300 MHz; CDCl$_3$): δ=2.42 (s, 3H, —CH$_3$), 4.35 (d, 2H, $^3J_{HH}$=6.6 Hz, —CH$_2$—), 5.06 (t, 1H, $^3J_{HH}$=6.6 Hz, —NH—), 7.28 (d, 2H, $^3J_{HH}$=8.2 Hz, —C(Me)—CH—), 7.36 (td, 1H, $^3J_{HH}$=7.4 Hz, $^4J_{HH}$=1.2 Hz, —C(CH$_2$)—CH—), 7.54-7.60 (m, 3H, —C(CN)—CH—CH—), 7.72 (d, 2H, $^3J_{HH}$=8.2 Hz, —C(Me)—CH—CH—) ppm. $^{13}$C NMR (75.5 MHz; CDCl$_3$): δ=21.7 (1C, —CH$_3$), 45.3 (1C, —CH$_2$—), 111.6 (1C, —C(CN)), 117.3 (1C, —CN), 127.2 (2C, —C(Me)—CH—CH—), 128.5 (1C, —C(CH$_2$)—CH—), 129.5 (1C, —C(CN)—CH—CH—CH—), 130.0 (2C, —C(Me)—CH—CH—), 132.9 (1C, —C(CN)—CH—CH—CH—), 133.4 (1C, —C(CN)—CH—CH—CH—), 136.9 (1C, —C(CH$_3$)—), 140.6 (1C, —C(SO$_2$)—), 144.0 (1C, —C(CH$_2$)—) ppm. HRMS (ESI$^+$) calcd. for C$_{15}$H$_{15}$N$_2$O$_2$S$^+$: 287.0749; found: 287.0845. HRMS (ESI$^-$) calcd. for C$_{15}$H$_{13}$N$_2$O$_2$S$^-$: 285.0703; found: 285.0702.

b. Preparation of 4'-Methyl-[1,1'-biphenyl]-2-carbonitrile

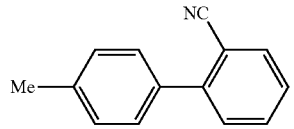

A solution of N-(2-cyanobenzyl)-4-methylbenzenesulfonamide (21.0 mg, 73.3 µmol) in MeOH (10 mL) was loaded on the photo reactor with a flow rate of 1.5 mL/min (MeOH) and irradiated with UV light at room temperature. The solvent fraction containing the photoproducts was collected and the solvent was removed under vacuum. The residue was purified by open column chromatography (DCM) to yield remaining educt (7.3 mg, 27.2 µmol, 37%) and title compound (6.2 mg, 32.1 µmol, 44%, brsm: 70%).

$^1$H NMR (500 MHz; CD$_2$Cl$_2$): δ=2.43 (s, 3H, —CH$_3$), 7.32 (d, 2H, $^3J_{HH}$=7.9 Hz, —C(CH$_3$)—CH—), 7.45 (m, 3H, —C(CH$_3$)—CH—CH— and —C(CN)—CH—CH—), 7.51 (d, 1H, $^3J_{HH}$=7.6 Hz, —C(Ar)—CH—), 7.65 (td, 1H, $^3J_{HH}$=7.7 Hz, $^4J_{HH}$=1.2 Hz, —C(Ar)—CH—CH—), 7.76 (d, 1H, $^3J_{HH}$=7.4 Hz, —C(CN)—CH—) ppm. $^{13}$C NMR (125.8 MHz; CD$_2$Cl$_2$): δ=21.4 (1C, —CH$_3$), 111.6 (1C, —C(CN)—), 119.2 (1C, —CN), 127.8 (1C, —C(CN)—CH—CH—), 129.0 (2C, —C(CH$_3$)—CH—CH—), 129.7 (2C, —C(CH$_3$)—CH—), 130.4 (1C, —C(Ar)—CH—), 133.2 (1C, —C(Ar)—CH—CH—), 134.1 (1C, —C(CN)—CH—), 135.9 (1C, —C—C—C(CN)—), 139.3 (1C, —C(Me)—), 145.9 (1C, —C—C—C(CN)—) ppm. HRMS (ESI$^+$) calcd. for C$_{14}$H$_{12}$N$^+$: 194.0964; found: 194.0967.

Example 27: Preparation of the Biaryl Building Block for e.g., Telmisartane a. Preparation of methyl 2-(((4-methylphenyl)sulfonamido)methyl)benzoate

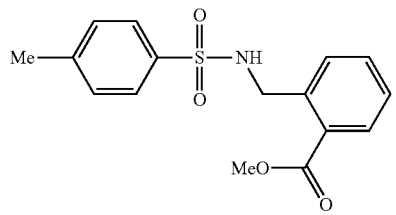 [SMILES: COC(=O)c1ccccc1CNS(=O)(=O)c1ccc(C)cc1]

A solution of 4-methylbenzenesulfonyl chloride (190.7 mg, 1 mmol, 1 eq.), methyl 2-(aminomethyl)benzoate hydrochloride (201.7 mg, 1 mmol, 1 eq.) and N,N-diisopropylethylamine (284.4 mg, 383.2 µL, 2.2 mmol, 2.2 eq.) in DCM (4 mL) was stirred for 16 h at room temperature. After dilution with ethyl acetate (20 mL) the solution was washed with water (10 mL), aqueous hydrochloric acid (1 M, 10 mL) and brine (10 mL). The organic layer was dried with sodium sulfate, filtered and the solvent was removed under reduced pressure. The crude product was obtained as yellow oil (302 mg, 0.95 mmol, 95%) and used without further purification.

$^1$H NMR (500 MHz; CDCl$_3$): δ=2.38 (s, 3H, —C(CH$_3$)—), 3.87 (s, 3H, —OCH$_3$), 4.32 (d, 2H, $^3J_{HH}$=7.0 Hz, —CH$_2$—), 5.84 (t, 1H, $^3J_{HH}$=7.0 Hz, —NH—), 7.19 (d, 2H, $^3J_{HH}$=8.4 Hz, —C(CH$_3$)—CH—), 7.32 (m, 2H, —CH$_2$—C—CH— and —C(COOMe)—CH—CH—), 7.41 (t, 1H, $^3J_{HH}$=7.6 Hz, —CH$_2$—C—CH—CH—), 7.67 (d, 2H, $^3J_{HH}$=8.4 Hz, —C(CH$_3$)—CH—CH—), 7.89 (d, 1H, $^3J_{HH}$=7.7 Hz, —C(COOMe)—CH—) ppm. $^{13}$C NMR (125.8 MHz; CDCl$_3$): δ=21.6 (1C, —C(CH$_3$)—), 47.0 (1C, —CH$_2$—), 52.5 (1C, —OCH$_3$), 127.1 (2C, —C(CH$_3$)—CH—CH—), 128.2 (1C, —C(COOMe)—CH—CH—), 128.9 (1C, —C(COOMe)—), 129.6 (2C, —C(CH$_3$)—CH—), 131.2 (1C, —C(COOMe)—CH—), 131.7 (1C, —CH$_2$—C—CH—), 133.0 (1C, —CH$_2$—C—CH—CH—), 138.0 (1C, —C(CH$_3$)—), 138.7 (1C, —CH$_2$—C—), 143.1 (1C, —SO$_2$—C—), 167.9 (1C, —CO—) ppm. HRMS (ESI$^+$) calcd. for C$_{16}$H$_{18}$NO$_4$S$^+$: 320.0951; found: 320.0948. HRMS (ESI$^-$) calcd. for C$_{16}$H$_{16}$NO$_4$S$^-$: 318.0806; found: 318.0807.

b. Preparation of methyl 4'-methyl-[1,1'-biphenyl]-2-carboxylate

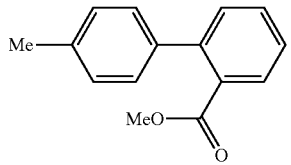 [SMILES: COC(=O)c1ccccc1-c1ccc(C)cc1]

A solution of methyl 2-(((4-methylphenyl)sulfonamido)methyl)benzoate (19.9 mg, 62.3 μmol) in MeOH (10 mL) was loaded on the photo reactor with a flow rate of 2 mL/min (MeOH) and irradiated with UV light at room temperature. The solvent fraction containing the photoproducts was collected and the solvent was removed under vacuum. The residue was purified by open column chromatography to yield the title compound (9.2 mg, 40.7 μmol, 65%).

$^1$H NMR (500 MHz; CDCl$_3$): δ=2.40 (s, 3H, —C(CH$_3$)), 3.66 (s, 3H, —OCH$_3$), 7.21 (s, 4H, Me-C—CH—CH—), 7.38 (m, 2H, —C(COOMe)—C—CH—CH—CH—), 7.51 (t, 1H, $^3J_{HH}$=7.7 Hz, —C(COOMe)—C—CH—CH—), 7.80 (d, 1H, $^3J_{HH}$=7.7 Hz, —C(COOMe)—CH—) ppm. $^{13}$C NMR (125.8 MHz; CDCl$_3$): δ=21.4 (1C, —C(CH$_3$)—), 52.1 (1C, —OCH$_3$), 127.1 (1C, —C(COOMe)—C—CH—), 128.4 (2C, —C(CH$_3$)—CH—), 129.0 (2C, —C(CH$_3$)—CH—CH—), 129.9 (1C, —C(COOMe)—CH—), 130.9 (1C, —C(COOMe)—CH—CH—), 131.0 (1C, —C(COOMe)—), 131.3 (1C, —C(COOMe)—C—CH—CH—), 137.1 (1C, —C(CH$_3$)—), 138.5 (1C, —C—C—C(COOMe)—), 142.6 (1C, —C—C(COOMe)—), 169.4 (1C, —CO—) ppm. HRMS (ESI$^+$) calcd. for C$_{15}$H$_{15}$O$_2$$^+$: 227.1067; found: 227.1069.

Example 28: Synthesis of Biaryl Building Blocks of Antibiotic Compounds

In another experiment, the synthesis of an antibiotic substance is performed.

Figure 2:
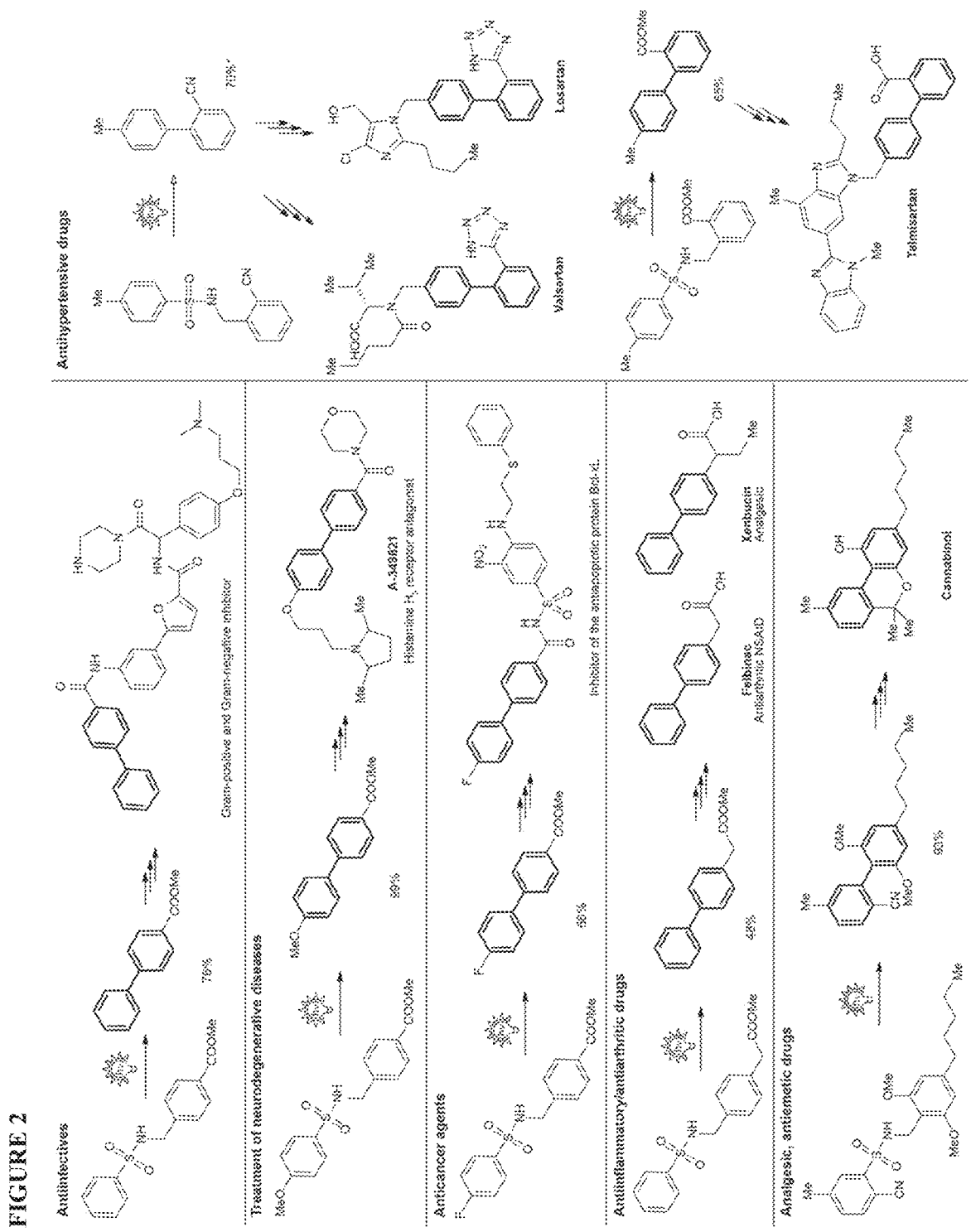
FIG. 2 provides an illustration of an exemplary number of important groups of pharmaceutically active agents comprising biaryl groups as defined in the present invention as essential building blocks in order to demonstrate the extraordinary synthetic potential of the new reaction in the synthesis of industrially relevant biaryl active argents.

The biaryl compound of general formula (I) provides the core structure of specific antimicrobial compounds as shown in FIG. 2.

Example 28: Methyl [1,1'-biphenyl]-4-carboxylate a. Preparation of methyl 4-(phenylsulfonamidomethyl)benzoate.

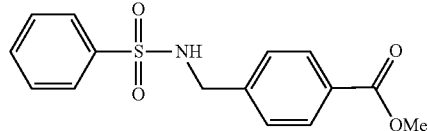 [SMILES: COC(=O)c1ccc(CNS(=O)(=O)c2ccccc2)cc1]

A solution of benzenesulfonyl chloride (176.6 mg, 1 mmol, 128 μL, 1 eq.), methyl 4-(aminomethyl)benzoate hydrochloride (201.7 mg, 1 mmol, 1 eq.) and 4-dimethylaminopyridine (366.5 mg, 3 mmol, 3 eq.) in DCM (2 mL) was stirred for 16 h at room temperature. After dilution with DCM (10 mL) the solution was washed with water (10 mL), aqueous hydrochloric acid (1 M, 10 mL), aqueous sodium bicarbonate solution (10%, 10 mL) and brine (10 mL). The organic layer was dried with sodium sulfate, filtered and the solvent was evaporated. The crude product was purified by preparative HPLC to provide the title compound (149 mg, 0.49 mmol, 49%).

$^1$H NMR (300 MHz; CD$_3$CN): δ=3.85 (s, 3H, —OCH$_3$), 4.13 (d, 2H, $^3J_{HH}$=6.2 Hz, —CH$_2$—), 6.13 (t, 1H, $^3J_{HH}$=6.3 Hz, —NH—), 7.33 (d, 2H, $^3J_{HH}$=8.2 Hz, —CH$_2$—C—CH—), 7.51-7.65 (m, 3H, —SO$_2$—C—CH—CH—CH—), 7.81-7.84 (m, 2H, —SO$_2$—C—CH—), 7.89 (d, 2H, $^3J_{HH}$=8.2 Hz, —CO—C—CH—) ppm. $^{13}$C NMR (75.5 MHz; CDCl$_3$): δ=47.0 (1C, —CH$_2$—), 52.3 (1C, —OCH$_3$), 127.2 (2C, —SO$_2$—C—CH—), 127.8 (2C, —CH$_2$—C—CH—), 129.4 (2C, —SO$_2$—C—CH—CH—), 129.9 (1C, —CO—C—), 130.1 (2C, —CO—C—CH—), 133.0 (1C, —SO$_2$—C—CH—CH—CH—), 139.9 (1C, —SO$_2$—C—), 141.5 (1C, —CH$_2$—C—), 166.8 (1C, —CO—) ppm. HRMS (ESI$^+$) calcd. for C$_{15}$H$_{16}$NO$_4$S$^+$: 306.0795; found: 306.0792. HRMS (ESI$^-$) calcd. for C$_{15}$H$_{14}$NO$_4$S$^-$: 304.0649; found: 304.0653.

b. Preparation of methyl [1,1'-biphenyl]-4-carboxylate

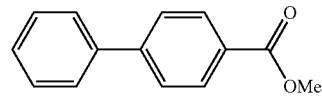 [SMILES: COC(=O)c1ccc(-c2ccccc2)cc1]

A solution of methyl 4-(phenylsulfonamidomethyl)benzoate (27.4 mg, 89.7 μmol) in MeOH (10 mL) was loaded on the photo reactor with a flow rate of 1 mL/min (MeOH) and irradiated with UV light at room temperature. The solvent fraction containing the photoproduct was collected and the solvent was removed under vacuum. The residue was purified by open column chromatography to yield the title compound (14.5 mg, 68.2 μmol, 76%).

$^1$H NMR (300 MHz; CDCl$_3$): δ=3.94 (s, 3H, —OCH$_3$), 7.37-7.50 (m, 3H, —CH—CH—CH—), 7.61-7.69 (m, 4H, —C(COOMe)—CH—CH— and —CH—CH—CH—), 8.09-8.13 (m, 2H, —C(COOMe)—CH—) ppm. $^{13}$C NMR (75.5 MHz; CDCl$_3$): δ=52.3 (1C, —OCH$_3$), 127.2 (2C, —C(COOMe)—CH—CH—), 127.4 (2C, —CH—CH—CH—C—), 128.3 (1C, —C—CH—CH—CH—), 129.0 (1C, —C(COOMe)—), 129.1 (2C, —CH—(CH—CH)$_2$—C—), 130.2 (2C, —C(COOMe)—CH—), 140.1 (1C, —CH—CH—CH—C—), 145.8 (1C, —C(COOMe)—

CH=CH—C—), 167.2 (1C, —COOMe) ppm. HRMS (ESI⁺) calcd. for $C_{14}H_{13}O_2^+$: 213.0910; found: 213.0908.

Example 29: Synthesis of Biaryl Building Blocks of Compounds Against Cognitive Disorders In another experiment, the synthesis of a key building block of a histamine H3 receptor antagonist is performed. Specific examples of histamine H3 receptor antagonist that can be prepared according to the method of the invention e.g., include the active pharmaceutical ingredients A-349821 or ABT 239, A-698418, A-687136, A-688057, JNJ-280566 or their analogues.

Example 29: Methyl 4'-methoxy-[1,1'-biphenyl]-4-carboxylate a. Preparation of 4-(((4-methoxyphenyl)sulfonamido) methyl)benzoate.

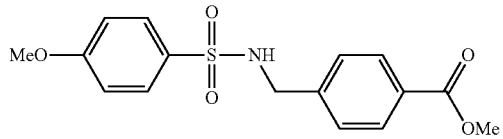 [SMILES: COC(=O)c1ccc(CNS(=O)(=O)c2ccc(OC)cc2)cc1]

A solution of 4-methoxybenzenesulfonyl chloride (206.6 mg, 1 mmol, 1 eq.), methyl 4-(aminomethyl)benzoate hydrochloride (201.7 mg, 1 mmol, 1 eq.) and N,N-diisopropylethylamine (284.4 mg, 383.2 µL, 2.2 mmol, 2.2 eq.) in DCM (4 mL) was stirred for 16 h at room temperature. After dilution with ethyl acetate (20 mL) the solution was washed with water (10 mL), aqueous hydrochloric acid (1 M, 10 mL) and brine (10 mL). The organic layer was dried with sodium sulfate, filtered and the solvent was removed under reduced pressure. The crude product was purified by recrystallization from ethyl acetate which provided the title compound as a white powder (302 mg, 0.9 mmol, 90%)

¹H NMR (300 MHz; CDCl₃): δ=3.86 (s, 3H, —C(OCH₃)), 3.89 (s, 3H, —COOCH₃), 4.17 (d, 2H, $^3J_{HH}$=6.4 Hz, —CH₂—), 4.97 (t, 1H, $^3J_{HH}$=6.4 Hz, —NH—), 6.95 (d, 2H, $^3J_{HH}$=8.9 Hz, —C(OMe)—CH—), 7.27 (d, 2H, $^3J_{HH}$=8.4 Hz, —CH₂—C—CH—), 7.78 (d, 2H, $^3J_{HH}$=8.9 Hz, —C(OMe)—CH—CH—), 7.92 (d, 2H, $^3J_{HH}$=8.4 Hz, —CH₂—C—CH—CH—) ppm. ¹³C NMR (75.5 MHz; CDCl₃): δ=46.8 (1C, —CH₂—), 52.1 (1C, —COOCH₃), 55.6 (1C, —C(OCH₃)), 114.3 (2C, —C(OMe)—CH—), 127.6 (2C, —CH₂—C—CH—), 129.2 (2C, —C(OMe)—CH—CH—), 129.6 (1C, —C(COOMe)), 129.9 (2C, —CH₂—C—CH—CH—), 131.3 (1C, —C—SO₂—), 141.5 (1C, —CH₂—C—), 163.0 (1C, —C(OMe)), 166.6 (1C, —C(O)—OMe) ppm. HRMS (ESI⁺) calcd. for $C_{16}H_{18}NO_5S^+$: 336.0900; found: 336.0895. HRMS (ESI⁻) calcd. for $C_{16}H_{16}NO_5S^-$: 334.0755; found: 334.0755.

b. Preparation of methyl 4'-methoxy-[1,1'-biphenyl]-4-carboxylate.

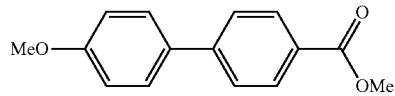 [SMILES: COC(=O)c1ccc(-c2ccc(OC)cc2)cc1]

A solution of methyl 4-(((4-methoxyphenyl)sulfonamido) methyl)benzoate (22.2 mg, 66.2 µmol) in MeOH (10 mL) was loaded on the photo reactor with a flow rate of 1 mL/min (MeOH) and irradiated with UV light at room temperature. The solvent fraction containing the photoproduct was collected and the solvent was removed under vacuum. The residue was purified by open column chromatography to yield the title compound (14.3 mg, 59.0 µmol, 89%).

¹H NMR (300 MHz; CDCl₃): δ=3.86 (s, 3H, —C(OCH₃)—), 3.93 (s, 3H, —COOCH₃), 7.00 (d, 2H, $^3J_{HH}$=8.8 Hz, —CH—C(OMe)—), 7.57 (d, 2H, $^3J_{HH}$=8.8 Hz, —CH—CH—C(OMe)—), 7.62 (d, 2H, $^3J_{HH}$=8.5 Hz, —C(O)—C—CH—CH—), 8.08 (d, 2H, $^3J_{HH}$=8.5 Hz, —C(O)—C—CH—) ppm. ¹³C NMR (75.5 MHz; CDCl₃): δ=47.0 (1C, —COOCH₃), 55.5 (1C, —C(OCH₃)—), 114.5 (2C, —CH—C(OMe)—), 126.6 (2C, —CH—CH—C(OMe)—), 128.3 (1C, —C(COOMe)—), 128.5 (2C, —CH—CH—C(OMe)—), 130.2 (2C, —C(O)—C—CH—), 132.5 (1C, —C—CH—CH—C(OMe)—), 145.3 (1C, —C(COOMe)—CH—CH—C—), 160.0 (1C, —C(OMe)—), 167.2 (1C, —COOMe) ppm. HRMS (ESI⁺) calcd. for $C_{15}H_{15}O_3^+$: 243.1016; found: 243.1024.

Example 30: Synthesis of Biaryl Building Blocks of Anticancer Compounds

In another experiment, the precursor synthesis of the BCL-X$_L$ inhibitor (CAS-Nr.: 406228-29-3) is demonstrated. Specific examples of this group of active substances containing a biaryl group that can be prepared according to the method of the invention e.g., include the BCL-X$_L$ inhibitors WEHI-539, A-1331852, ABT-737, BM-1197 and analogues and/or pharmaceutically acceptable salts thereof.

Example 30: Methyl 4'-fluoro-[1,1'-biphenyl]-4-carboxylate a. Preparation of methyl 4-(((4-fluorophenyl)sulfonamido)methyl)benzoate.

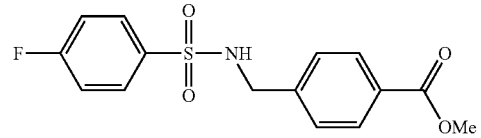 [SMILES: COC(=O)c1ccc(CNS(=O)(=O)c2ccc(F)cc2)cc1]

A solution of 4-fluorobenzenesulfonyl chloride (194.6 mg, 1 mmol, 1 eq.), methyl 4-(aminomethyl)benzoate hydrochloride (201.7 mg, 1 mmol, 1 eq.) and N,N-diisopropylethylamine (284.4 mg, 383.2 µL, 2.2 mmol, 2.2 eq.) in DCM (4 mL) was stirred for 1 h at room temperature. After dilution with ethyl acetate (20 mL) the solution was washed with water (20 mL), aqueous hydrochloric acid (1 M, 20 mL) and brine (20 mL). The organic layer was dried with sodium sulfate, filtered and the solvent was evaporated. The crude product was obtained as a white solid (309.1 mg, 0.96 mmol, 96%) and used without further purification.

¹H NMR (300 MHz; CDCl₃): δ=3.89 (s, 3H, —OCH₃), 4.20 (d, 2H, $^3J_{HH}$=6.2 Hz, —CH₂—), 5.13 (t, 1H, $^3J_{HH}$=6.2 Hz, —NH—), 7.13-7.19 (m, 2H, —SO₂—C—CH—), 7.25-7.28 (d, 2H, $^3J_{HH}$=8.4 Hz, —CH₂—C—CH—), 7.83-7.88 (m, 2H, F—C—CH—), 7.90-7.93 (d, 2H, $^3J_{HH}$=8.4 Hz, —CH—C—COOMe) ppm. ¹³C NMR (75.5 MHz; CDCl₃): δ=47.0 (1C, —CH₂—), 52.4 (1C, —OCH₃), 116.6 (d, 2C, $^3J_{CF}$=22.6 Hz, —SO₂—C—CH—), 127.8 (2C, —CH₂—

C—CH—), 129.9 (1C, —C—COOMe), 130.0 (1C, F—C—CH—), 130.1 (2C, —CH—C—COOMe), 136.0 (d, 1C, $^4J_{CF}$=3.3 Hz, —SO$_2$—C—), 141.3 (1C, —CH$_2$—C—), 165.3 (d, 1C, $^1J_{CF}$=255.7 Hz, F—C—), 167.0 (1C, —C—COOMe) ppm. HRMS (ESI$^+$) calcd. for $C_{15}H_{15}FNO_4S^+$: 324.0700; found: 324.0700. HRMS (ESI$^-$) calcd. for $C_{15}H_{13}FNO_4S^-$: 322.0555; found: 322.0548.

b. Preparation of methyl 4'-fluoro-[1,1'-biphenyl]-4-carboxylate.

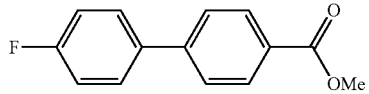 [SMILES: COC(=O)c1ccc(-c2ccc(F)cc2)cc1]

A solution of methyl 4-(((4-fluorophenyl)sulfonamido)methyl)benzoate (22.0 mg, 68.0 µmol) in MeCN (10 mL) was loaded on the photo reactor with a flow rate of 1.5 mL/min (MeCN) and irradiated with UV light at room temperature. The solvent fraction containing the photoproduct was collected and the solvent was removed under vacuum. The residue was purified by open column chromatography to yield the title compound (10.4 mg, 45.2 µmol, 66%).

$^1$H NMR (300 MHz; CDCl$_3$): δ=3.94 (s, 3H, —OCH$_3$), 7.12-7.18 (m, 2H, F—C—CH), 7.56-7.62 (m, 4H, CH—C—C—CH), 8.08-8.11 (m, 2H, CH—C—COOMe) ppm. $^{13}$C NMR (75.5 MHz; CDCl$_3$): δ=52.3 (1C, —OCH$_3$), 116.0 (d, 2C, $^3J_{CF}$=21.6 Hz, F—C—CH—CH—), 127.0 (2C, —CH—CH—C—COOMe), 129.0 (1C, —C—COOMe), 129.1 (d, 2C, F—C—CH—), 130.3 (2C, —CH—C—COOMe), 136.3 (d, 1C, $^4J_{CF}$=3.3 Hz, F—C—CH—CH—C—), 144.7 (1C, —C—CH—CH—C—COOMe), 163.1 (d, 1C, $^1J_{CF}$=245.8 Hz, F—C—), 167.1 (1C, —C—COOMe) ppm. HRMS (ESI$^+$) calcd. for $C_{14}H_{12}FO_2^+$: 231.0816; found: 231.0818. Saponification of methyl 4'-fluoro-[1,1'-biphenyl]-4-carboxylate, followed by carboxylic acid activation (e.g. EDC or thionyl chloride), aminolysis with 4-chloro-3-nitro-benzenesulfonamide and nucleophilic substitution with S-phenyl-cysteamine would yield the BCL-X$_L$ inhibitor given below (CAS: 406228-29-3).

Example 31: Synthesis of Biaryl Building Blocks of Non-Steroidal Antiinflammatory Drugs In another experiment the synthesis of non-steroidal antiinflammatory drugs (NSAIDs) is performed.

The biaryl compound of general formula (I) provides the core structure of different non-steroidal anti-inflammatory or analgesic drugs (NSAIDs). E.g. the active NSAID drugs diflunisal, flurbiprofen, oxaprozin, celecoxib, valdecoxib, parecoxib, etoricoxib, licofelone, felbinac, xenbucin, analogues and/or pharmaceutically acceptable salts thereof may be prepared according to the method of the present invention.

Specific examples e.g., include the active pharmaceutical ingredients biphenylacetic acid (INN: FELBINAC) and/or its α-ethyl derivative (INN: XENBUCIN):

Example 31: Preparation of methyl 2-([1,1'-biphenyl]-4-yl)acetate a. Preparation of methyl 2-(4-(phenylsulfonamidomethyl)phenyl)acetate

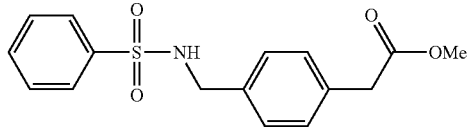 [SMILES: COC(=O)Cc1ccc(CNS(=O)(=O)c2ccccc2)cc1]

A solution of benzenesulfonyl chloride (44.2 mg, 32 µL, 0.25 mmol, 1 eq.), methyl 2-(4-(aminomethyl)phenyl)acetate hydrochloride (53.9 mg, 0.25 mmol, 1 eq.) and N,N-diisopropylethylamine (71.1 mg, 95.8 µL, 0.55 mmol, 2.2 eq.) in DCM (1 mL) was stirred for 8 h at room temperature. After dilution with ethyl acetate (20 mL) the solution was washed with water (20 mL), aqueous hydrochloric acid (1 M, 20 mL) and brine (20 mL). The organic layer was dried with sodium sulfate, filtered and the solvent was evaporated. The crude product was obtained as white solid (70.9 mg, 0.22 mmol, 89%) and used without further purification.

$^1$H NMR (300 MHz; CDCl$_3$): δ=3.58 (s, 2H, —CH$_2$—C(O)—), 3.67 (s, 3H, —OCH$_3$), 4.12 (d, 2H, $^3J_{HH}$=6.0 Hz, —NH—CH$_2$—), 4.83 (t, 1H, $^3J_{HH}$=6.0 Hz, —NH—), 7.12-7.17 (m, 4H, —CH$_2$—C—CH—CH—C—CH$_2$—), 7.47-7.54 (m, 2H, —CH—CH—CH—CH—C—SO$_2$—), 7.55-7.61 (m, 1H, —CH—CH—CH—CH—C—SO$_2$—), 7.85-7.88 (m, 2H, —CH—C—SO$_2$—) ppm. $^{13}$C NMR (75.5 MHz; CDCl$_3$): δ=40.9 (1C, —CH$_2$—C(O)—), 47.1 (1C, —NH—CH$_2$—), 52.2 (1C, —OCH$_3$), 127.2 (2C, —CH—C—SO$_2$—), 128.2 (2C, —NH—CH$_2$—C—CH—), 129.3 (2C, —CH—CH—CH—CH—C—SO$_2$—), 129.8 (2C, —CH—C—CH$_2$—C(O)—), 132.8 (1C, —CH—CH—CH—CH—C—SO$_2$—), 133.9 (1C, —C—CH$_2$—C(O)—), 135.3 (1C, —NH—CH$_2$—C—), 140.1 (1C, —C—SO$_2$—), 171.9 (1C, —COOMe) ppm. HRMS (ESI$^+$) calcd. for $C_{16}H_{18}NO_4S^+$: 320.0951; found: 320.0947. HRMS (ESI$^-$) calcd. for $C_{16}H_{16}NO_4S^-$: 318.0806; found: 318.0802.

b. Preparation of methyl 2-([1,1'-biphenyl]-4-yl)acetate

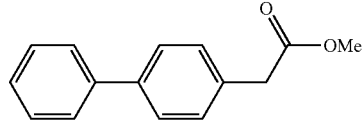 [SMILES: COC(=O)Cc1ccc(-c2ccccc2)cc1]

A solution of methyl 2-(4-(phenylsulfonamidomethyl)phenyl)acetate (19.7 mg, 61.7 µmol) in MeOH (10 mL) was loaded on the photo reactor with a flow rate of 0.5 mL/min (MeOH) and irradiated with UV light at room temperature. The solvent fraction containing the photoproducts was collected and the solvent was removed under vacuum. The residue was purified by open column chromatography to yield the title compound (6.7 mg, 29.6 µmol, 48%).

$^1$H NMR (500 MHz; CDCl$_3$): δ=3.68 (s, 2H, —CH$_2$—), 3.72 (s, 3H, —OCH$_3$), 7.33-7.37 (m, 3H, (—CH—CH—C—CH$_2$— and —C—CH—CH—CH—CH—), 7.42-7.45 (m, 2H, —C—CH—CH—CH—CH—), 7.55-7.59 (m, 4H, —CH—C—CH$_2$— and CH—C—C—) ppm. $^{13}$C NMR (125.8 MHz; CDCl$_3$): δ=41.0 (1C, —CH$_2$—), 52.3 (1C, —OCH$_3$), 127.2 (2C, —C—CH—CH—CH—CH—CH—), 127.4 (1C, —C—CH—CH—CH—CH—

CH—), 127.5 (2C, —CH—CH—C—CH$_2$—), 128.9 (2C, —C—CH—CH—CH—CH—CH—), 129.8 (2C, —CH—C—C—CH$_2$—), 133.1 (1C, —C—CH$_2$—), 140.3 (1C, —C—C—CH—CH—C—), 140.9 (1C, —C—CH—CH—CH—CH—CH—), 172.2 (1C, —C(O)—) ppm. HRMS (ESI$^+$) calcd. for C$_{15}$H$_{15}$O$_2$$^+$: 227.1067; found: 227.1073.

Saponification (basic hydrolysis) of 2-([1,1'-biphenyl]-4-yl)acetate would lead to felbinac. Felbinac would be transformed to xenbucin through deprotonation (e.g. n-butyllithium) and subsequent nucleophilic substitution of an ethylating agent (e.g. ethyl iodide).

Example 32: Total Synthesis of Cannabinol

Finally, we envisaged the use of the photosplicing method according to the invention in a total synthesis of the biarylic natural product cannabinol (6,6,9-trimethyl-3-pentyl-6H-benzo[c]chromen-1-ol) of formula

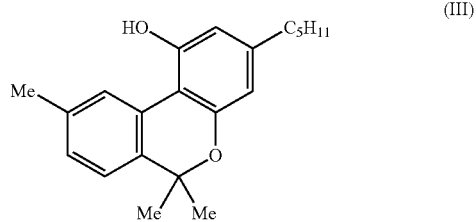

(III)

This non-psychoactive cannabinoid is a valuable therapeutic agent that is only produced in trace amounts by *Cannabis*.[19, 20] Yet, because of its analgesic and antiemetic properties, there is a high demand for pure cannabinol, which has propelled numerous total synthesis approaches.

A metal-free photosplicing route towards the cannabinol biaryl scaffold would require a highly substituted precursor. To test the feasibility of the aryl coupling in the presence of multiple ortho-substituents adjacent to the sulfonamide tether we first used model substrate with bulky benzyloxy substituents which smoothly produced the corresponding biphenyl in a good yield (67%, see Table 1, Example 16). Encouraged by this result, the bis-ortho-substituted sulfonamide required for cannabinol synthesis was assembled from 2-cyano-5-methylbenzenesulfonyl chloride and 2,6-dimethoxy-4-pentylbenzylamine. The synthesis started with bis-methylation and carboxylation of olivetol by directed ortho-metallation, followed by the amidation with ammonia gas and reduction with lithium aluminium hydride to yield the 2,6-dimethoxy-4-pentylbenzylamine. Without further purification, the amine was tethered to commercially available 2-cyano-5-methylbenzenesulfonyl chloride, and the resulting 2-Cyano-N-(2,6-dimethoxy-4-pentylbenzyl)-5-methylbenzene-sulfonamide was subjected to the photoreaction to give the desired biphenyl (2',6'-Dimethoxy-5-methyl-4'-pentyl-[1,1'-biphenyl]-2-carbonitrile) in excellent yield (93%). Heating with concentrated hydriodic acid in acetic acid resulted in the demethylation of both phenolic hydroxy groups, nitrile hydrolysis and lactonization in a one-pot reaction (67%). The obtained benzochromenone (1-Hydroxy-9-methyl-3-pentyl-6H-benzo[c]chromen-6-one) was then quantitatively converted into cannabinol by methyllithium using a modified version of an established protocol.[22]

a. Preparation of 1,3-dimethoxy-5-pentylbenzene (dimethoxy olivetol).

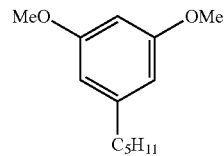

1,3-Dimethoxy-5-pentylbenzene (dimethoxy olivetol) was synthesized according to previously published protocol.[21] To a suspension of olivetol (3 g, 16.6 mmol, 1 eq.) and potassium carbonate (6.9 g, 49.9 mmol, 3 eq.) in 30 mL dried acetone dimethyl sulfate (6.3 g, 49.9 mmol, 3 eq.) was added slowly at room temperature and heated at 60° C. for 12 h. The mixture was cooled, filtered and diluted with diethyl ether. The organic phase was washed with 1 M HCl aq. (10 mL), water (10 mL) and brine (10 mL), dried with sodium sulfate and concentrated. The crude liquid colorless product was purified by vacuum distillation (boiling point: 90° C., 0.05 mbar) to yield 2.66 g (12.78 mmol, 77%) of the desired product.

$^1$H NMR (300 MHz; CDCl$_3$): δ=0.89 (t, 3H, $^3J_{HH}$=6.9 Hz, CH$_3$—CH$_2$), 1.30-1.36 (m, 4H, CH$_3$—CH$_2$—CH$_2$—), 1.56-1.66 (m, 2H, CH$_3$—CH$_2$—CH$_2$—CH$_2$—), 2.54 (t, 2H, $^3J_{HH}$=7.7 Hz, —CH$_2$—Ar), 3.78 (s, 6H, —OCH$_3$), 6.30 (t, 1H, $^4J_{HH}$=2.3 Hz, —C(OCH$_3$)—CH—C(OCH$_3$)—), 6.35 (d, 2H, $^4J_{HH}$=2.3 Hz, —C(OCH$_3$)—CH—C(C$_5$H$_{11}$)—) ppm. $^{13}$C NMR (75.5 MHz; CDCl$_3$): δ=14.2 (1C, CH$_3$—CH$_2$—), 22.7 (1C, CH$_3$—CH$_2$—), 31.1 (1C, CH$_3$—CH$_2$—CH$_2$—), 31.7 (1C, CH$_3$—CH$_2$—CH$_2$—CH$_2$—), 36.4 (1C, —CH$_2$—Ar), 55.4 (2C, —OCH$_3$), 97.7 (1C, —C(OCH$_3$)—CH—C(OCH$_3$)—), 106.6 (2C, —C(OCH$_3$)—CH—C(C$_5$H$_{11}$)—), 145.6 (1C, —C(C$_5$H$_{11}$)—), 160.8 (2C, —C(OCH$_3$)—) ppm. HRMS (ESI$^+$) calcd. for C$_{13}$H$_{21}$O$_2$$^+$: 209.1536; found: 209.1539.

b. Preparation of 2,6-dimethoxy-4-pentylbenzoic acid.

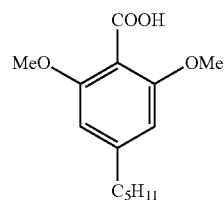

n-Butyllithium (1.6 M in hexanes, 3.58 mL, 5.72 mmol, 1.1 eq.) was added slowly at 0° C. to a solution of 1,3-dimethoxy-5-pentylbenzene (1.08 g, 5.2 mmol, 1 eq.) and tetramethylethylenediamine (1.17 mL, 7.8 mmol, 1.5 eq.) in 20 mL dried diethyl ether under argon. Dry ice (0.44 g, 10.4 mmol; 2 eq.) was added and the mixture was allowed to warm up to room temperature overnight. The mixture was filtered and diluted with ethyl acetate. The organic phase was washed with 1 M HCl aq. (10 mL), water (10 mL) and brine (10 mL), dried with sodium sulfate and concentrated. The crude product (1.29 g, 5.11 mmol, 98%, white crystalline solid) was used without further purification.

$^1$H NMR (500 MHz; DMSO-d6): δ=0.87 (t, 3H, $^3J_{HH}$=7.0 Hz, CH$_3$—CH$_2$), 1.26-1.32 (m, 4H, CH$_3$—CH$_2$—CH$_2$—), 1.54-1.60 (m, 2H, CH$_3$—CH$_2$—CH$_2$—CH$_2$—), 2.52 (m, 2H, —CH$_2$—Ar), 3.67 (s, 6H, —OCH$_3$), 6.40 (s, 2H, —C(OCH$_3$)—CH—C(C$_5$H$_{11}$)—) ppm. $^{13}$C NMR (125.8 MHz; DMSO-d6): δ=14.0 (1C, CH$_3$—CH$_2$—), 22.0 (1C, CH$_3$—CH$_2$—), 30.7 (1C, CH$_3$—CH$_2$—CH$_2$—), 31.0 (1C, CH$_3$—CH$_2$—CH$_2$—CH$_2$—), 35.7 (1C, —CH$_2$—Ar), 55.4 (2C, —OCH$_3$), 104.2 (2C, —C(OCH$_3$)—CH—C(C$_5$H$_{11}$)—), 129.7 (1C, —C(COOH)—), 142.5 (1C, —C(C$_5$H$_{11}$)—), 155.5 (2C, —C(OCH$_3$)—), 167.8 (1C, COOH) ppm. HRMS (ESI$^+$) calcd. for C$_{14}$H$_{21}$O$_4{}^+$: 253.1434; found: 253.1434. HRMS (ESI$^-$) calcd. for C$_{14}$H$_{19}$O$_4{}^-$: 251.1289; found: 251.1293 c. Preparation of 2,6-dimethoxy-4-pentylbenzamide

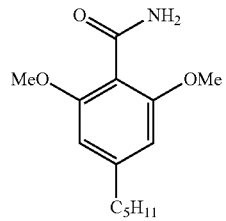

2,6-Dimethoxy-4-pentylbenzoic acid (1.29 g, 5.11 mmol, 1 eq.) was dissolved in 20 mL dried toluene, oxalyl chloride (437 μL, 5.11 mmol, 1 eq.) and a catalytic amount of DMF (2 drops) were added. After approximately one hour gas evolution stopped and the solution was stirred for another hour. The mixture was filtered and the solvents were removed under reduced pressure. Crude acid chloride (1.16 g) was dissolved in 20 mL dried THF and gaseous ammonia was bubbled into the solution for 15 min. The mixture was diluted with diethyl ether, the organic layer was washed with 1 M HCl aq. (20 mL), water (20 mL) and brine (20 mL), dried with sodium sulfate and concentrated. The crude product was purified by recrystallization from toluene/cyclohexane (v/v=1/1) to provide the title compound as a white crystalline compound (527 mg, 2.10 mmol, 41% over 2 steps).

$^1$H NMR (500 MHz; DMSO-d6): δ=0.88 (t, 3H, $^3J_{HH}$=7.0 Hz, CH$_3$—CH$_2$), 1.27-1.35 (m, 4H, CH$_3$—CH$_2$—CH$_2$—), 1.55-1.61 (m, 2H, CH$_3$—CH$_2$—CH$_2$—CH$_2$—), 2.54 (t, $^3J_{HH}$=7.7 Hz, 2H, —CH$_2$—Ar), 3.71 (s, 6H, —OCH$_3$), 6.47 (s, 2H, —C(OCH$_3$)—CH—C(C$_5$H$_{11}$)—), 7.08 (s, 1H, —NH$_2$), 7.37 (s, 1H, —NH$_2$) ppm. $^{13}$C NMR (125.8 MHz; DMSO-d6): δ=13.9 (1C, CH$_3$—CH$_2$—), 21.9 (1C, CH$_3$—CH$_2$—), 30.6 (1C, CH$_3$—CH$_2$—CH$_2$—CH$_2$), 31.0 (1C, CH$_3$—CH$_2$—CH$_2$—CH$_2$—), 35.8 (1C, —CH$_2$—Ar), 55.4 (2C, —OCH$_3$), 104.1 (2C, —C(OCH$_3$)—CH—C(C$_5$H$_{11}$)—), 114.9 (1C, —C(CONH$_2$)—), 144.4 (1C, —C(C$_5$H$_{11}$)—), 156.2 (2C, —C(OCH$_3$)—), 166.7 (1C, C=O) ppm. HRMS (ESI$^+$) calcd. for C$_{14}$H$_{22}$NO$_3{}^+$: 252.1594; found: 252.1593.

d. Preparation of 2-cyano-N-(2,6-dimethoxy-4-pentylbenzyl)-5-methylbenzene-sulfonamide.

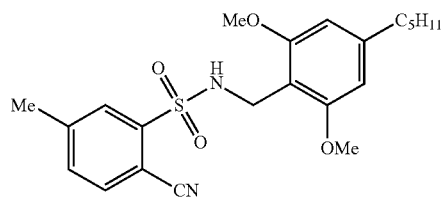

2,6-Dimethoxy-4-pentylbenzamide (300 mg, 1.2 mmol, 1 eq.) was dissolved in 50 mL dried THF and lithium aluminium hydride (450 mg, 12 mmol, 10 eq.) was added. The mixture was heated under reflux and reaction was monitored by TLC. Heating was stopped when no more benzamide was present (about 30 min). The mixture was diluted with ethyl acetate, the organic layer was washed with 1 M NaOH aq. (20 mL), water (2×20 mL) and brine (20 mL), dried with sodium sulfate and concentrated to yield crude benzylamine as a yellow oil (277 mg, 1.17 mmol). This benzylamine was used immediately without further purification for following sulfonamide coupling. The benzylamine and 2-cyano-5-methylbenzenesulfonyl chloride (250 mg, 1.16 mmol) were dissolved in 20 mL dried THF, N,N-diisopropylethylamine (458.8 mg, 618.4 μL, 3.55 mmol, 3 eq.) was added and the mixture was stirred for 2 hours at room temperature. The solvent was removed under reduced pressure and the residue was taken up in ethyl acetate. The organic layer was washed with water (2×20 mL) and brine (20 mL), dried with sodium sulfate, concentrated and purified by preparative column chromatography (ethyl acetate/cyclohexane (v/v=1/4) containing 0.1% acetic acid, R$_f$=0.26) to yield 389 mg (0.93 mmol, 78% relative to benzamide) of the desired sulfonamide as a white amorphous solid.

$^1$H NMR (300 MHz; CDCl$_3$): δ=0.91 (t, 3H, $^3J_{HH}$=7.0 Hz, CH$_3$—CH$_2$), 1.25-1.39 (m, 4H, CH$_3$—CH$_2$—CH$_2$—), 1.46-1.56 (m, 2H, CH$_3$—CH$_2$—CH$_2$—CH$_2$—), 2.42-2.47 (m, 2H, —CH$_2$—Ar), 2.43 (s, 3H, —C(CH$_3$)—), 3.69 (s, 6H, —OCH$_3$), 4.29 (d, 2H, $^3J_{HH}$=6.4 Hz, CH$_2$—NH), 5.96 (t, 1H, $^3J_{HH}$=6.4 Hz, —NH—), 6.08 (s, 2H, —C(OCH$_3$)—CH—C(C$_5$H$_{11}$)—), 7.21-7.26 (s, 1H, —C(CH$_3$)—CH—CH—), 7.32-7.35 (s, 1H, —CH—C(CN)—), 7.84 (s, 1H, —CH—C(SO$_2$)—) ppm. $^{13}$C NMR (75.5 MHz; CDCl$_3$): δ=14.2 (1C, CH$_3$—CH$_2$—), 21.9 (1C, —C(CH$_3$)—), 22.7 (1C, CH$_3$—CH$_2$—), 31.3 (1C, CH$_3$—CH$_2$—CH$_2$—CH$_2$), 31.6 (1C, CH$_3$—CH$_2$—CH$_2$—CH$_2$—), 36.5 (1C, —NH—CH$_2$—), 36.7 (1C, C$_4$H$_9$—CH$_2$—), 55.5 (2C, —OCH$_3$), 103.2 (2C, —C(OCH$_3$)—CH—C(C$_5$H$_{11}$)—), 106.9 (1C, —C(CN)—), 109.2 (1C, —C(CH$_2$—NH—)—), 116.2 (1C, —CN), 130.8 (1C, —CH—C(SO$_2$)—), 132.1 (1C, —C(CH$_3$)—CH—CH—), 133.9 (1C, —CH—C(CN)—), 143.2 (1C, —C(SO$_2$)—), 143.5 (1C, —C(CH$_3$)—), 145.1 (1C, —C(C$_5$H$_{11}$)—), 157.5 (2C, —C(OCH$_3$)—) ppm. HRMS (ESI$^+$) calcd. for C$_{22}$H$_{29}$N$_2$O$_4$S$^+$: 417.1843; found: 417.1840.

e. Preparation of 2',6'-dimethoxy-5-methyl-4'-pentyl-[1,1'-biphenyl]-2-carbonitrile.

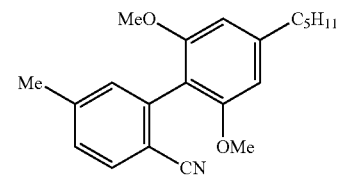

A solution of 2-cyano-N-(2,6-dimethoxy-4-pentylbenzyl)-5-methylbenzenesulfonamide (50 mg, 120 μmol) in MeOH (10 mL) was loaded on the photo reactor (layer thickness 0.3 mm) with a flow rate of 2 mL/min (MeOH) and irradiated with UV light (90 W, 254 nm) at room temperature. The solvent fraction containing the photoproducts was collected and the solvent was removed under vacuum. The residue was dissolved in DCM, filtered and purified by open column chromatography (DCM/cyclohexane (v/v=1/1), R$_f$=0.38) to yield the title compound (36 mg, 111.3 μmol, 93%) as a white amorphous solid.

$^1$H NMR (300 MHz; CDCl$_3$): δ=0.91-0.95 (m, 3H, CH$_3$—CH$_2$), 1.31-1.45 (m, 4H, CH$_3$—CH$_2$—CH$_2$—), 1.63-1.73 (m, 2H, CH$_3$—CH$_2$—CH$_2$—CH$_2$—), 2.63 (t, 2H, $^3J_{HH}$=7.8 Hz, —CH$_2$—Ar), 2.42 (s, 3H, —C(CH$_3$)—), 3.76 (s, 6H, —OCH$_3$), 6.48 (s, 2H, —C(OCH$_3$)—CH—C(C$_5$H$_{11}$)—), 7.16-7.17 (s, 1H, —C(CH$_3$)—CH—CH—), 7.20-7.21 (s, 1H, —CH—C(CH$_3$)—), 7.60 (d, 1H, $^3J_{HH}$=7.8 Hz, —CH—C(CN)—) ppm. $^{13}$C NMR (75.5 MHz; CDCl$_3$): δ=14.2 (1C, CH$_3$—CH$_2$—), 22.0 (1C, —C(CH$_3$)—), 22.7 (1C, CH$_3$—CH$_2$—), 31.2 (1C, CH$_3$—CH$_2$—CH$_2$—CH$_2$), 31.8 (1C, CH$_3$—CH$_2$—CH$_2$—CH$_2$—), 37.0 (1C, C$_4$H$_9$—CH$_2$—), 56.0 (2C, —OCH$_3$), 104.5 (2C, —C(OCH$_3$)—CH—C(C$_5$H$_{11}$)—), 111.7 (1C, —C(CN)—), 113.3 (1C, —C(OCH$_3$)—CH—C(OCH$_3$)—), 119.3 (1C, —CN), 128.1 (1C, —C(CH$_3$)—CH—CH—), 132.5 (1C, —C(CH$_3$)—CH—C(C)—), 133.1 (1C, —CH—C(CN)—), 138.9 (1C, —C(C)—C(CN)—), 142.7 (1C, —C(CH$_3$)—), 145.9 (1C, —C(C$_5$H$_{11}$)—), 157.4 (2C, —C(OCH$_3$)—) ppm. HRMS (ESI$^+$) calcd. for C$_{21}$H$_{26}$NO$_2^+$: 324.1958; found: 324.1961.

f. Preparation of 1-hydroxy-9-methyl-3-pentyl-6H-benzo[c]chromen-6-one.

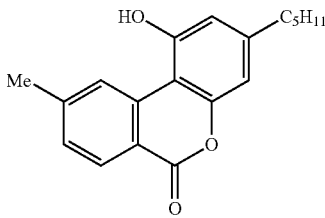

A solution of crude biphenyl photoproduct (90 mg, 90% purity (determined by HPLC) ≙ 250.4 μmol) was dissolved in 1 mL acetic acid, 1 mL 57% hydroiodic acid aq. was added and the mixture was heated at 120° C. for 4 hours. The reaction was stopped, cooled to room temperature and diluted with ethyl acetate. The organic layer was washed with aqueous sodium sulfite solution (2×10 mL, 1 M), water (10 mL) and dried with sodium sulfate. Solvents were removed under reduced pressure. The residue was filtered over silica with DCM (R$_f$=0.9) to yield the pure title compound (49.5 mg, 167 82 mol, 67%) as an orange oil.

$^1$H NMR (300 MHz; CDCl$_3$): δ=0.87-0.92 (m, 3H, CH$_3$—CH$_2$), 1.29-1.34 (m, 4H, CH$_3$—CH$_2$—CH$_2$—), 1.62-1.67 (m, 2H, CH$_3$—CH$_2$—CH$_2$—CH$_2$—), 2.54 (s, 3H, —C(CH$_3$)—), 2.61 (t, 2H, $^3J_{HH}$=7.7 Hz, —CH$_2$—Ar), 6.26 (s, 1H, —OH), 6.63 (s, 1H, $^4J_{HH}$=1.6 Hz, —C(OH)—CH—), 6.80 (d, 1H, $^4J_{HH}$=1.6 Hz, —C(C$_5$H$_{11}$)—CH—), 7.36 (d, 1H, $^3J_{HH}$=8.0 Hz, —C(CH$_3$)—CH—CH—), 8.26 (d, 1H, $^3J_{HH}$=8.0 Hz, —CH—C(CO)—), 8.84 (s, 1H, —C(CH$_3$)—CH—) ppm. $^{13}$C NMR (75.5 MHz; CDCl$_3$): δ=14.2 (1C, CH$_3$—CH$_2$—), 22.7 (1C, CH$_3$—CH$_2$—), 22.9 (1C, —C(CH$_3$)—), 30.8 (1C, CH$_3$—CH$_2$—CH$_2$—CH$_2$), 31.8 (1C, CH$_3$—CH$_2$—CH$_2$—CH$_2$—), 35.8 (1C, C$_4$H$_9$—CH$_2$—), 105.2 (1C, —C(OH)—C(C)—), 110.1 (1C, —CH—C(C$_5$H$_{11}$)—), 112.6 (1C, —C(OH)—CH—), 118.4 (1C, —C—C(O)—), 127.7 (1C, —C(CH$_3$)—CH—C—), 129.2 (1C, —C(CH$_3$)—CH—CH—), 130.2 (1C, —CH—C(CO)—), 135.1 (1C, —C(CH$_3$)—CH—C—)), 146.2 (1C, —C(C$_5$H$_{11}$)—), 146.4 (1C, —C(CH$_3$)—), 153.2 (1C, C(O)—O—C—), 154.7 (1C, —C(OH)—), 162.0 (1C, CO) ppm. HRMS (ESI$^+$) calcd. for C$_{19}$H$_{21}$O$_3^+$: 297.1485; found: 297.1492. HRMS (ESI$^-$) calcd. for C$_{19}$H$_{19}$O$_3^-$: 295.1340; found: 295.1347.

g. Preparation of the Target Molecule Cannabinol (6,6,9-trimethyl-3-pentyl-6H-benzo[c]chromen-1-ol) in Analogy to an Established Protocol.[22]

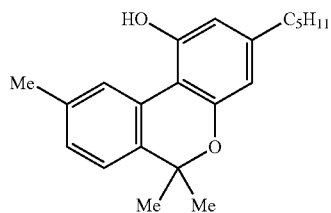

Methyllithium (1.6 M in diethyl ether, 631 μL, 1.01 mmol, 10 eq.) was added to dried THF (2 mL) at −78° C. under argon. 1-Hydroxy-9-methyl-3-pentyl-6H-benzo[c]chromen-6-one (30 mg, 0.101 mmol, 1 eq.) was dissolved in dried THF (2 mL) and the solution was added slowly. The solution was allowed to warm up to room temperature overnight. The reaction was quenched by the addition of ammonium chloride (sat. aq.) at 0° C. The mixture was extracted with ethyl acetate (3×10 mL), the organic layer was washed with brine (2×10 mL), dried with sodium sulfate and concentrated. The colorless residue was dissolved in dried DCM (10 mL), trifluoroacetic acid (100 μL) was added and the orange colored mixture was stirred for 1 hour. The reaction was stopped by dilution with ethyl acetate. The organic layer was washed with sodium bicarbonate (sat. aq.; 10 mL), water (10 mL) and brine (10 mL), dried with sodium sulfate and concentrated. The crude product was purified by open column chromatography (ethyl acetate/cyclohexane (v/v=6/94), R$_f$=0.33) to yield the desired product as orange oil (30.9 mg, 99.5 μmol, 99%).

$^1$H NMR (500 MHz; CDCl$_3$): δ=0.89 (t, 3H, $^3J_{HH}$=6.8 Hz, CH$_3$—CH$_2$), 1.31-1.33 (m, 4H, CH$_3$—CH$_2$—CH$_2$—), 1.60 (s, 6H, —(H$_3$C)C(CH$_3$)—), 1.61-1.64 (m, 2H, CH$_3$—CH$_2$—CH$_2$—CH$_2$—), 2.38 (s, 3H, —C(CH$_3$)—), 2.50 (t, 2H, $^3J_{HH}$=7.7 Hz, —CH$_2$—Ar), 5.08 (br, 1H, —OH), 6.29 (s, 1H, —C(OH)—CH—C(C$_5$H$_{11}$)—), 6.44 (s, 1H, —C—CH—C(C$_5$H$_{11}$)—), 7.07 (d, 1H, $^3J_{HH}$=7.8 Hz, —C(CH$_3$)—CH—CH—), 7.15 (d, 1H, $^3J_{HH}$=7.8 Hz, —C(CH$_3$)—CH—CH—), 8.15 (s, 1H, —C(CH3)—CH—C(C)—) ppm. $^{13}$C NMR (125.8 MHz; CDCl$_3$): δ=14.2 (1C, CH$_3$—CH$_2$—), 21.7 (1C, —C(CH$_3$)—), 22.7 (1C, CH$_3$—CH$_2$—), 27.3 (2C, —(H$_3$C)C(CH$_3$)—), 30.6 (1C, CH$_3$—CH$_2$—CH$_2$—CH$_2$), 31.6 (1C, CH$_3$—CH$_2$—CH$_2$—CH$_2$—), 35.8 (1C, C$_4$H$_9$—CH$_2$—), 77.5 (1C, —(H$_3$C)C(CH$_3$)—) 108.9 (1C, —C(OH)—C(C)—), 110.0 (1C, —C(CH$_3$)—CH—C—), 110.0 (1C, —C(OH)—CH—C(C$_5$H$_{11}$)—), 111.0 (1C, —C—CH—C(C$_5$H$_{11}$)—), 122.8 (1C, —C(CH$_3$)—CH—CH—), 126.5 (1C, —C(CH$_3$)—CH—C(C)—), 127.7 (1C, —(CH$_3$)C—), 127.8 (1C, —C(CH$_3$)—CH—CH—), 137.1 (1C, C—C(CH$_3$)$_2$—), 144.7 (1C, —C(C$_5$H$_{11}$)—), 153.1 (1C, —C(O)—), 154.8 (1C, —C(OH)—) ppm. HRMS (ESI$^+$) calcd. for C$_{21}$H$_{27}$O$_2^+$: 311.2006; found: 311.2007. HRMS (ESI$^-$) calcd. for C$_{21}$H$_{25}$O$_2^-$: 309.1860; found: 309.1859.

Examples 33-39: Modifications of the Linker

The following examples were prepared in analogy to example 1b with minor variations of reaction parameters. Educts were prepared by means of standard procedures known to the skilled person.

| Educt | Example | Yield [%] | Product |
|---|---|---|---|
| (4-MeC₆H₄)SO₂N(Me)CH₂-C₆H₄-COOMe | 33 | 54 | 4-Me-C₆H₄-C₆H₄-COOMe |
| (4-MeC₆H₄)SO₂NH-C(cyclopropyl)-C₆H₄-COOMe | 34 | 20 | |
| (4-MeC₆H₄)SO₂NH-C(Me)₂-C₆H₄-COOMe | 35 | 62 | |
| (4-MeC₆H₄)SO₂-N(SO₂-4-MeC₆H₄)-CH₂-C₆H₄-COOMe | 36 | 84 | |
| (4-MeC₆H₄)SO₂-O-CH₂-C₆H₄-COOMe | 37 | 31 | |
| (4-MeC₆H₄)SO₂-CH₂CH₂-C₆H₄-COOMe | 38 | 13 | |
| (C₆H₅SO₂)₂N-CH₂-C₆H₄-COOMe | 39 | 72 | C₆H₅-C₆H₄-COOMe |

REFERENCES 1 a) Welsch, M. E., Snyder, S. A. & Stockwell, B. R. Privileged Scaffolds for Library Design and Drug Discovery. *Curr. Opin. Chem. Biol.* 14, 347-361, (2010).

b) Horton, D. A., Bourne, G. T. & Smythe, M. L. The Combinatorial Synthesis of Bicyclic Privileged Structures or Privileged Substructures. *Chem. Rev.* 103, 893-930 (2003).

2 Johansson Seechurn, C. C. C., Kitching, M. O., Colacot, T. J. & Scnieckus, V. Palladium-Catalyzed Cross-Coupling: A Historical Contextual Perspective to the 2010 Nobel Prize. *Angew. Chem. Int. Ed.* 51, 5062-5085, (2012).

3 Goossen, L. J., Deng, G. & Levy, L. M. Synthesis of Biaryls via Catalytic Decarboxylative Coupling. *Science* 313, 662-664, (2006).

4 Ackerman, L. K., Lovell, M. M. & Weix, D. J. Multimetallic catalysed cross-coupling of aryl bromides with aryl triflates. *Nature* 524, 454-457, (2015).

5 Rodriguez, N. & Goossen, L. Decarboxylative coupling reactions: a modern strategy for C—C-bond formation. *Chem. Soc. Rev.* 40, 5030-5048, (2011).

6 Sun, C. L. & Shi, Z. J. Transition-Metal-Free Coupling Reactions. *Chem. Rev.* 114, 9219-9280, (2014).

7 De Carolis, M, Protti, S., Fagnoni, M. & Albini, A. Metal-Free Cross-Coupling Reactions of Aryl Sulfonates and Phosphates through Photoheterolysis of Aryl-Oxygen Bonds. *Angew. Chem. Int. Ed.* 44, 1258-1262, (2005).

8 Dichiarante, V., Fagnoni, M. & Albini, A. Metal-Free Synthesis of Sterically Crowded Biphenyls by Direct Ar—H Substitution in Alkyl Benzenes. *Angew. Chem. Int. Ed.* 46, 6495-6498, (2007).

9 Hari, D. D., Schroll, P. & König, B. Metal-Free, Visible-Light-Mediated Direct C—H Arylation of Heteroarenes with Aryl Diazonium Salts. *J. Am. Chem. Soc.* 134, 2958-2961, (2012).

10 Shirakawa, E. et al. Cross-coupling of aryl Grignard reagents with aryl iodides and bromides through S(RN)1 pathway. *Angew. Chem. Int. Ed.* 51, 218-221, (2012).

11 Dohi, T. et al. Unusual ipso substitution of diaryliodonium bromides initiated by a single-electron-transfer oxidizing process. *Angew. Chem. Int. Ed.* 49, 3334-3337, (2010).

12 Ito, M. et al. Organocatalytic C—H/C—H' cross-biaryl coupling: C-selective arylation of sulfonanilides with aromatic hydrocarbons. *J. Am. Chem. Soc.* 135, 14078-14081, (2013).

13 Elsler, B., Schollmeyer, D., Dyballa, K. M., Franke, R. & Waldvogel, S. R. Metal- and reagent-free highly selective anodic cross-coupling reaction of phenols. *Angew. Chem. Int. Ed.* 53, 5210-5213, (2014).

14 Sun, C. L. et al. An efficient organocatalytic method for constructing biaryls through aromatic C—H activation. *Nat. Chem.* 2, 1044-1049, (2010).

15 Allart-Simon, I., Gérard, S. & Sapi, J. Radical Smiles Rearrangement: An Update. *Molecules* 21, 878, (2016).

16 Holden, C. M., Sohel, S. M. A. & Greaney, M. F. Metal Free Bi(hetero)aryl Synthesis: A Benzyne Truce-Smiles Rearrangement. *Angew. Chem. Int. Ed.* 55, 2450-2453, (2016).

17 Corbet, J. P. & Mignani, G. Selected patented cross-coupling reaction technologies. *Chem. Rev.* 106, 2651-2710, (2006)

18 Weiss, B., Dürr, H. & Haas, H. J. Photochemistry of Sulfonamides and Sulfonylureas: A Contribution to the Problem of Light-Induced Dermatoses. *Angew. Chem. Int. Ed.* 19, 648-650 (1980).

19 Pop, E. Cannabinoids, endogenous ligands and synthetic analogs. *Curr. Opin. Chem. Biol.* 3, 418-425, (1999).

20 Turner, S. E., Williams, C. M., Iversen, L. & Whalley, B. J. Molecular Pharmacology of Phytocannabinoids. *Prog. Chem. Org. Nat. Prod.* 103, 61-101, (2017).

21 Trost, B. M., Dogra, K. Synthesis of (−)-Δ$^9$-trans-Tetrahydrocannabinol: Stereocontrol via Mo-Catalyzed Asymmetric Allylic Alkylation Reaction. *Org. Lett.* 9, 861-863, (2007).

22 Nüllen, M. P., Göttlich, R. Synthesis of Cannabinol by a Modified Ullmann-Ziegler Cross-Coupling. *Synlett* 24, 1109-1112, (2013).

The invention claimed is:

1. A method for the regiocontrolled preparation of a biaryl compound of general formula (I) by photochemically reacting a precursor compound of general formula (II) to form a biaryl compound of general formula (I)

wherein

Ar and Ar', independently of each other, represent an unsubstituted or substituted $C_6$-$C_{20}$ aryl group or an unsubstituted or substituted heteroaryl group with 5-20 ring atoms selected from carbon, nitrogen, oxygen, sulfur, C=O and C=S and L represents a group —X—Y—Z— wherein X, Y, Z are independently of each other selected from

X=$SO_2$, (P=O)$OR^1$, or $SiR^2R^3$,

Y=$NR^4$, O, or $CR^5R^6$,

Z=$CR^7R^8$, wherein $R^1$ is hydrogen, an unsaturated or saturated, linear, branched or cyclic $C_1$-$C_{12}$ aliphatic radical that can be substituted by 1-5 same or different substituent(s), a phenyl or benzyl group, $R^2$, $R^3$ are independently of each other a $C_6$-$C_{20}$ aryl that can be substituted by 1-5 same or different substituents, a 5-20 membered heteroaryl comprising 1 to 5 same or different heteroatoms or heteroatom groups selected from N, O, S, C=O or C=S that can be substituted by 1-5 same or different substituents, or an unsaturated or saturated, linear, branched or cyclic $C_1$-$C_{12}$ aliphatic radical that may be independently substituted by 1-5 same or different substituents, $R^4$ is a hydrogen, an unsaturated or saturated, linear, branched or cyclic $C_1$-$C_{12}$ aliphatic radical that can be substituted by 1-5 same or different substituents, a $C_6$-$C_{20}$ aryl group that can be substituted by 1-5 same or different substituents, a 5-20 membered heteroaryl group comprising 1 to 5 same or different heteroatoms or heteroatom groups selected from N, O, S, C=O or C=S that can be substituted by 1-5 same or different substituents, a linear or cyclic acyl group with up to 8 carbon atoms that may be substituted by 1-5 same or different substituents, an amino protective group or a $SO_2$—Ar, wherein Ar is as defined above, $R^5$, $R^6$ are independently of each other hydrogen, a $C_6$-$C_{20}$ aryl group that can be substituted by 1-5 same or different substituents, a 5-20 membered heteroaryl group comprising 1 to 5 same or different heteroatoms or heteroatom groups selected from N, O, S, C=O or C=S that can be substituted by 1-5 same or different substituents, a linear or cyclic acyl group with up to 8 carbon atoms that can be substituted by 1-5 same or different substituents, or an unsaturated or saturated, linear, branched or cyclic $C_1$-$C_{12}$ aliphatic radical that may be substituted by 1-5 same or different substituents, $R^7$, $R^8$ are independently of each other hydrogen, a $C_6$-$C_{20}$ aryl group that can be substituted by 1-5 same or different substituents, a 5-20 membered heteroaryl group comprising 1 to 5 same or different heteroatoms or heteroatom groups selected from N, O, S, C=O or C=S that can be substituted by 1-5 same or different substituents, a linear or cyclic acyl group with up to 8 carbon atoms that can be substituted by 1-5 same or different substituents, or an unsaturated or saturated, linear, branched or cyclic $C_1$-$C_{12}$ aliphatic radical that may be independently substituted by 1-5 same or different substituents, and wherein the photochemical reaction is performed under UV light in the range of 190-400 nm.

2. The method for the regiocontrolled preparation of a biaryl compound of general formula (I) according to claim 1, wherein Ar and Ar', independently of each other, represent a $C_6$-$C_{20}$ aryl group or a 5-20 membered heteroaryl group, wherein the $C_6$-$C_{20}$ aryl group and the 5-20 membered heteroaryl group, independently of each other, can be substituted by one or more same or different substituent(s), independently selected from the group(s) consisting of a group —$OR^9$, a linear, branched or cyclic saturated or unsaturated aliphatic group, a branched, linear or cyclic saturated or unsaturated heteroaliphatic group, CN, F, Cl, a branched, linear or cyclic —(C=O)$R^{10}$ group, an aryl or heteroaryl group, a —$SR^{11}$, a group —$(CR^{12}R^{13})_{0-1}NR^{14}R^{15}$, a —$B(OR^{16})_2$, —$SnR^{17}R^{18}R^{19}$, —$N_3$, a —$COOR^{20}$ group, a —$CONR^{21}R^{22}$ group, a —$SO_2OR^{23}$ group, or a —$SO_2NR^{24}R^{25}$ group, wherein $R^9$ within the definition —$OR^9$ refers to a hydrogen, an unsaturated or saturated, linear, branched or cyclic $C_1$-$C_{12}$ aliphatic radical that may be independently substituted by one or more groups selected from an OH, $NH_2$ group, CN, F, Cl, carboxyalkyl group consisting of a straight or branched $C_1$-$C_6$ alkyl or a $C_3$-$C_6$ cycloalkyl, a $C_6$-$C_{20}$ aryl group or a 5-20 membered heteroaryl group, wherein each of the groups independently can be substituted; $R^9$ can further be a branched, linear or cyclic —(C=O)$R^{10}$ group, a $C_6$-$C_{20}$ aryl group that can be substituted, a 5-20-membered heteroaryl group that can be substituted, or an alcohol protective group, $R^{10}$ in the group —(C=O)$R^{10}$ refers to a hydrogen, unsaturated or saturated, linear, branched or cyclic aliphatic radical having 1-8 carbon atoms that may be independently substituted by one or more groups selected from an OH, $NH_2$, CN, F, Cl, COOH, a $C_6$-$C_{20}$ aryl group, a 5-20 membered heteroaryl group or a carboxyalkyl group, wherein the alkyl radical consists of a straight or branched $C_1$-$C_6$ alkyl or a $C_3$-$C_6$ cycloalkyl, wherein each of the groups independently can be substituted; $R^{10}$ can further be a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein each of the groups independently can be substituted, $R^{11}$ in the group —$SR^{11}$ group denotes a hydrogen, unsaturated or saturated, linear, branched or cyclic aliphatic radical having 1-8 carbon atoms that may be independently substituted by one or more groups selected from an OH, $NH_2$, CN, F, Cl, carboxyalkyl group, wherein the alkyl radical consists of a straight or branched $C_1$-$C_6$ alkyl or a $C_3$-$C_6$ cycloalkyl, wherein each of the groups independently can be substituted; $R^{11}$ can further be a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, wherein each of the groups independently can be substituted, or $R^{11}$ denotes a sulfur protective group, $R^{14}$ and $R^{15}$ in the group —$(CR^{12}R^{13})_{0-1}$—$NR^{14}R^{15}$ independently of each other refer to hydrogen, an unsaturated or saturated, linear, branched or cyclic aliphatic radical having 1-8 carbon atoms that may be independently substituted by one or more groups selected from OH, $NH_2$, CN, F, Cl, or a carboxyalkyl group, wherein the alkyl radical consists of a straight or branched $C_1$-$C_6$ alkyl or a $C_3$-$C_6$ cycloalkyl, wherein each of the groups independently can be substituted; $R^{14}$ and $R^{15}$ can further independently of each other be a branched, linear or cyclic $C_1$-$C_8$ acyl group, a $(SO_2)_{0-1}$—$C_6$-$C_{20}$ aryl group or a $(SO_2)_{0-1}$-5-14 membered monocyclic or bicyclic heteroaryl group comprising 1 to 4 same or different heteroatoms or heteroatom groups selected from N, O, S, C=O or C=S, wherein each of the groups independently can be substituted, or $R^{14}$, $R^{15}$ denote an (amino) protective group and $R^{12}$, $R^{13}$ are independently of each other hydrogen, a $C_6$-$C_{20}$ aryl group, a 5-14-membered monocyclic or bicyclic heteroaryl group comprising 1 to 4 same or different heteroatoms selected from N, O, S, C=O and C=S, a linear or cyclic $C_1$-$C_8$ acyl group, wherein each of the groups independently can be substituted, or an unsaturated or saturated, linear, branched or cyclic aliphatic radical having 1 to 8 carbon atoms that may be independently substituted by an OH group, the substituents $R^{16}$ in the group $B(OR^{16})_2$ independently of each other refer to hydrogen, an unsaturated or saturated, linear, branched or cyclic aliphatic radical having 1-8 carbon atoms that may be independently substituted by one or more OH group(s) or (alcohol) protecting group(s); or taken together may also be part of a single cyclic residue, the substituents $R^{17}$, $R^{18}$, $R^{19}$ at the group $SnR^{17}R^{18}R^{19}$ independently of each other refer to an unsaturated or saturated, linear, branched or cyclic aliphatic radical having 1-8 carbon atoms, a $C_6$-$C_{20}$ aryl group, or a 5-14 membered monocyclic or bicyclic heteroaryl group comprising 1 to 4 same or different heteroatoms or heteroatom groups selected from N, O, S, C=O or C=S, wherein the $C_1$-$C_8$ aliphatic radical, the $C_6$-$C_{20}$ aryl group, the 5-14 membered heteroaryl group, in turn, can be substituted, $R^{20}$ in the definition —$COOR^{20}$ represents hydrogen, an unsaturated or saturated, linear, branched or cyclic aliphatic radical having 1-8 carbon atoms that may be independently substituted by one or more groups selected from OH, $NH_2$, CN, Cl, F, a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, wherein the $C_6$-$C_{20}$ aryl group and the 5-14 membered heteroaryl group, in turn, can be substituted, or $R^{16}$ refers to a carboxylic acid protective group, $R^{21}$ and $R^{22}$ in the group —$CONR^{21}R^{22}$ independently of each other refer to hydrogen, an unsaturated or saturated, linear, branched or cyclic aliphatic radical having 1-8 carbon atoms that may be independently substituted by one or more groups selected from OH, $NH_2$, CN, F, Cl, a carboxyalkyl group, wherein the alkyl radical consists of a straight or branched $C_1$-$C_6$ alkyl or a $C_3$-$C_6$ cycloalkyl, a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_1$-$C_6$ alkyl group, the $C_3$-$C_6$ cycloalkyl group, the $C_6$-$C_{20}$ aryl group and the 5-14 membered heteroaryl group, in turn, can be substituted, or $R^{21}$, $R^{22}$ may further be selected from a $C_6$-$C_{20}$ aryl or a 5-14 membered monocyclic or bicyclic heteroaryl group comprising 1 to 4 same or different heteroatoms or heteroatom groups selected from N, O, S, C=O or C=S, wherein the $C_6$-$C_{20}$ aryl or the 5-14 membered heteroaryl group, in turn, can be substituted, $R^{23}$ within the definition of the group —$SO_2OR^{23}$ refers to a hydrogen atom, an unsaturated or saturated, linear, branched or cyclic aliphatic radical having 1-8 carbon atoms that may be independently substituted by one or more groups selected from OH, $NH_2$, CN, F, Cl, a carboxyalkyl group, wherein the alkyl radical consists of a straight or branched $C_1$-$C_6$ alkyl or a $C_3$-$C_6$ cycloalkyl, a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_1$-$C_6$ alkyl group, the $C_3$-$C_6$ cycloalkyl group, the $C_6$-$C_{20}$ aryl group and the 5-14-membered heteroaryl group, in turn, can be substituted, or $R^{23}$ can further be a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, wherein the $C_6$-$C_{20}$ aryl or the 5-14 membered heteroaryl group, in turn, can be substituted, $R^{24}$ and $R^{25}$ within the term —$SO_2NR^{24}R^{25}$ are independently of each other hydrogen, an unsaturated or saturated, linear, branched or cyclic aliphatic radical having 1-8 carbon atoms, a —$(CR^{12}R^{13})_{0-1}$—$C_6$-$C_{20}$-aryl or a —$(CR^{12}R^{13})_{0-1}$-5-14 membered monocyclic or bicyclic heteroaryl group comprising 1 to 4 same or different heteroatoms selected from N, O, S, C=O and C=S, a linear or cyclic $C_1$-$C_8$ acyl group, wherein the $C_1$-$C_8$ aliphatic radical, the $C_6$-$C_{20}$-aryl group, the 5-14 membered heteroaryl group and the $C_1$-$C_8$ acyl group, in turn, can be substituted, or $R^{24}$, $R^{25}$ refer to an amino protective group, and wherein $R^{12}$ and $R^{13}$ are independently of each other hydrogen, a $C_6$-$C_{20}$ aryl group or a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or an unsaturated or saturated, linear, branched or cyclic aliphatic radical having 1-8 carbon atoms that may be independently substituted by an OH group, L represents a group —X—Y—Z— wherein X, Y, Z are independently of each other selected from

X=$SO_2$, (P=O)$OR^1$, or $SiR^2R^3$,
Y=$NR^4$, O, or $CR^5R^6$,
Z=$CR^7R^8$, and $R^1$ is a hydrogen, an unsaturated or saturated, linear, branched or cyclic aliphatic radical having 1-8 carbon atoms that may be substituted, a phenyl or benzyl group, $R^2$, $R^3$ are independently of each other a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or an unsaturated or saturated, linear, branched or cyclic aliphatic radical having 1-8 carbon atoms that may be independently substituted by an OH group, $R^4$ is a hydrogen, an unsaturated or saturated, linear, branched or cyclic aliphatic radical having 1-8 carbon atoms, a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or a $SO_2$—Ar group, wherein Ar is as defined above, $R^5$, $R^6$ are independently of each other hydrogen, a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or an unsaturated or saturated, linear, branched or cyclic aliphatic radical having 1-8 carbon atoms that may be independently substituted by an OH group, $R^7$, $R^8$ are independently of each other hydrogen, a $C_6$-$C_{20}$ aryl group, a 5-14 membered monocyclic or bicyclic heteroaryl group comprising 1 to 4 same or different heteroatoms or heteroatom groups selected from N, O, S, C=O or C=S, a linear or cyclic $C_1$-$C_8$ acyl group or an unsaturated or saturated, linear, branched or cyclic aliphatic radical having 1-8 carbon atoms that may be independently substituted by an OH group and wherein the photochemically driven reaction is performed in a solution of the respective precursor compound of formula (II) in a photo-reactor consisting of a light source (UV emissions in the range of 190-400 nm) and a UV-transparent chamber or flow cell, or alternatively wherein the precursor compound of formula (II) is irradiated as a solvent-free thin-film on a solid support.

3. The method for the regiocontrolled preparation of a biaryl compound of general formula (I) according to claim 1, characterized in that the photochemically driven reaction is performed in a solution of the respective precursor of formula (II) in a photo-reactor consisting of a light source (UV emissions in the range of 190-400 nm, irradiation power of 0.01 mW/cm$^2$ to 10 W/cm$^2$) and a UV-transparent chamber or flow cell, at flow rates of $10^{-7}$ L/min to $10^{-3}$ L/min per cm$^2$ light exposed window area.

4. The method for the regiocontrolled preparation of a biaryl compound of general formula (I) according to claim 3, wherein the solvent is selected from the groups consisting of alcohols, alkylnitrils, ethers, toluene, dimethylsulfoxide, acetone and/or mixtures thereof.

5. The method for the regiocontrolled preparation of a biaryl compound of general formula (I) according to claim 1, wherein the respective precursor compound of formula (II) according to claim 1 is irradiated with a suitable light source as a solvent-free thin film on a solid support, wherein the specific surface loads are in the range of $10^{-5}$ to 1 mol·m$^{-2}$.

6. The method for the regiocontrolled preparation of a biaryl compound of general formula (I) according to claim 5, wherein the reaction proceeds in thin layers on surfaces, in light transparent solid matrices or on polymer surfaces.

7. The method for the regiocontrolled preparation of a biaryl compound of general formula (I) according to claim 1, characterized in that Ar and Ar', independently of each other, represent a phenyl, naphthyl, furanyl, imidazolyl, pyridyl, thiazolyl, thiophenyl, furanyl, pyrimidyl, pyrazinyl, benzothiazolyl and indolyl group, wherein the above-mentioned groups can be substituted by one or more same or different substituent(s) selected from —OH, —$OCH_3$, a linear, branched or cyclic saturated or unsaturated aliphatic group with 1 to 6 carbon atoms, CN, F, Cl, a —(C=O)H or —(C=O)$CH_3$ group, a phenyl or pyridyl group, a —NH$_2$ group, —N(CH$_3$)$_2$ group, N$_3$, a —COOH, a —COOCH$_3$ group, a —CONH$_2$, a —CONHCH$_3$ or a —CONCH$_3$CH$_3$ group, the groups —X—Y—Z— are independently of each other selected from X=SO$_2$,
Y=NR$^4$ or O
Z=CR$^7$R$^8$,
and wherein R$^4$ is a hydrogen, an unsaturated or saturated, linear, branched or cyclic aliphatic radical having 1-8 carbon atoms that can be substituted, a C$_6$-C$_{20}$ aryl that can be substituted or a 5-14 membered monocyclic or bicyclic heteroaryl group comprising 1 to 4 same or different heteroatoms selected from N, O, S, C=O and C=S that can be substituted, a linear or cyclic C$_1$-C$_8$ acyl group that may be substituted or a SO$_2$—Ar group, wherein Ar is as defined above, R$^7$, R$^8$ are independently of each other hydrogen, C$_6$-C$_{20}$ aryl that can be substituted or a 5-14 membered monocyclic or bicyclic heteroaryl group comprising 1 to 4 same or different heteroatoms selected from N, O, S, C=O and C=S that can be substituted, a linear or cyclic C$_1$-C$_8$ acyl group that may be substituted, or an unsaturated or saturated, linear, branched or cyclic aliphatic radical having 1-8 carbon atoms that may be independently substituted by an OH group.

8. The method for the regiocontrolled preparation of a biaryl compound of general formula (I) according to claim 1, wherein X is —SO$_2$—.

9. The method for the regiocontrolled preparation of a biaryl compound of general formula (I) according to claim 2, wherein X is —SO$_2$—.

10. The method for the regiocontrolled preparation of a biaryl compound of general formula (I) according to claim 1, wherein Y is —NH—.

11. The method for the regiocontrolled preparation of a biaryl compound of general formula (I) according to claim 2, wherein Y is —NH—.

12. The method for the regiocontrolled preparation of a biaryl compound of general formula (I) according to claim 7, wherein Y is —NH—.

13. The method for the regiocontrolled preparation of a biaryl compound of general formula (I) according to claim 2, wherein Z is CH$_2$.

14. The method for the regiocontrolled preparation of a biaryl compound of general formula (I) according to claim 7, wherein Z is CH$_2$.

15. The method for the regiocontrolled preparation of a biaryl compound of general formula (I) according to claim 1, wherein the photochemical reaction is performed under UV light at 254 nm.

16. The method for the regiocontrolled preparation of a biaryl compound of general formula (I) according to claim 2, wherein the photochemical reaction is performed under UV light at 254 nm.

17. The method for the regiocontrolled preparation of a biaryl compound of general formula (I) according to claim 7, wherein —X—Y—Z— is —SO$_2$—NH—CH$_2$—.

18. The method for the regiocontrolled preparation of a biaryl compound of general formula (I) according to claim 7, wherein R$^7$ and R$^8$ are both hydrogen, or R$^7$ and R$^8$ independently of each other are hydrogen, methyl or ethyl, wherein the methyl or ethyl group(s) independently can be substituted by an OH group.

* * * * *